(12) United States Patent
Nishide et al.

(10) Patent No.: US 11,917,912 B2
(45) Date of Patent: Feb. 27, 2024

(54) ORGANIC COMPOUND, ORGANIC LIGHT-EMITTING ELEMENT, DISPLAY APPARATUS, PHOTOELECTRIC CONVERSION APPARATUS, ELECTRONIC APPARATUS, ILLUMINATION APPARATUS, MOVING OBJECT, AND EXPOSURE LIGHT SOURCE

(71) Applicant: CANON KABUSHIKI KAISHA, Tokyo (JP)

(72) Inventors: Yosuke Nishide, Kanagawa (JP); Jun Kamatani, Tokyo (JP); Naoki Yamada, Tokyo (JP); Hironobu Iwawaki, Kanagawa (JP); Hirokazu Miyashita, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/556,827

(22) Filed: Dec. 20, 2021

(65) Prior Publication Data

US 2022/0216423 A1     Jul. 7, 2022

(30) Foreign Application Priority Data

Dec. 25, 2020 (JP) ................ 2020-216220

(51) Int. Cl.
| | |
|---|---|
| *C07D 498/10* | (2006.01) |
| *H10K 85/60* | (2023.01) |
| *C07D 513/10* | (2006.01) |
| *C07D 517/10* | (2006.01) |
| *C09K 11/06* | (2006.01) |
| *H10K 50/11* | (2023.01) |
| *H10K 101/10* | (2023.01) |

(52) U.S. Cl.
CPC .......... *H10K 85/657* (2023.02); *C07D 498/10* (2013.01); *C07D 513/10* (2013.01); *C07D 517/10* (2013.01); *C09K 11/06* (2013.01); *C09K 2211/1018* (2013.01); *H10K 50/11* (2023.02); *H10K 2101/10* (2023.02)

(58) Field of Classification Search
CPC .................................................. C07D 498/10
See application file for complete search history.

(56) References Cited

U.S. PATENT DOCUMENTS

| | | |
|---|---|---|
| 2012/0001537 A1 | 1/2012 | Lin et al. |
| 2016/0093823 A1 | 3/2016 | Seo et al. |
| 2019/0337872 A1 | 11/2019 | Saito et al. |

FOREIGN PATENT DOCUMENTS

| | | |
|---|---|---|
| CN | 108219779 A | 6/2018 |
| CN | 108383847 A | 8/2018 |
| CN | 109970775 A | 7/2019 |
| CN | 111620890 A | 9/2020 |

OTHER PUBLICATIONS

American Chemical Society. Chemical Abstract Service. RN 2738514-69-5. Entered into STN/first public availability date: Nov. 30, 2021. (Year: 2021).*

Yang, D., et al. "Spiro-type TADF emitters based on acridine donors and anthracenone acceptor." Dyes and Pigments. (2022), vol. 197, 109873, pp. 1-6. (Year: 2022).*

* cited by examiner

*Primary Examiner* — John S Kenyon
(74) *Attorney, Agent, or Firm* — Canon U.S.A., Inc., IP Division

(57) ABSTRACT

An organic compound is represented by general formula [1-1].

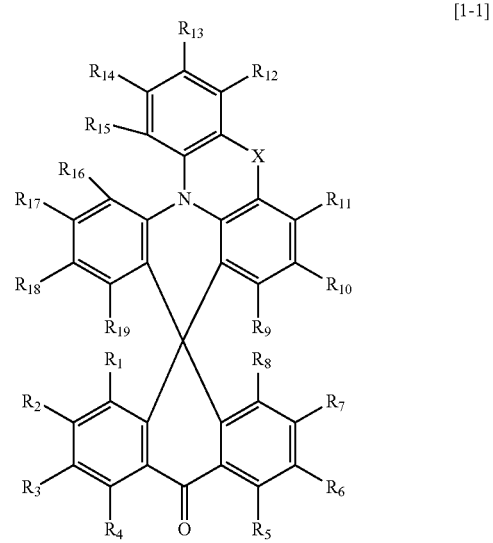

In general formula [1-1], X is an oxygen atom, a sulfur atom, a selenium atom, or a tellurium atom, and $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group.

20 Claims, 11 Drawing Sheets

| | COMPARATIVE COMPOUND 1-a | EXEMPLARY COMPOUND A1 |
|---|---|---|
| SYMMETRY AND HOW TRANSITION OCCURS | BILATERALLY SYMMETRIC / ROTATION AXIS PRESENT  |  |
| HOMO, LUMO (calc.) |  HOMO   LUMO |  HOMO   LUMO |
| OSCILLATOR STRENGTH (calc.) [−] | 0 | $3 \times 10^{-4}$ |

| | COMPARATIVE COMPOUND 2-a | EXEMPLARY COMPOUND A1 |
|---|---|---|
| MOLECULAR STRUCTURE |  |  |
| HOMO (calc.) |  |  |
| LUMO (calc.) |  |  |
| S1 (calc.) [nm] | 427 | 461 |
| T1 (calc.) [nm] | 431 | 464 |
| ΔST [nm] | 4 | 3 |

ORGANIC COMPOUND, ORGANIC LIGHT-EMITTING ELEMENT, DISPLAY APPARATUS, PHOTOELECTRIC CONVERSION APPARATUS, ELECTRONIC APPARATUS, ILLUMINATION APPARATUS, MOVING OBJECT, AND EXPOSURE LIGHT SOURCE

BACKGROUND OF THE INVENTION

Field of the Invention

The present disclosure relates to an organic compound, an organic light-emitting element, a display apparatus, a photoelectric conversion apparatus, an electronic apparatus, an illumination apparatus, a moving object, and an exposure light source.

Description of the Related Art

An organic light-emitting element (hereinafter also referred to as an "organic electroluminescent element" or an "organic EL element") is an electronic element including a pair of electrodes and an organic compound layer disposed between the electrodes. By injecting electrons and holes through the pair of electrodes, excitons of a luminescent organic compound in the organic compound layer are generated. The organic light-emitting element emits light when the excitons return to their ground state.

Recent progress in organic light-emitting elements has been noticeable. For example, low driving voltages, various emission wavelengths, high-speed response, and thinner and lighter light-emitting devices have been enabled.

Regarding organic light-emitting elements having higher efficiency, elements produced using efficiency-improving materials such as phosphorescent materials or delayed fluorescent materials have been reported. U.S. Patent Application Publication No. 2012/0001537 discloses compound 1-a below, and Chinese Patent Application Publication No. 108383847 discloses compound 2-a below.

1-a

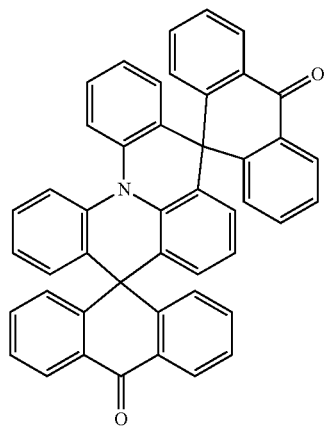

2-a

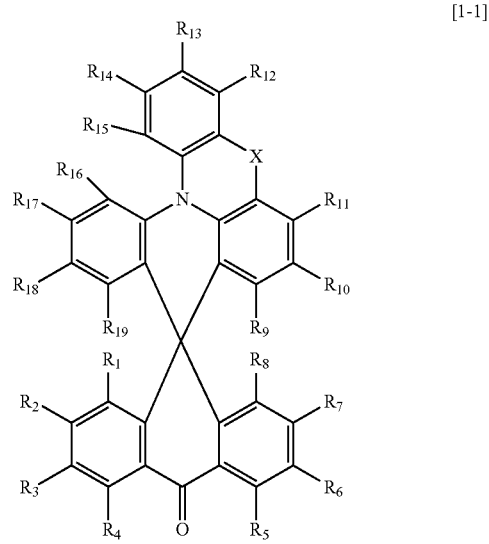

When compound 1-a disclosed in U.S. Patent Application Publication No. 2012/0001537 or compound 2-a disclosed in Chinese Patent Application Publication No. 108383847 is used for a light-emitting layer in an organic light-emitting element, there is still a problem with light emission efficiency.

The present disclosure eclipses the existing compounds and provides an organic compound having high light emission efficiency.

SUMMARY OF THE INVENTION

The present disclosure provides an organic compound represented by general formula [1-1]:

[1-1]

wherein, in general formula [1-1], X is an oxygen atom, a sulfur atom, a selenium atom, or a tellurium atom, and $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group.

Further features of the present disclosure will become apparent from the following description of exemplary embodiments with reference to the attached drawings.

DESCRIPTION OF THE EMBODIMENTS

Organic Compound

Figure 1A:
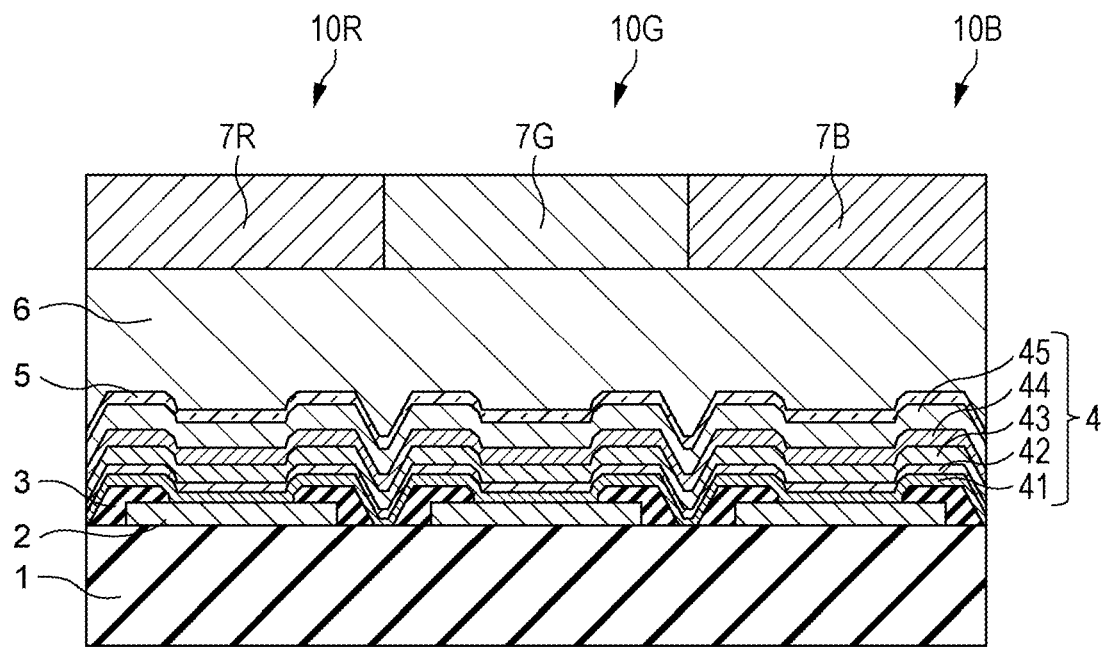
FIG. 1A is a schematic sectional view illustrating an example of a pixel of a display apparatus according to an embodiment of the present disclosure.

An organic compound according to an embodiment will first be described. The organic compound according to this embodiment is represented by general formula [1-1] below.

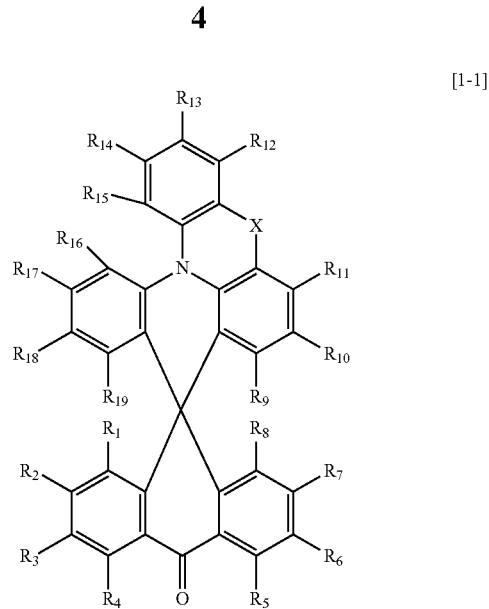

[1-1]

In general formula [1-1], X is an oxygen atom, a sulfur atom, a selenium atom, or a tellurium atom. $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group.

In general formula [1-1], $R_1$ to $R_{18}$ may each independently be selected from the group consisting of a hydrogen atom, a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aromatic hydrocarbon group having 6 to 60 carbon atoms, a substituted or unsubstituted heterocyclic group having 3 to 60 carbon atoms, a substituted or unsubstituted aryloxy group, a substituted or unsubstituted silyl group, and a cyano group.

In general formula [1-1], X is preferably an oxygen atom, a sulfur atom, or a selenium atom, more preferably an oxygen atom or a sulfur atom.

Examples of halogen atoms suitable as $R_1$ to $R_{18}$ include a fluorine atom, a chlorine atom, a bromine atom, and an iodine atom, but are not limited thereto.

Examples of alkyl groups suitable as $R_1$ to $R_{18}$ include a methyl group, an ethyl group, an n-propyl group, an isopropyl group, an n-butyl group, a tert-butyl group, a sec-butyl group, an octyl group, a cyclohexyl group, a 1-adamantyl group, and a 2-adamantyl group, but are not limited thereto.

Examples of alkoxy groups suitable as $R_1$ to $R_{18}$ include a methoxy group, an ethoxy group, a propoxy group, a 2-ethyl-octyloxy group, and a benzyloxy group, but are not limited thereto.

Examples of amino groups suitable as $R_1$ to $R_{18}$ include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, an N-phenyl-N-(4-trifluoromethylphenyl)amino group, an N-piperidyl group, a carbazolyl group, and an acridyl group, but are not limited thereto.

Examples of aromatic hydrocarbon groups suitable as $R_1$ to $R_{18}$ include a phenyl group, a naphthyl group, an indenyl group, a biphenyl group, a terphenyl group, a fluorenyl group, a phenanthryl group, a triphenylenyl group, a pyrenyl group, an anthranil group, a perylenyl group, a chrysenyl group, and a fluoranthenyl group, but are not limited thereto.

Examples of heterocyclic groups suitable as $R_1$ to $R_{18}$ include a pyridyl group, a pyrimidyl group, a pyrazyl group, a triazyl group, a benzofuranyl group, a benzothiophenyl group, a dibenzofuranyl group, a dibenzothiophenyl group, an oxazolyl group, an oxadiazolyl group, a thiazolyl group, a thiadiazolyl group, a carbazolyl group, an acridinyl group, and a phenanthrolyl group, but are not limited thereto.

Examples of aryloxy groups suitable as $R_1$ to $R_{18}$ include a phenoxy group and a thienyloxy group, but are not limited thereto.

Examples of silyl groups suitable as $R_1$ to $R_{18}$ include a trimethylsilyl group and a triphenylsilyl group, but are not limited thereto.

Examples of substituents that the alkyl groups, the alkoxy groups, the amino groups, the aryl groups, the heterocyclic groups, the aryloxy groups, and the silyl groups described above may further have include alkyl groups such as a methyl group, an ethyl group, an n-propyl group, an isopropyl group, an n-butyl group, and a tert-butyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxy groups such as a methoxy group, an ethoxy group, and a propoxy group; aryloxy groups such as a phenoxy group; halogen atoms such as fluorine, chlorine, bromine, and iodine; and a cyano group, but are not limited thereto.

Next, a method of synthesizing the organic compound according to this embodiment will be described. The organic compound according to this embodiment is synthesized according to, for example, the following reaction scheme.

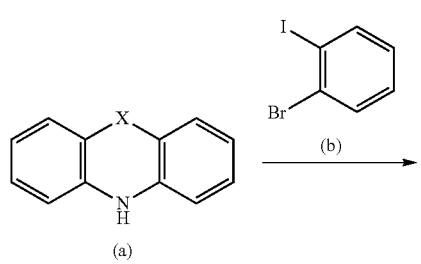

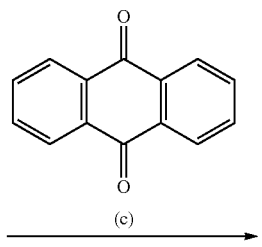

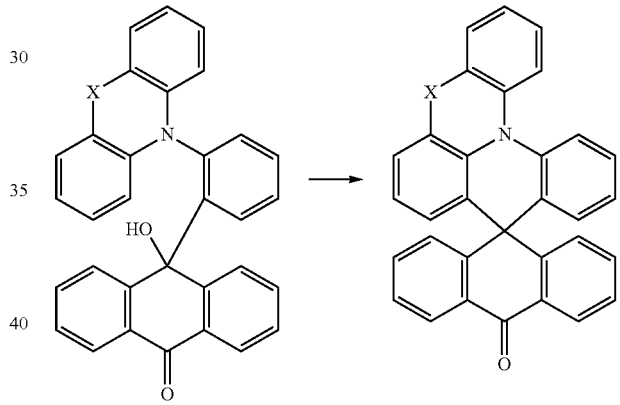

In the above reaction scheme, compounds represented by (a) to (c) may be appropriately changed to thereby obtain compounds represented by general formula [1-1] with various X and various substituents $R_1$ to $R_{18}$. It should be noted that this is not the only synthesis method. Specific synthesis methods will be described in detail in EXAMPLES.

Next, features of the organic compound according to this embodiment will be described. The organic compound according to this embodiment has features as described below. Due to these features, using the organic compound according to this embodiment in an organic light-emitting element can provide an organic light-emitting element having high light emission efficiency. In the following description, the term "basic skeleton" refers to a compound represented by general formula [1-1] where $R_1$ to $R_{18}$ are all hydrogen atoms.

Hereinafter, the features of the present disclosure will be described by comparing exemplary compound A1, which is a compound represented by general formula [1-1], with comparative compound 1-a disclosed in U.S. Patent Application Publication No. 2012/0001537.

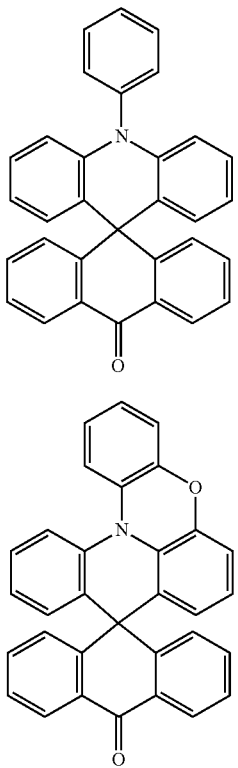

(1) Due to a basic skeleton having an asymmetric structure, oscillator strength is high, and light emission efficiency is high.

The higher the probability of transition between the ground state and an excited state of an organic compound is, the more efficient light emission can be obtained when the organic compound is used as a light-emitting material. One known indicator of the probability of transition between the ground state and an excited state is oscillator strength. As the oscillator strength increases, the probability of transition between the ground state and an excited state increases, and the light emission efficiency increases.

Figure 9:
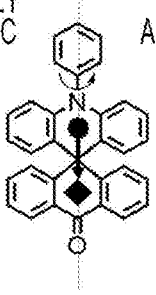
FIG. 9 illustrates the electron distribution of HOMO and LUMO of comparative compound 1-a and exemplary compound A1.
Figure 9:
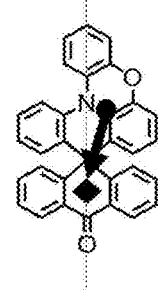
Figure 9:
Figure 9:
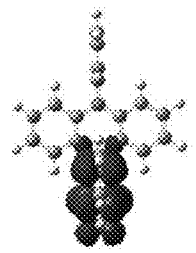

In creating an organic compound represented by general formula [1-1], the present inventors focused on the presence of a symmetry axis in the compound and the transition dipole moment of the compound. To estimate the transition dipole moment, electron distributions of HOMO (highest occupied molecular orbital) and LUMO (lowest unoccupied molecular orbital) were calculated, and the center of gravity thereof was determined. The calculation results for comparative compound 1-a and exemplary compound A1 are illustrated in FIG. 9. In the structural formulae in FIG. 9, the position of the center of gravity of HOMO is indicated by a black circle, and the position of the center of gravity of LUMO is indicated by a square (black rhombus).

As illustrated in FIG. 9, comparative compound 1-a has a molecular structure bilaterally symmetric about a rotation position of the phenyl group bonded to a nitrogen atom. In this case, the center of gravity of the electron distribution of HOMO and the center of gravity of the electron distribution of LUMO both lie on this symmetry axis. Thus, the transition dipole moment from HOMO to LUMO is inhibited, decreasing the probability of transition between the ground state and an excited state. The oscillator strength of comparative compound 1-a was calculated and found to be 0.

By contrast, exemplary compound A1 according to this embodiment has a fused-ring structure in which the phenyl group bonded to a nitrogen atom is bonded to another aromatic ring through an oxygen atom. Therefore, exemplary compound A1 has a bilaterally asymmetric molecular structure in which the symmetry axis present in comparative compound 1-a does not exist. Furthermore, due to the use of a chalcogen atom such as an oxygen atom, a sulfur atom, a selenium atom, or a tellurium atom as a substituent X in general formula [1-1], the electron orbital of HOMO is distributed also on X. Actually, in exemplary compound A1, the electron orbital distribution of HOMO is present also on the oxygen atom, as illustrated in FIG. 9. As a result of this, the center of gravity of the electron orbital distribution of HOMO is shifted toward the oxygen atom and deviated from the symmetry axis in comparative compound 1-a. Due to this, the transition dipole moment from HOMO to LUMO is also deviated from the symmetry axis, thus suppressing a decrease in the probability of transition between the ground state and an excited state. The oscillator strength of exemplary compound A1 was calculated and found to be $3\times10^{-4}$, which was larger than that of comparative compound 1-a.

From the above, it follows that the organic compounds according to this embodiment as well as exemplary compound A1 each have an asymmetric basic skeleton. Thus, the transition dipole moment is not inhibited, the oscillator strength is high, and the light emission efficiency is high.

(2) Due to a basic skeleton with no rotation axis, the loss of excitation energy is suppressed, and light emission efficiency is high.

Furthermore, in creating an organic compound represented by general formula [1-1], the present inventors focused on the presence of a rotation axis of the basic skeleton of the compound.

When a molecule enters an excited state in response to light or electrical stimulation and then emits light to return to the ground state, it is desired that all the energy applied be used for the light emission from the viewpoint of light emission efficiency. Actually, however, part of the excitation energy is lost as vibrational energy of the molecule. Accordingly, the light emission efficiency decreases by the amount of lost energy. Thus, to suppress the loss due to molecular vibration and improve the light emission efficiency, the basic skeleton related to the light emission process preferably does not have a bonded rotation axis.

As illustrated in FIG. 9, comparative compound 1-a has, in its basic skeleton, a phenyl group bonded only to a nitrogen atom. This phenyl group rotates around the bond axis between the nitrogen atom and the carbon atom bonded to the nitrogen atom. As a result, in comparative compound 1-a, energy loss due to rotational vibration occurs, and the light emission efficiency decreases.

By contrast, exemplary compound A1 according to this embodiment has a fused-ring structure in which the phenyl group bonded to a nitrogen atom is bonded to another aromatic ring through an oxygen atom, as illustrated in FIG. 9. Thus, the rotation of the phenyl group is restricted, and the rotation axis present in comparative compound 1-a does not exist. Therefore, energy loss due to vibration is suppressed, and highly efficient light emission is provided.

From the above, it follows that the organic compound according to the present disclosure as well as exemplary compound A1 has, as a basic skeleton, a structure not having a rotation axis in any state, and thus is less likely to undergo energy loss due to vibration and provides high light emission efficiency.

In this specification, the electron orbital distribution of HOMO and LUMO, the oscillator strength, and the energy of an excited singlet state ($S_1$) and an excited triplet state ($T_1$) were calculated using molecular orbital calculations and visualized. As a method of the molecular orbital calculations, the density functional theory (DFT), which is now widely used, was used.

The B3LYP functional and the 6-31G* basis function were used. The molecular orbital calculations were performed by Gaussian09 (Gaussian 09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford C T, 2010), which is now widely used. Hereinafter, molecular orbital calculations in this specification were performed using the same technique.

(3) Due to a basic skeleton having a fused-ring structure, liberation due to bond cleavage is less likely to occur, and durability is high.

A compound in an organic layer, particularly, a light-emitting layer, of an organic light-emitting element repeatedly undergoes transition between the ground state and an excited state during the process of light emission of the organic light-emitting element. In this process, strong molecular motions such as stretching and rotation occur. At this time, if there is a site where a bond readily dissociates, the bond may cleave to cause liberation of a portion of the compound. Since liberation of a portion of the compound causes a change in structure, the compound becomes less durable if liberation tends to occur. In addition, when such a compound is used in an organic light-emitting element, the liberated portion serves as a quencher and reduces element durability. Therefore, molecules having structures in which bond dissociation and liberation are less likely to occur have better durability.

Figure 10:
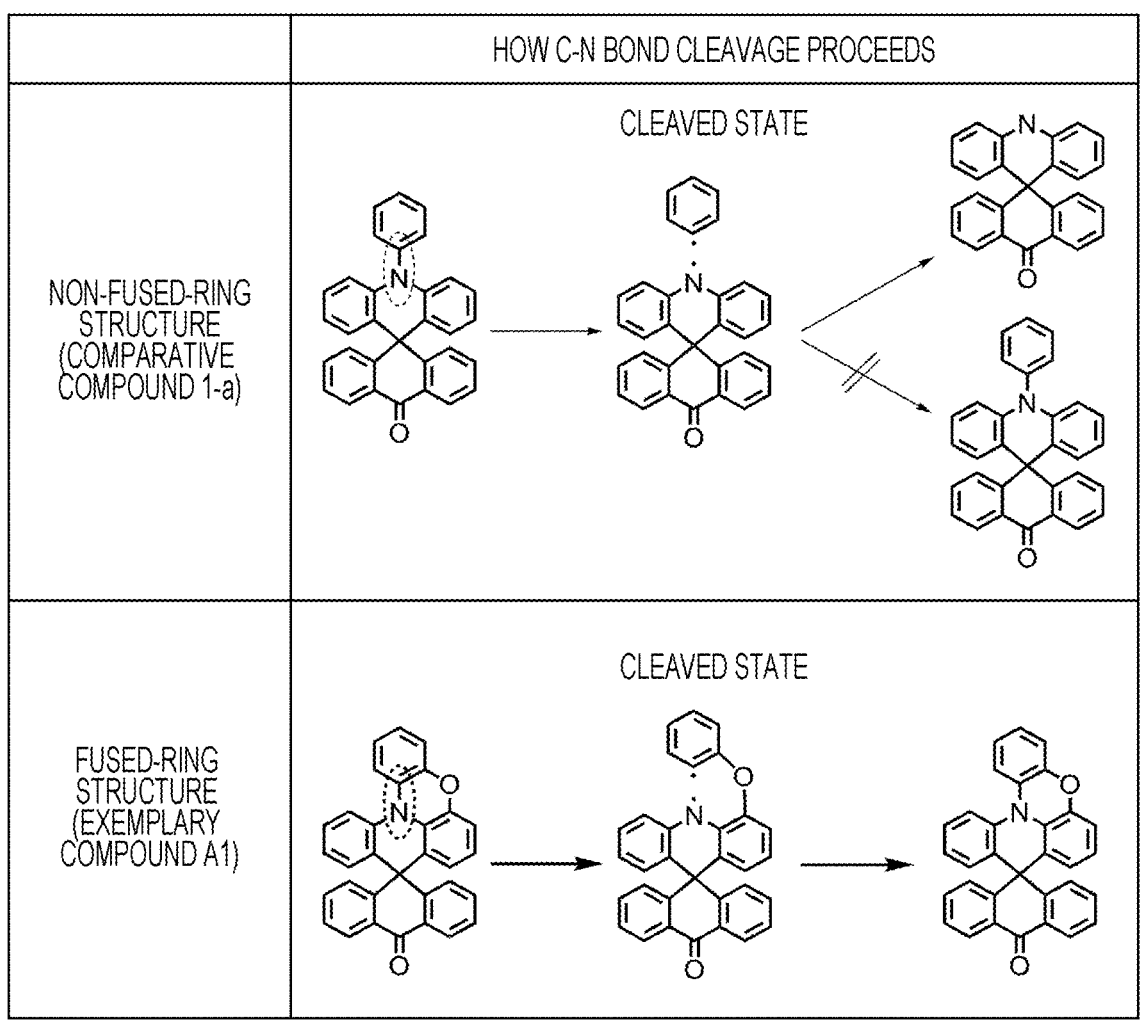
FIG. 10 illustrates how the C—N bond cleavage of comparative compound 1-a and exemplary compound A1 proceeds.

As illustrated in FIG. 10, in comparative compound 1-a, if the C—N bond in an area surrounded by a broken line is cleaved, the phenyl group after the cleavage is not bonded to any other site in the compound and thus will not readily be bonded again to return to the original compound. Thus, if cleavage occurs, a portion of the compound tends to be liberated to cause a change in structure. This results in a decrease in durability.

By contrast, in exemplary compound A1 according to this embodiment, if the C—N bond in an area surrounded by a broken line is cleaved, the phenyl group after the cleavage remains bonded to another site in the compound due to a fused-ring structure formed with an oxygen atom. Thus, the phenyl group will not be liberated and stays near the nitrogen atom to which the phenyl group was bonded before the cleavage of the C—N bond, and thus will readily be bonded again to return to the original structure. Therefore, the organic compound according to this embodiment is less likely to undergo liberation due to bond cleavage and has higher durability than comparative compound 1-a. Thus, when the compound according to this embodiment is used in an organic layer of an organic light-emitting element, liberation due to bond cleavage during driving of the element is less likely to occur, and thus the organic light-emitting element is less likely to undergo deterioration even if the element is driven for a long time and has high durability.

(4) Due to a basic skeleton having an asymmetric structure and a fused-ring structure, molecular association is less likely to occur, and thermal stability is high.

In an organic layer during driving of an organic light-emitting element, part of applied electric energy may be released in the form of thermal energy. Thus, if the thermal stability of a compound contained in the organic layer is low, the released thermal energy is likely to cause bond dissociation as described above. In addition, the released thermal energy may cause crystallization of an organic film. Bond dissociation and crystallization of an organic film lead to a decrease in element durability. Therefore, by using a compound having good film properties and high thermal stability, the element durability can be improved.

As described above, the basic skeleton of comparative compound 1-a has a symmetric structure. Thus, molecules tend to be regularly arranged in a film, and the crystallinity of the film tends to be high. That is to say, crystallization tends to occur. In addition, comparative compound 1-a does not have a fused-ring structure unlike exemplary compound A1, and thus is likely to undergo liberation of a portion of the molecule as a result of bond cleavage and has low thermal stability.

By contrast, the basic skeleton of exemplary compound A1 according to this embodiment has an asymmetric structure. Thus, molecules are less likely to be regularly arranged in a film, and the crystallinity of the film may decrease to form an amorphous film. That is to say, crystallization is less likely to occur. As a result, the film formed of exemplary compound A1 according to this embodiment has good film properties. An organic light-emitting element that is less likely to undergo crystallization if driven for a long time and has high durability can be obtained. In addition, exemplary compound A1 has a fused-ring structure and thus is less likely to undergo liberation of a portion of the molecule as a result of bond cleavage and has high thermal stability.

In addition, the asymmetric structure of the basic skeleton reduces the likelihood of molecular association. Thus, when the compound according to this embodiment is used in a light-emitting layer of an organic light-emitting element, since molecular association is less likely to occur, an organic light-emitting element that is less likely to undergo concentration quenching and emits light with high efficiency can be obtained.

Furthermore, the asymmetric structure of the basic skeleton also improves sublimability. Improvement in sublimability enables an increase in purity of a material by sublimation purification and the production of an organic light-emitting element by vapor deposition. This can reduce impurities contained in the organic light-emitting element, thus preventing the occurrence of a decrease in light emission efficiency due to impurities and a decrease in driving durability.

Next, further features of the present disclosure will be described by comparing exemplary compound A1, which is a compound represented by general formula [1-1], with comparative compound 2-a disclosed in Chinese Patent Application Publication No. 108383847.

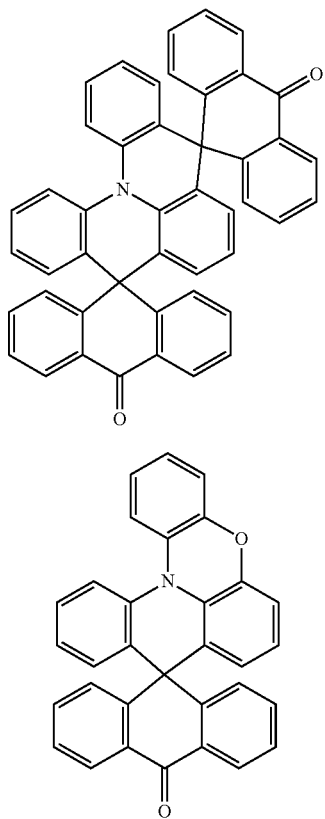

2-a

A1

(5) Due to a basic skeleton having an asymmetric structure and a chalcogen atom, the energy gap between $S_1$ and $T_1$ is small, and light emission efficiency is high.

The present inventors have found that the light emission efficiency is further improved by distributing HOMO in the molecule, particularly, on a chalcogen atom. Chalcogen atoms such as an oxygen atom, a sulfur atom, a selenium atom, and a tellurium atom are atoms heavier in mass than a carbon atom. When HOMO is distributed on a chalcogen atom heavier than a carbon atom, the transition from an excited triplet state to an excited singlet state is promoted by the heavy atom effect of the chalcogen atom. As a result, delayed fluorescent light emission, which is induced by transition of a molecule in an excited triplet state to an excited singlet state, can be produced with high efficiency.

Figure 11:
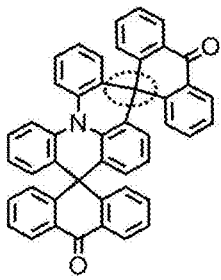
FIG. 11 illustrates the electron distribution of HOMO and LUMO and the calculation results of the energy of $S_1$ and $T_1$ of exemplary compound A1 and comparative compound 2-a.
Figure 11:
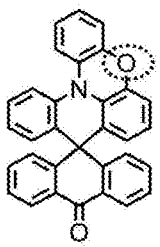
Figure 11:
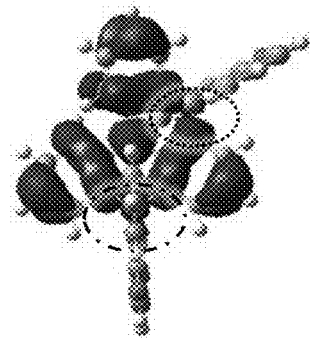
Figure 11:
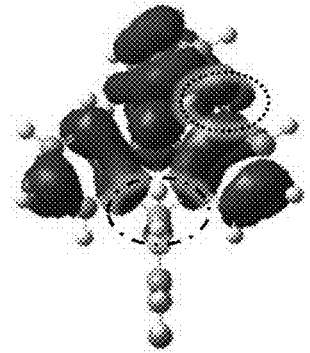
Figure 11:
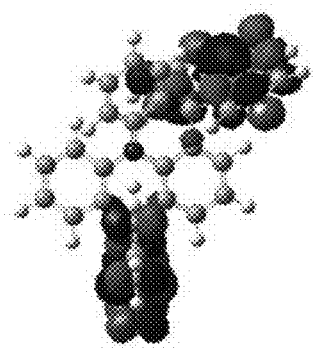
Figure 11:
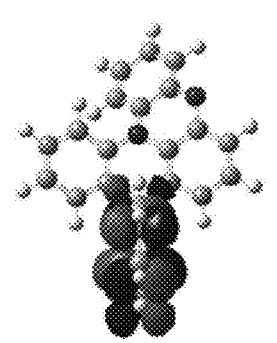

FIG. 11 illustrates the electron distribution of HOMO and LUMO and the calculation results of the energy of $S_1$ and $T_1$ of two compounds, exemplary compound A1 according to this embodiment and comparative compound 2-a. As illustrated in FIG. 11, for exemplary compound A1 according to this embodiment, HOMO is distributed also on an oxygen atom in the basic skeleton. Thus, in the compound according to this embodiment, the transition from an excited triplet state to an excited singlet state in promoted, thus leading to high light emission efficiency. By contrast, comparative compound 2-a has no chalcogen atoms, and moreover, HOMO is not distributed on the carbon atom located at the position corresponding to the chalcogen atom of exemplary compound A1. Thus, the transition from an excited triplet state to an excited singlet state is not promoted, thus leading to low light emission efficiency.

In exemplary compound A1, since HOMO is distributed also on an oxygen atom, the center of gravity of HOMO is shifted toward the oxygen atom. Thus, as indicated by a dot-dash line in FIG. 11, in comparative compound 2-a, HOMO is distributed also on the spiro carbon atom in an anthracenone moiety, while in exemplary compound A1, HOMO is not distributed on the spiro carbon atom in an anthracenone moiety. As a result, in exemplary compound A1, a portion where LUMO is distributed and a portion where HOMO is distributed are separated from each other in the molecule, and a portion where both LUMO and HOMO are distributed is small. This leads to a small overlap integral and a small energy difference between an excited singlet state ($S_1$) and an excited triplet state ($T_1$), which is preferred from the viewpoint of the efficiency of delayed fluorescent light emission.

Actually, as illustrated in FIG. 11, the energy gap ($\Delta ST=T_1-S_1$) between an excited singlet state ($S_1$) and an excited triplet state ($T_1$) of exemplary compound A1 is smaller than that of comparative compound 2-a. Therefore, exemplary compound A1 has higher light emission efficiency than comparative compound 2-a.

(6) Due to having a low LUMO level, the stability to oxygen is high, and durability is high.

In the case of organic semiconductor compounds having similar band gaps, those having lower HOMO-LUMO levels (farther from the vacuum level) have higher stability to oxygen. Therefore, lowering the energy level of LUMO increases the stability to oxygen, thus improving the durability of the compound itself and the durability of an organic light-emitting element.

Thus, the inventors focused on LUMO. Table 1 collectively shows the molecular structure and the molecular orbital calculation results ($S_1$, $T_1$, $\Delta ST$, and LUMO) of exemplary compounds A1, B1, and C1, which are examples of compounds represented by general formula [1-1], comparative compound 1-a, and reference compound D1. As shown in Table 1, it was found that the LUMO levels of compounds A1, B1, and C1 according to this embodiment were lower (farther from the vacuum level) than that of comparative compound 1-a.

To achieve a lower LUMO level, it is necessary to withdraw electrons in the LUMO orbital to increase stability.

However, as in comparative compound 1-a, an electron-donating amino group is bonded immediately adjacent to the anthracenone moiety contributing to LUMO. Thus, the LUMO level becomes higher under the influence of the electron-donating properties of the amino group. By contrast, it was found that in the compound of the present disclosure, since the amine moiety contributing to HOMO has a fused-ring structure, electron donation to the anthracenone moiety contributing to LUMO is inhibited, thus stabilizing LUMO. Therefore, the compound according to this embodiment has a low LUMO level and thus has high stability to oxygen, resulting in high element durability.

TABLE 1

| | Molecular structure | $S_1$ (calc.) [nm] | $T_1$ (calc.) [nm] | $\Delta ST$ (calc.) [nm] | LUMO (calc.) [eV] |
|---|---|---|---|---|---|
| Comparative compound 1-a | 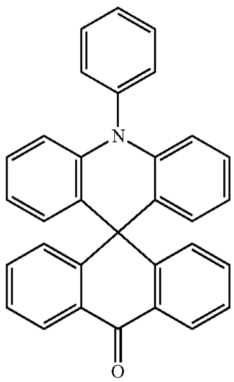 [SMILES: O=C1c2ccccc2C2(c3ccccc31)c1ccccc1N(c1ccccc1)c1ccccc12] | 435 | 439 | 4 | −1.69 |
| A1 | 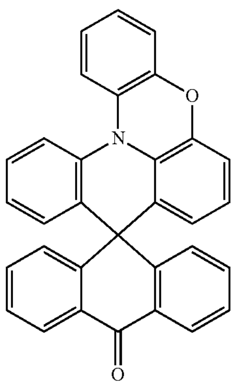 [SMILES: O=C1c2ccccc2C2(c3ccccc31)c1ccccc1N1c3ccccc3Oc3cccc2c31] | 461 | 464 | 3 | −1.82 |
| B1 | 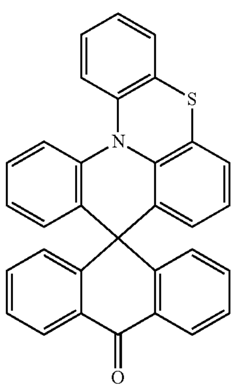 [SMILES: O=C1c2ccccc2C2(c3ccccc31)c1ccccc1N1c3ccccc3Sc3cccc2c31] | 432 | 435 | 3 | −1.85 |
| C1 | 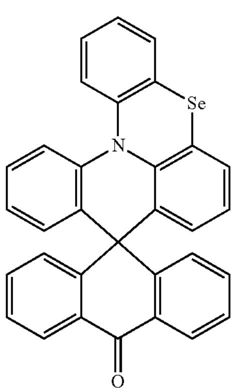 [SMILES: O=C1c2ccccc2C2(c3ccccc31)c1ccccc1N1c3ccccc3[Se]c3cccc2c31] | 432 | 436 | 4 | −1.76 |
| Reference compound D1 | 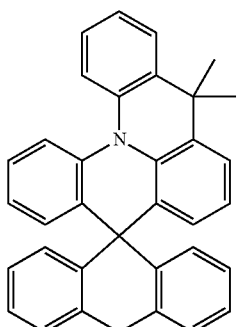 | 426 | 430 | 4 | −1.84 |

Furthermore, the compound according to this embodiment may be used in a light-emitting layer in an organic light-emitting element. In this case, the compound has the following features.

(7) When the compound according to this embodiment is mixed with a host material in a light-emitting layer, the compound according to this embodiment tends to undergo exciton recombination, thus providing a light-emitting element with high efficiency.

(8) When the compound according to this embodiment is mixed with a host material in a light-emitting layer and the light-emitting layer further contains a light-emitting material, a light-emitting element having high efficiency and high color purity is provided.

(9) When the light-emitting material is a hydrocarbon compound, a light-emitting element having high efficiency and good durability is provided.

Hereinafter, the features (7) to (9) will be described.

(7) When the compound according to this embodiment is mixed with a host material in a light-emitting layer, the compound according to this embodiment tends to undergo exciton recombination, thus providing a light-emitting element with high efficiency.

The compound according to this embodiment is a compound having an electron-withdrawing carbonyl group and an electron-donating amino group. Thus, when the compound according to this embodiment is mixed with a host material (second organic compound) in a light-emitting layer of an organic light-emitting element, the light-emitting layer becomes an electron-trapping light-emitting layer due to the contribution of the electron-withdrawing properties or becomes a hole-trapping light-emitting layer due to the contribution of the electron-donating properties.

Therefore, electrons or holes supplied from a transport layer in the light-emitting layer are trapped by the compound according to this embodiment, and exciton recombination occurs. As described in feature (5) above, the compound according to this embodiment has a small energy difference ($\Delta ST$) between $S_1$ and $T_1$, and thus can efficiently produce delayed fluorescent light emission in the light-emitting layer and use more triplet excitons for light emission.

In particular, when the host material is a hydrocarbon compound, the LUMO level of the compound according to this embodiment tends to be lower (farther from the vacuum level) than that of the host material, or the HOMO level of the compound according to this embodiment tends to be higher (closer to the vacuum level) than that of the host material. Thus, electrons or holes are more readily trapped, thus producing a greater effect. Here, the hydrocarbon compound is a compound whose molecule consists of carbon and hydrogen.

Furthermore, the compound according to this embodiment has a spiro moiety and has a basic skeleton having an asymmetric structure and a fused-ring structure as described in (4), and thus is less likely to undergo molecular association and cause concentration quenching in the host material. This effect leads to prevention of quenching due to interaction between excitons when the compound according to this embodiment is in an excited state, and is effective in efficiently producing delayed fluorescent light emission in the light-emitting layer.

(8) When the compound according to this embodiment is mixed with a host material in a light-emitting layer and the light-emitting layer further contains a light-emitting material, a light-emitting element having high efficiency and high color purity is provided.

By using the compound according to this embodiment in a light-emitting layer and further doping the light-emitting layer with a light-emitting material with a high emission quantum yield or light-emitting material having an emission spectrum suitable for exhibiting high color purity (third organic compound), a light-emitting element having even higher efficiency and higher color purity is provided. Here, the compound according to this embodiment functions as an assist material. In this case, to facilitate exciton recombination, the compound according to this embodiment may be contained at such a concentration that allows electrons or holes to be preferentially trapped in the light-emitting layer. Thus, the concentration of the organic compound according to this embodiment is preferably 0.1 mass % or more and 45 mass % or less, more preferably 1 mass % or more and 30 mass % or less, relative to the total mass of the light-emitting layer.

When the compound according to this embodiment is considered as a light-emitting material, the doping concentration may be smaller to reduce the influence of concentration quenching due to interaction between molecules and a change in emission spectrum. Thus, the light-emitting layer may be doped with a light-emitting material in addition to the compound according to this embodiment. The doping concentration of the light-emitting material in the light-emitting layer is preferably 0.01 mass % or more and 20 mass % or less, more preferably 1 mass % or more and 15 mass % or less, relative to the total mass of the light-emitting layer. For the above reasons, a light-emitting element having high efficiency and high color purity can be provided.

(9) When the light-emitting material is a hydrocarbon compound, a light-emitting element having high efficiency and good durability is provided.

Since the compound according to this embodiment has a strong electron-withdrawing carbonyl group, the light-emitting material used together as a dopant in the light-emitting layer as described in (8) above may be a light-emitting material having no electron-donating amino group, and may be a hydrocarbon compound. The reason for this is as follows. When a light-emitting material having an amino group is used together with the compound according to this embodiment, the amino group and the carbonyl group of the compound according to this embodiment interact with each other in the light-emitting layer. This may cause exciplex formation, thus resulting in a decrease in light emission efficiency, or cause a change in emission spectrum of the light-emitting material, thus resulting in a light-emitting element having lower color purity.

Furthermore, the light-emitting material having an amino group has a low ionization potential and thus is easily oxidized, resulting in low element durability. Thus, the light-emitting material is preferably a hydrocarbon compound, more preferably a fused polycyclic compound having a five-membered ring. This is because such a compound has a structure that has a higher ionization potential and thus is less easily oxidized. Here, the hydrocarbon compound is a compound whose molecule consists of carbon and hydrogen.

For the above reasons, mixing the compound according to this embodiment with a host material in a light-emitting layer can provide an organic light-emitting element that emits light with high efficiency. Here, the compound according to this embodiment may be used as a light-emitting material. Alternatively, the compound according to this embodiment may function as an assist material, with another light-emitting material being further mixed in addition to the compound according to this embodiment. By using a light-emitting material having good color purity, an organic light-emitting element having high efficiency and high color purity can be obtained. Furthermore, when the host material is a hydrocarbon compound, the compound according to this embodiment can easily trap electrons and holes, thus providing higher efficiency.

Next, more preferred compounds represented by general formula [1-1] will be described.

A compound represented by general formula [1-1] where X is an oxygen atom has an $S_1$ energy value suitable for a green light-emitting material. In other words, a compound represented by general formula [2-1] below is preferred. As shown in Table 1, exemplary compound A1, which is a compound represented by general formula [2-1] below where $R_1$ to $R_{18}$ are each a hydrogen atom, has an $S_1$ energy value of 461 nm and exhibits green light emission.

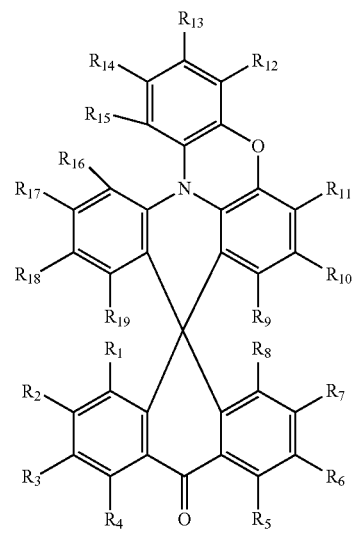

[2-1]

In general formula [2-1], $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group.

In general formula [2-1], $R_1$ to $R_{18}$ may each independently be selected from the group consisting of a hydrogen atom, a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aromatic hydrocarbon group having 6 to 60 carbon atoms, a substituted or unsubstituted heterocyclic group having 3 to 60 carbon atoms, a substituted or unsubstituted aryloxy group, a substituted or unsubstituted silyl group, and a cyano group. Examples of substituents suitable as $R_1$ to $R_{18}$ are as described above.

A compound represented by general formula [1-1] where X is a sulfur atom or a selenium atom has an $S_1$ energy value suitable for a blue light-emitting material. In other words, a compound represented by general formula [2-2] below or general formula [2-3] below is preferred. As shown in Table 1, exemplary compound B1, which is a compound represented by general formula [2-2] below where $R_1$ to $R_{18}$ are each a hydrogen atom, has an $S_1$ energy value of 432 nm and exhibits blue light emission.

Exemplary compound C1, which is a compound represented by general formula [2-3] below where $R_1$ to $R_{18}$ are each a hydrogen atom, has an $S_1$ energy value of 432 nm and exhibits blue light emission.

Furthermore, a compound represented by general formula [1-1] where X is a sulfur atom, that is, a compound represented by general formula [2-2], has a lower LUMO level.

[2-2]

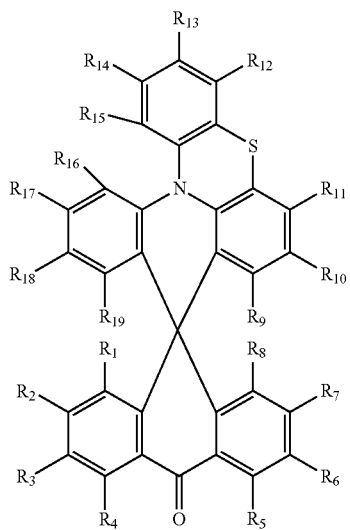

In general formula [2-2], $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group.

In general formula [2-2], $R_1$ to $R_{18}$ may each independently be selected from the group consisting of a hydrogen atom, a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aromatic hydrocarbon group having 6 to 60 carbon atoms, a substituted or unsubstituted heterocyclic group having 3 to 60 carbon atoms, a substituted or unsubstituted aryloxy group, a substituted or unsubstituted silyl group, and a cyano group. Examples of substituents suitable as $R_1$ to $R_{18}$ are as described above.

[2-3]

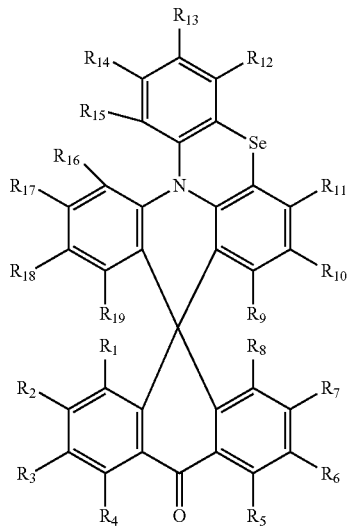

In general formula [2-3], $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group.

In general formula [2-3], $R_1$ to $R_{18}$ may each independently be selected from the group consisting of a hydrogen atom, a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aromatic hydrocarbon group having 6 to 60 carbon atoms, a substituted or unsubstituted heterocyclic group having 3 to 60 carbon atoms, a substituted or unsubstituted aryloxy group, a substituted or unsubstituted silyl group, and a cyano group. Examples of substituents suitable as $R_1$ to $R_{18}$ are as described above.

Reference compound D1 in Table 1 is an example of compounds represented by general formula [1-1] where X is replaced with $CR_{19}R_{20}$. Here, $R_{19}$ and $R_{20}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group. $R_{19}$ and $R_{20}$ may each independently be selected from the group consisting of a hydrogen atom, a halogen atom, and a substituted or unsubstituted alkyl group having 1 to 10 carbon atoms. In particular, a compound represented by general formula [2-4] below where $R_{19}$ and $R_{20}$ are each a methyl group is preferred.

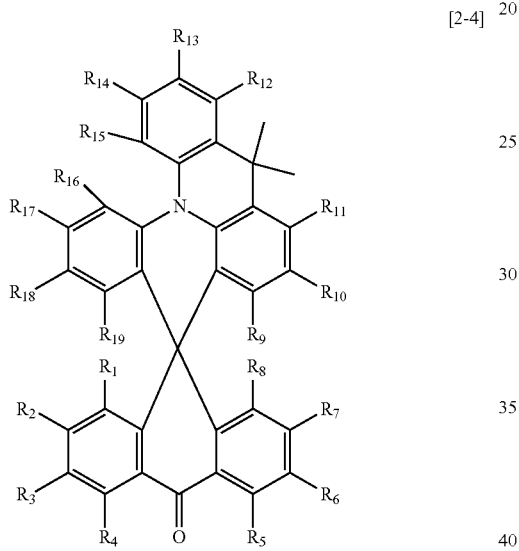

[2-4]

In general formula [2-4], $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group.

In general formula [2-4], $R_1$ to $R_{18}$ may each independently be selected from the group consisting of a hydrogen atom, a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aromatic hydrocarbon group having 6 to 60 carbon atoms, a substituted or unsubstituted heterocyclic group having 3 to 60 carbon atoms, a substituted or unsubstituted aryloxy group, a substituted or unsubstituted silyl group, and a cyano group. Examples of substituents suitable as $R_1$ to $R_{18}$ are as described above.

Specific examples of the organic compound according to the present disclosure will be shown below. However, the present disclosure is not limited to these examples.

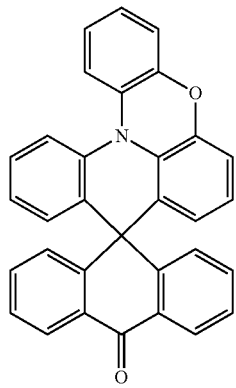
A1

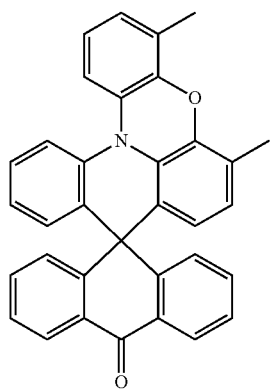
A2

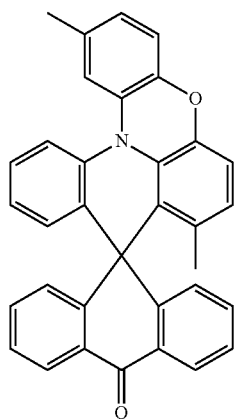
A3

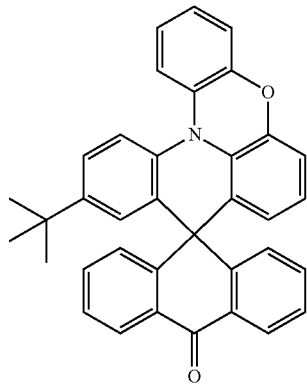
A4

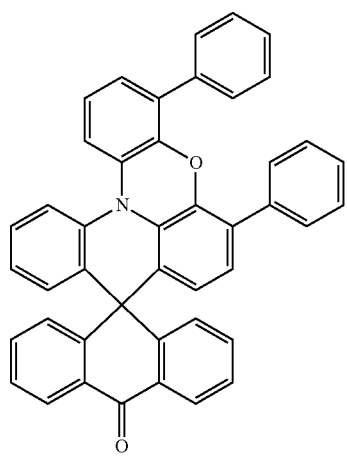
A5
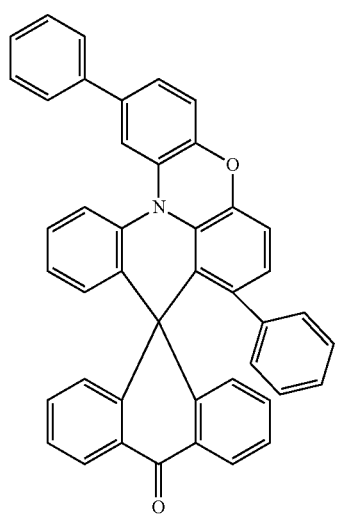
A6
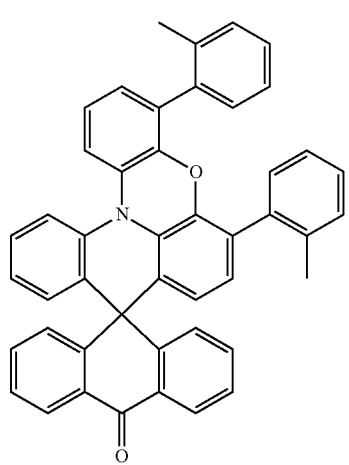
A7
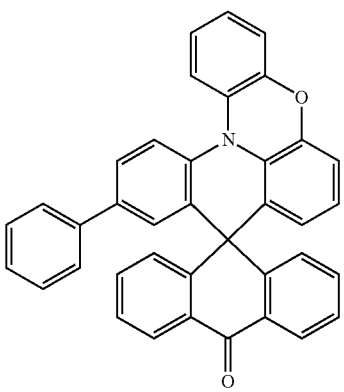
A8
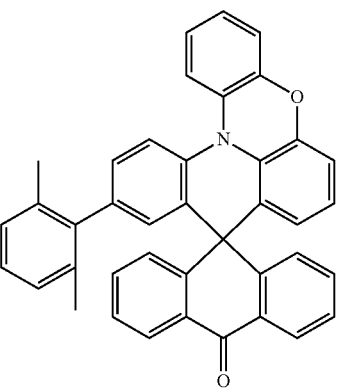
A9
A10

A11
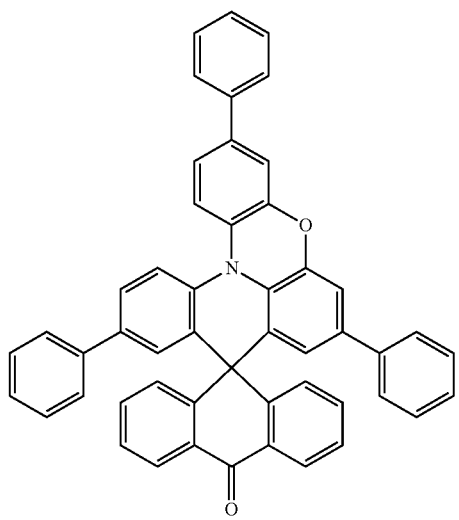
A12
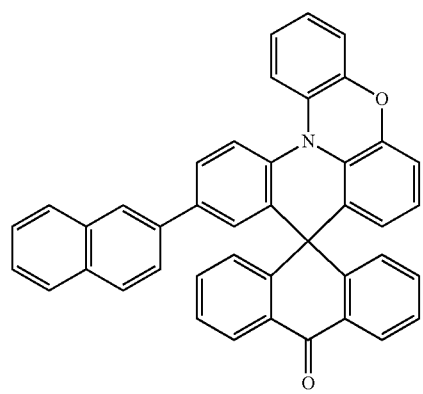
A13
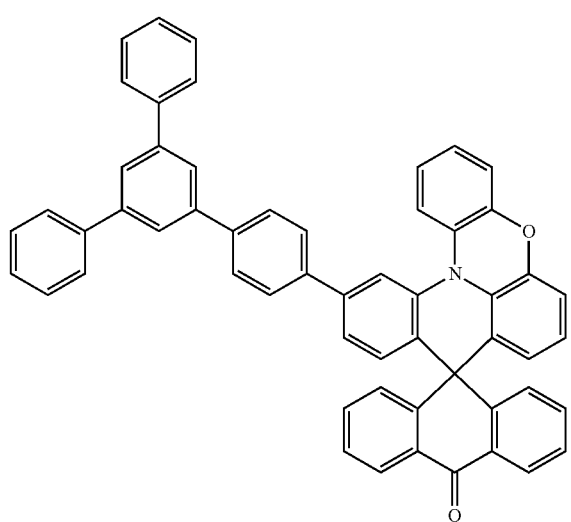
A14
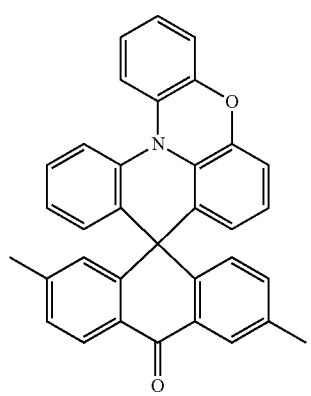
A15
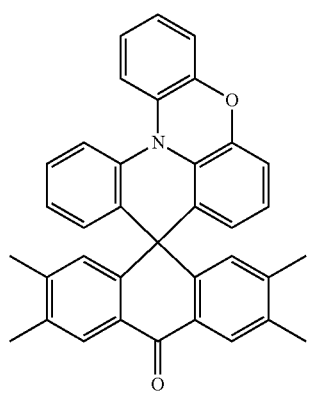
A16
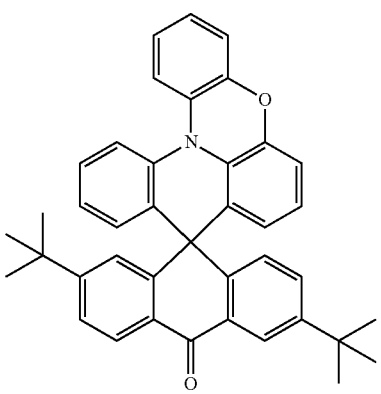
A17
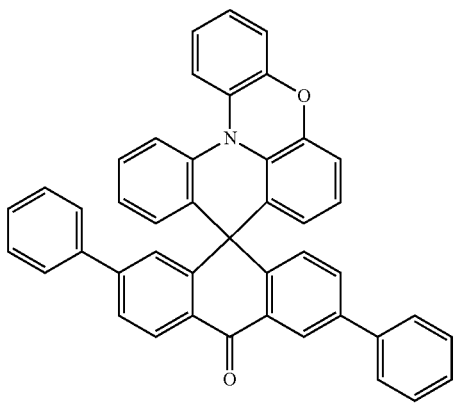

A18
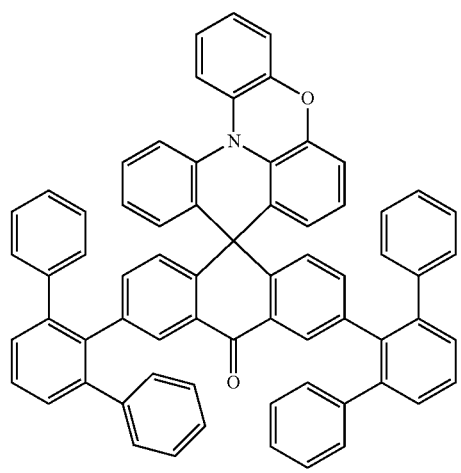
A19
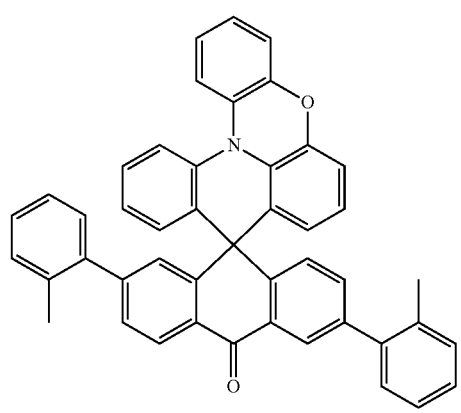
A20
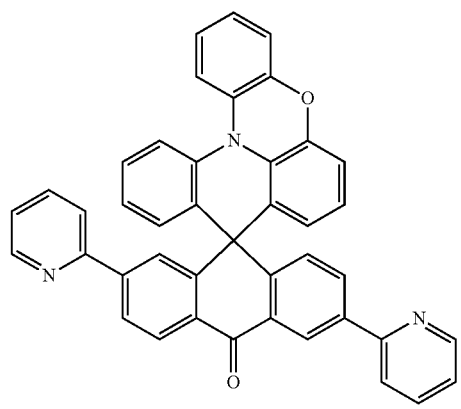
A21
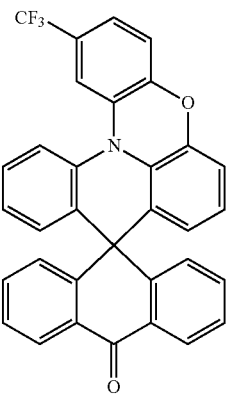
A22
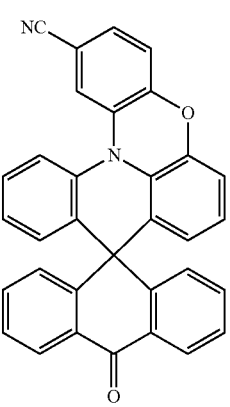
A23
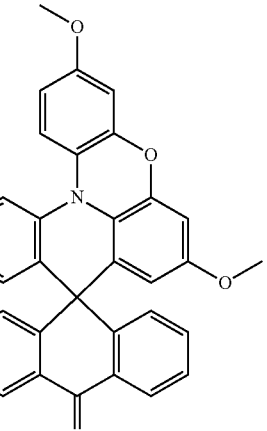
A24

-continued
B1
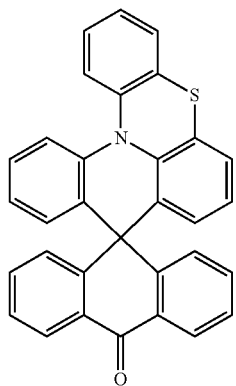
B2
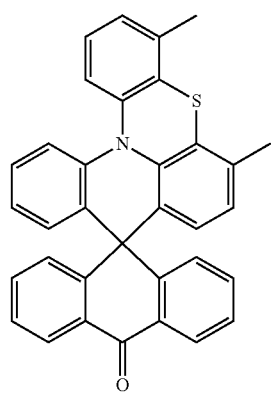
B3
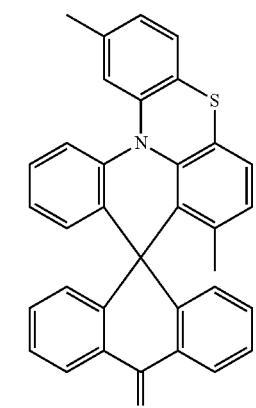
B4
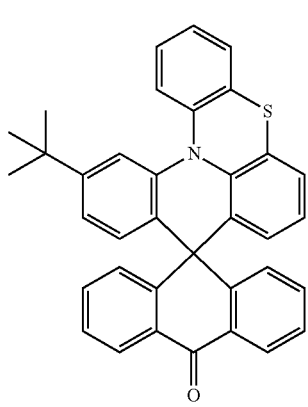
B5
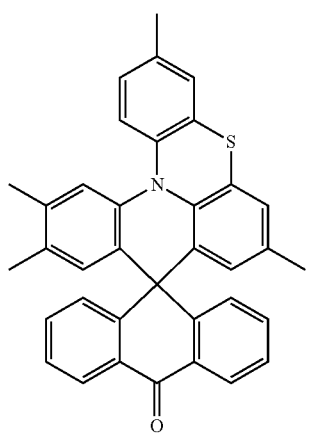
B6
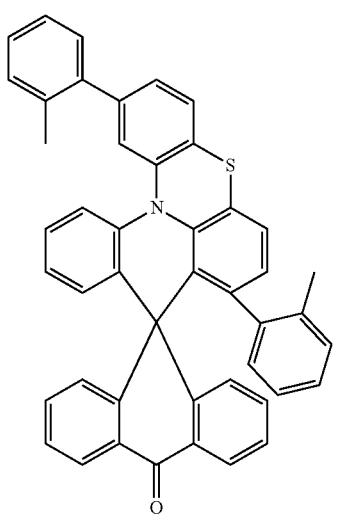
B7
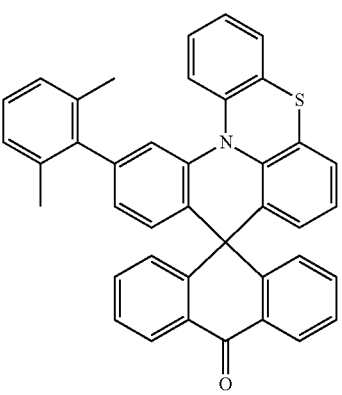

B8
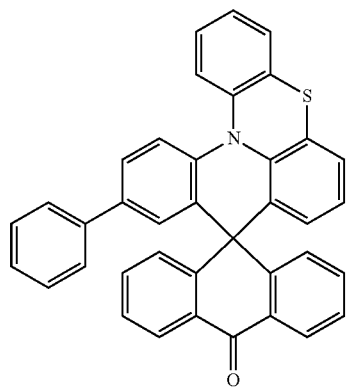
B9
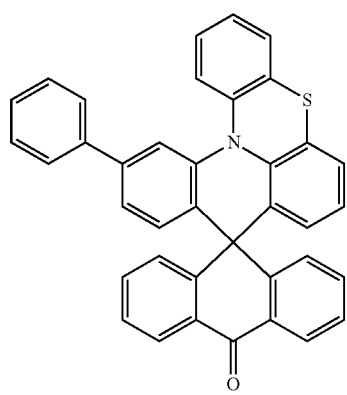
B10
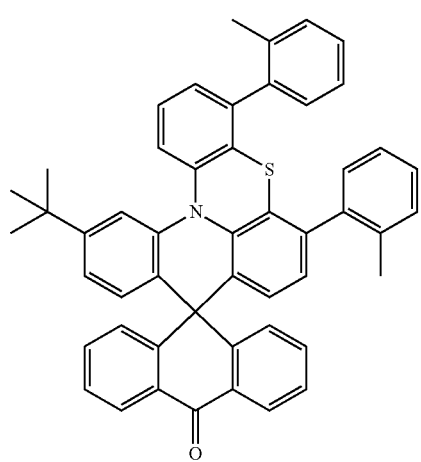
B11
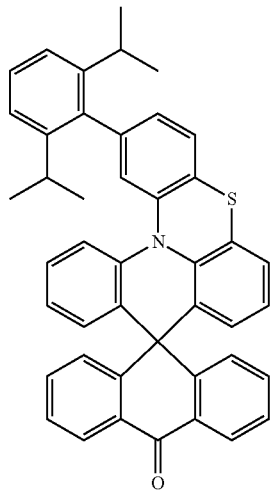
B12
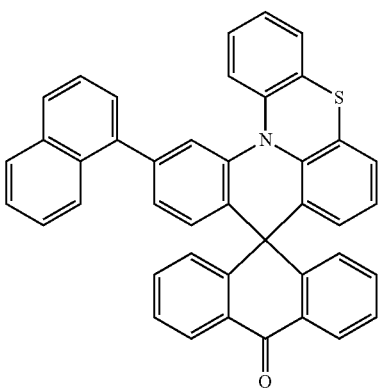
B13
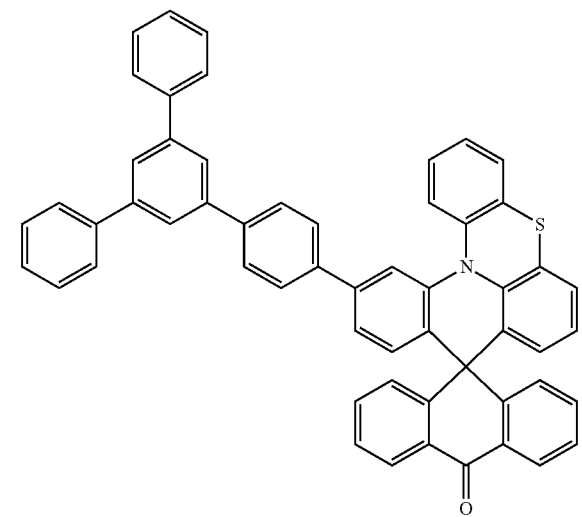

-continued
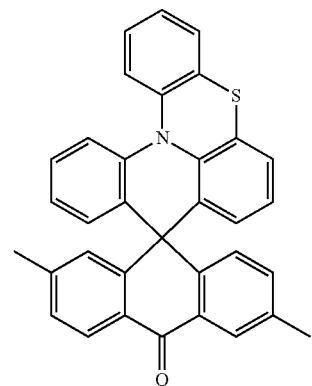
B14
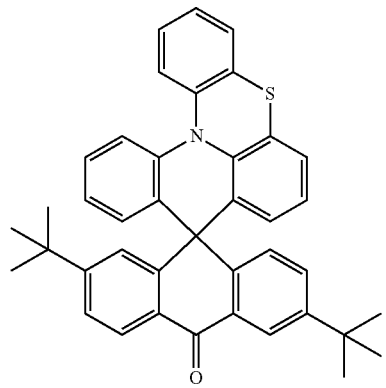
B15
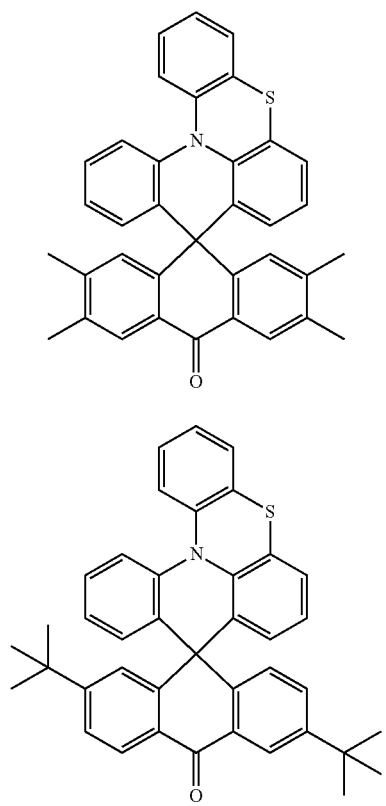
B16
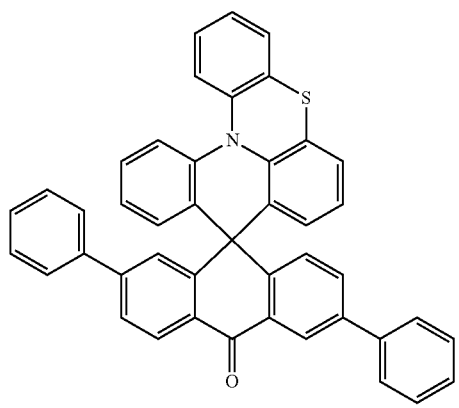
B17
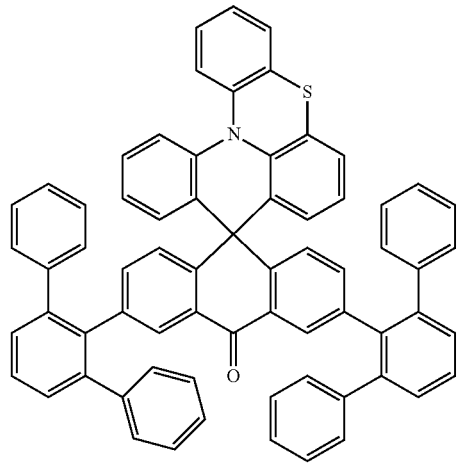
B18
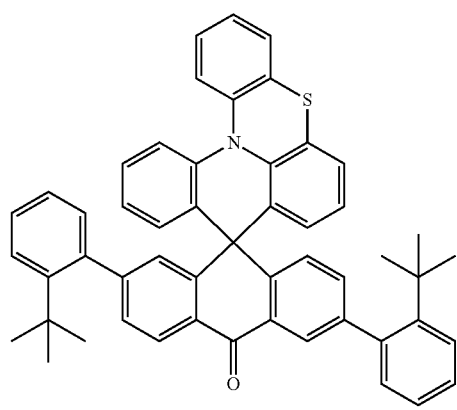
B19
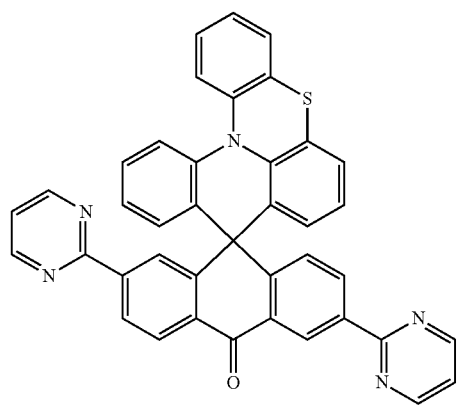
B20

B21 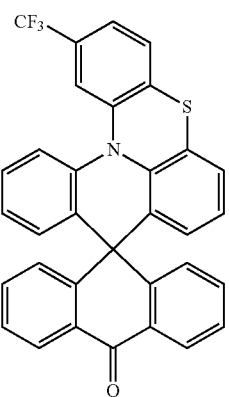
B22 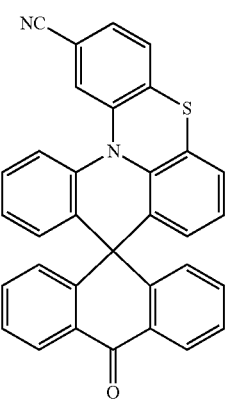
B23 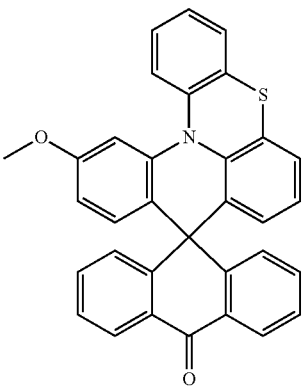
B24 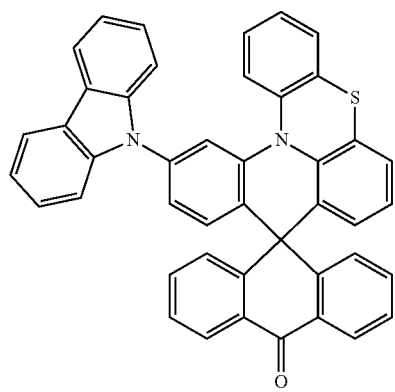
C1 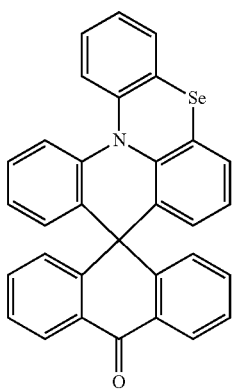
C2 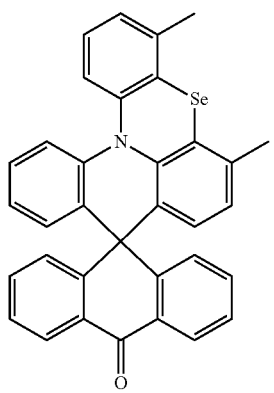
C3 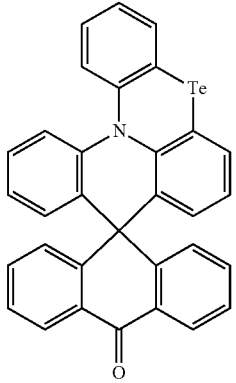
C4 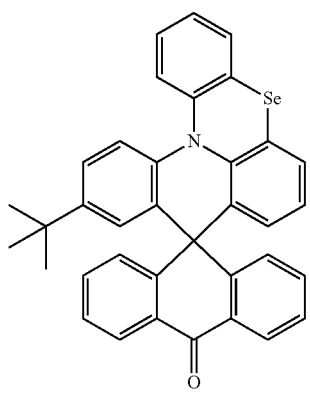

C5
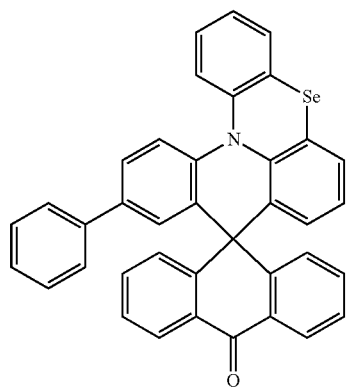
C6
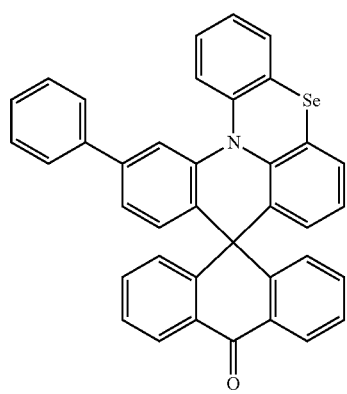
C7
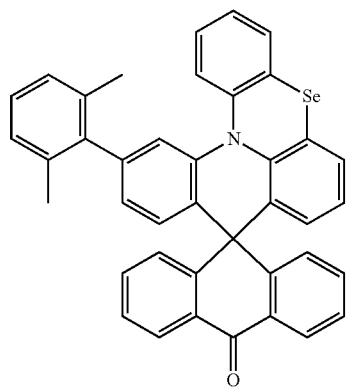
C8
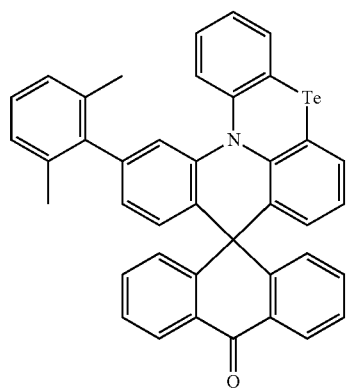
C9
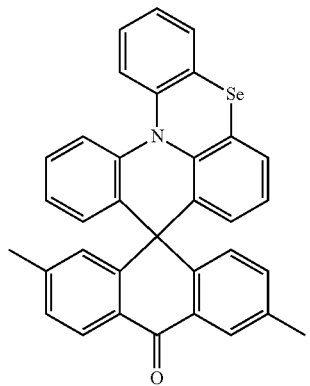
C10
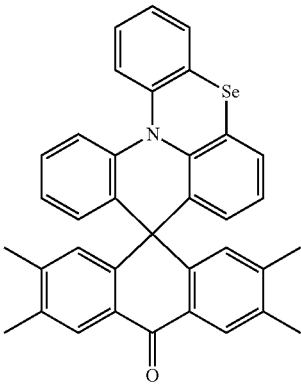
C11
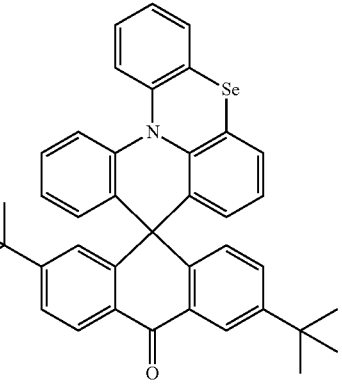
C12
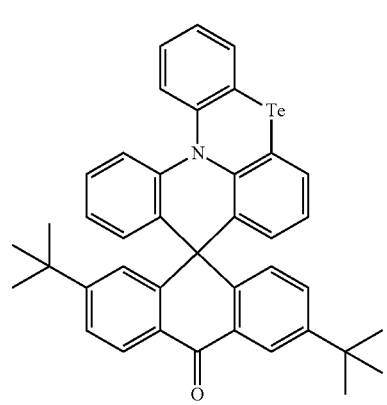
Among the above exemplary compounds, those belonging to group A (compounds A1 to A24) are compounds represented by general formula [1-1] where X is an oxygen atom, that is, compounds represented by general formula [2-1]. These compounds, among compounds represented by general formula [1-1], have smaller $S_1$ energy values as described above and thus can provide green light emission when used, for example, in an organic light-emitting element.

Among the above exemplary compounds, those belonging to group B (compound B1 to B24) are compounds represented by general formula [1-1] where X is a sulfur atom, that is, compounds represented by general formula [2-2]. These compounds, among compounds represented by general formula [1-1], have low LUMO levels as described above and thus can provide good durability when used, for example, in an organic light-emitting element.

Among the above exemplary compounds, those belonging to group C (C1 to C12) are compounds represented by general formula [1-1] where X is a selenium atom (C1 to C11) or a tellurium atom (C12). These compounds, among compounds represented by general formula [1-1], have larger $S_1$ energy values as described above and thus can provide blue light emission when used, for example, in an organic light-emitting element.

The compound according to this embodiment has, in its basic skeleton, a chalcogen atom having an unshared electron pair. This unshared electron pair has the effect of increasing the structural stability of the fused basic skeleton. Therefore, the compound according to this embodiment has high stability and high durability, and when the compound according to this embodiment is used in an organic light-emitting element, the organic light-emitting element can be provided with good durability.

For reference, specific examples of organic compounds represented by general formula [2-4] are shown below.

D1
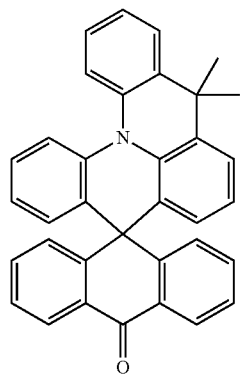

D2
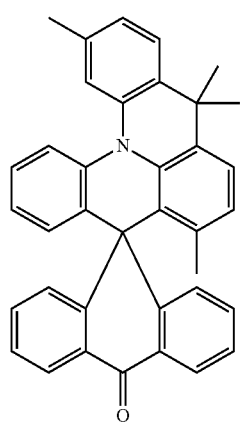

D3
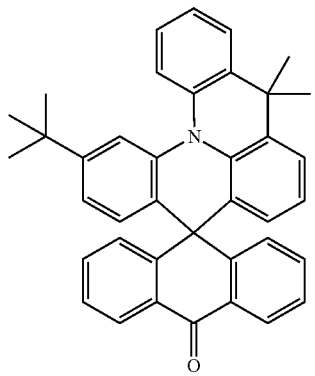

D4
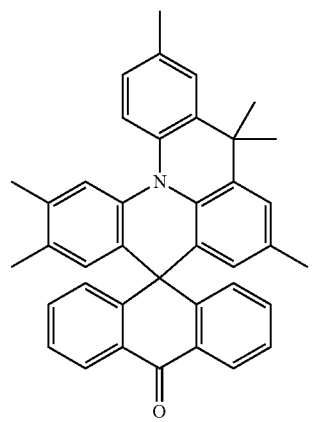

D5
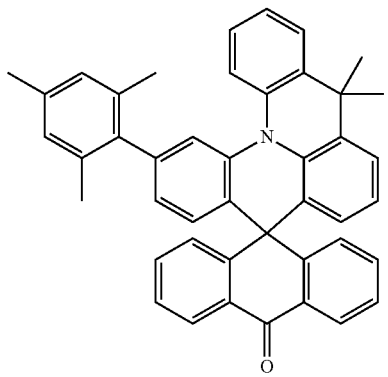

D6
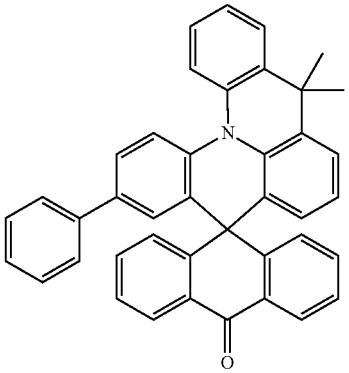

-continued
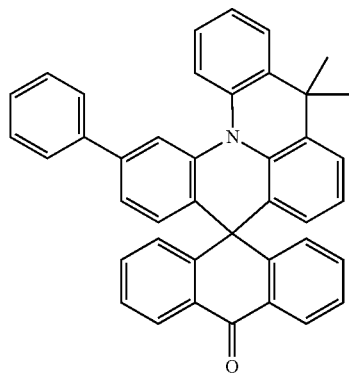
D7
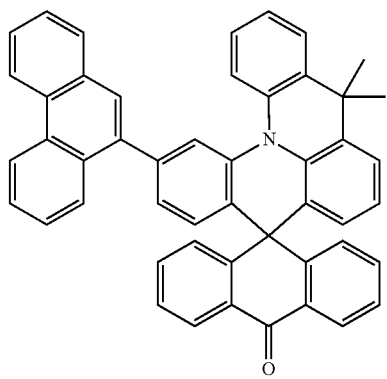
D8
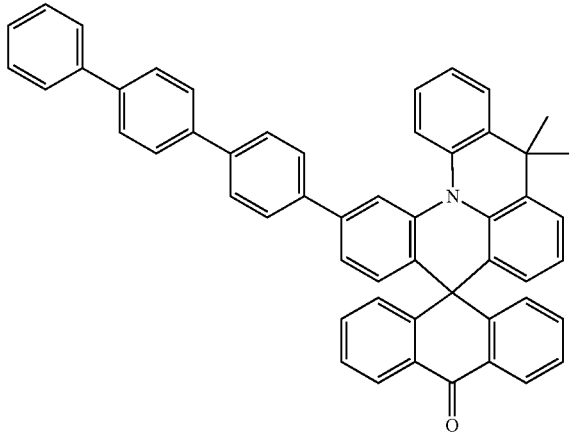
D9
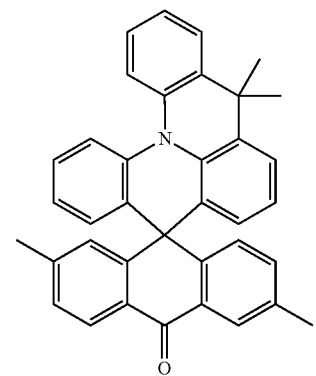
D10
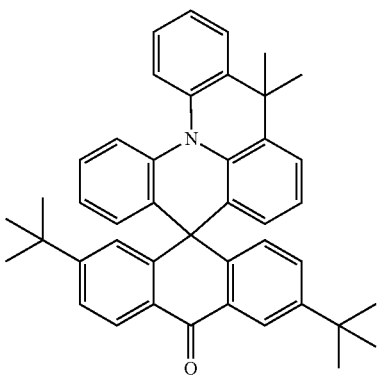
D11
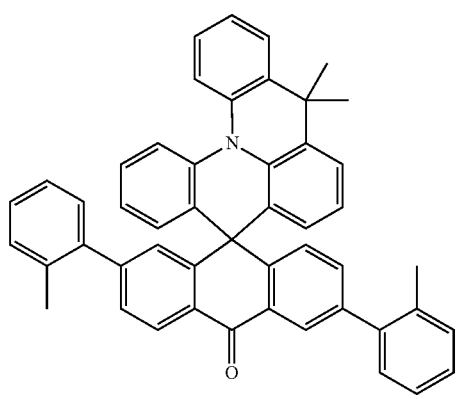
D12
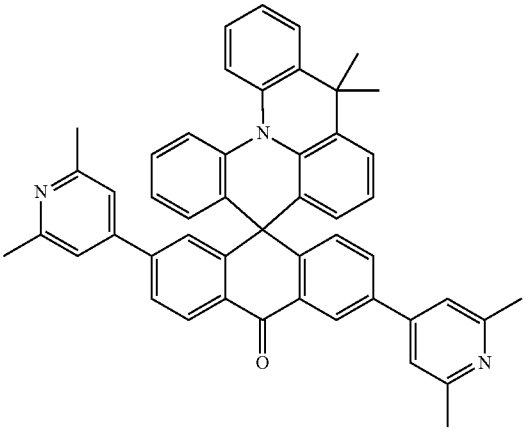
D13
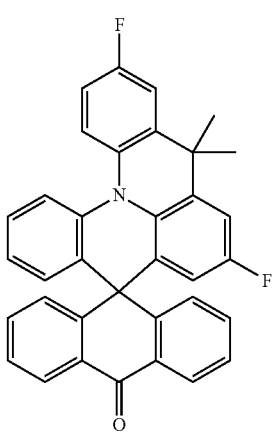
D14

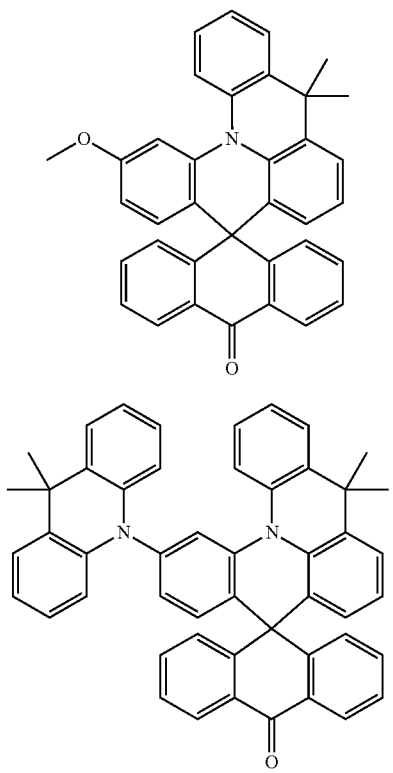

Among the above exemplary compounds, those belonging to group D (D1 to D16) are compounds represented by general formula [2-4]. These compounds have a molecular structure represented by general formula [1-1] where X is replaced with a substituent (here, an alkyl group) that is more sterically bulky than chalcogen atoms. Thus, these compounds are less likely to undergo molecular association and less likely to undergo intermolecular packing, thus providing highly efficient light emission.

Organic Light-Emitting Element

Next, an organic light-emitting element according to an embodiment will be described.

The organic light-emitting element according to this embodiment at least includes a pair of electrodes, that is, an anode and a cathode, and an organic compound layer disposed between these electrodes. In the organic light-emitting element according to this embodiment, the organic compound layer may be a single layer or a laminate of a plurality of layers as long as the organic compound layer includes a light-emitting layer.

When the organic compound layer is a laminate of a plurality of layers, the organic compound layer may include, in addition to the light-emitting layer, a hole injection layer, a hole transport layer, an electron blocking layer, a hole/exciton blocking layer, an electron transport layer, an electron injection layer, and other layers. The light-emitting layer may be a single layer or a laminate of a plurality of layers.

In the organic light-emitting element according to this embodiment, at least one organic compound layer contains the organic compound according to this embodiment. Specifically, the organic compound according to this embodiment is contained in any of the light-emitting layer, the hole injection layer, the hole transport layer, the electron blocking layer, the light-emitting layer, the hole/exciton blocking layer, the electron transport layer, the electron injection layer, and the other layers described above. The organic compound according to this embodiment may be contained in the light-emitting layer.

In the organic light-emitting element according to this embodiment, when the organic compound according to this embodiment is contained in the light-emitting layer, the light-emitting layer may be a layer formed only of the organic compound according to this embodiment or a layer formed of the organic compound according to this embodiment and other compounds. When the light-emitting layer is a layer formed of the organic compound according to this embodiment and other compounds, the organic compound according to this embodiment may be used as a host or guest of the light-emitting layer. The organic compound may also be used as an assist material that can be contained in the light-emitting layer. As used herein, the term "host" refers to a compound accounting for the largest mass proportion among the compounds constituting the light-emitting layer. The term "guest" refers to a compound that accounts for a lower mass proportion than the host among the compounds constituting the light-emitting layer and that mainly contributes to light emission. The term "assist material" refers to a compound that accounts for a lower mass proportion than the host among the compounds constituting the light-emitting layer and that assists the light emission of the guest.

When the organic compound according to this embodiment is used as a guest of the light-emitting layer, the concentration of the guest is preferably 0.01 mass % or more and 20 mass % or less, more preferably 0.1 mass % or more and 5 mass % or less, relative to the total mass of the light-emitting layer. When the organic compound according to this embodiment is used as an assist material of the light-emitting layer, the concentration of the assist material is preferably 0.1 mass % or more and 45 mass % or less, more preferably 1 mass % or more and 30 mass % or less, relative to the total mass of the light-emitting layer.

When the organic compound according to this embodiment is used as a guest material of the light-emitting layer, the mass ratio (host material/guest material) of the host material (second organic compound) to the organic compound according to this embodiment serving as the guest material is preferably 1.1 or more and 10000 or less. Furthermore, this mass ratio is more preferably 2 or more and 1000 or less, still more preferably 2 or more and 100 or less.

When the organic compound according to this embodiment is used as a guest of the light-emitting layer, a material that has a higher LUMO level than the organic compound according to this embodiment (a material having a LUMO level closer to the vacuum level) may be used as a host (second organic compound). The organic compound according to this embodiment tends to have a low LUMO level. Thus, by using a material that has a higher LUMO level than the organic compound according to this embodiment as a host, the organic compound according to this embodiment can accept more electrons supplied to the host of the light-emitting layer. When the organic compound according to this embodiment is used as a guest material of the light-emitting layer, the following relationship may be satisfied. When the energy of $S_1$ (singlet energy) of the host material is $S_{h1}$, the energy of $T_1$ (triplet energy) of the host material is $T_{h1}$, the energy of $S_1$ (singlet energy) of the guest material is $S_{g1}$, and the energy of $T_1$ (triplet energy) of the guest material is $T_{g1}$, $S_{h1} > S_{g1}$ may be satisfied, and furthermore, $T_{h1} > T_{g1}$ may be satisfied.

When the organic compound according to this embodiment is used as an assist material of the light-emitting layer, a material that has a higher LUMO level than the organic compound according to this embodiment (a material having a LUMO level closer to the vacuum level) may be used as a guest (third organic compound). The organic compound according to this embodiment tends to have a low LUMO level. Thus, by using a material that has a higher LUMO level than the organic compound according to this embodiment as a light-emitting material (guest), the organic compound according to this embodiment accepts more electrons supplied to the host of the light-emitting layer, and the assist material contributes to exciton recombination. This enables efficient energy transfer to the light-emitting material (guest). When the organic compound according to this embodiment is used as an assist material of the light-emitting layer, a material whose energy of $S_1$ (singlet energy) is lower than that of the organic compound according to this embodiment may be used as a guest material (light-emitting material). When the energy of $S_1$ (singlet energy) of the assist material is $S_{a1}$, the energy of $T_1$ (triplet energy) of the assist material is $T_{a1}$, the energy of $S_1$ (singlet energy) of the guest material is $S_{g1}$, and the energy of $T_1$ (triplet energy) of the guest material is $T_{g1}$, $S_{a1} > S_{g1}$ may be satisfied. Furthermore, $T_{a1} > T_{g1}$ may be satisfied. Furthermore, when the energy of $S_1$ (singlet energy) of the host material is $S_{h1}$, and the energy of $T_1$ (triplet energy) of the host material is $T_{h1}$, $S_{h1} > S_{a1} > S_{g1}$ may be satisfied. Furthermore, $T_{h1} > T_{a1} > T_{g1}$ may be satisfied.

The present inventors have conducted various studies and found that when the organic compound according to this embodiment is used as a host, a guest, or an assist material of a light-emitting layer, particularly, as a guest of a light-emitting layer, an element that outputs light with high efficiency and high luminance and has very high durability can be provided. The inventors have further found that when the organic compound according to this embodiment is used as an assist material of a light-emitting layer, an element that outputs light with high efficiency and high luminance and has very high durability can be provided. This light-emitting layer may have a single-layer structure or a multilayer structure, and may contain a plurality of light-emitting materials. The multilayer structure may be a state in which a light-emitting layer and another light-emitting layer are stacked on top of each other or a state in which an intermediate layer is stacked between a plurality of light-emitting layers. The element may emit fluorescent light or phosphorescent light. The element may be a tandem element or a stacked element. In these cases, the emission color of the organic light-emitting element is not limited to single colors. More specifically, the emission color may be white or an intermediate color. The method of film formation is not particularly limited, and the film formation is performed by vapor deposition or coating. Details thereof will be described in EXAMPLES given later.

The organic compound according to this embodiment can be used as a constituent material of an organic compound layer other than the light-emitting layer constituting the organic light-emitting element according to this embodiment. Specifically, the organic compound may be used as a constituent material of, for example, the electron transport layer, the electron injection layer, the hole transport layer, the hole injection layer, or the hole blocking layer.

Materials Constituting Organic Light-Emitting Element

In addition to the organic compound according to this embodiment, various low-molecular-weight and high-molecular-weight compounds known in the art may optionally be used as materials constituting the organic light-emitting element. Typically, for example, a hole injection compound or hole transport compound, a compound serving as a host, a luminescent compound, and an electron injection compound or electron transport compound may be used in combination. Examples of these compounds will be described below.

As a hole injection/transport material (hole injection material or hole transport material), a material that facilitates injection of holes from the anode and that have so high hole mobility that enables injected holes to be transported to the light-emitting layer may be used. To prevent deterioration of film quality, such as crystallization, in the organic light-emitting element, a material having high a glass-transition temperature may be used. Examples of low-molecular-weight and high-molecular-weight materials having hole injection/transport properties include triarylamine derivatives, arylcarbazole derivatives, phenylenediamine derivatives, stilbene derivatives, phthalocyanine derivatives, porphyrin derivatives, poly(vinylcarbazole), poly(thiophene), and other conductive polymers. These hole injection/transport materials are also suitable for use in the electron blocking layer.

Non-limiting specific examples of compounds usable as hole injection/transport materials are shown below.

HT1

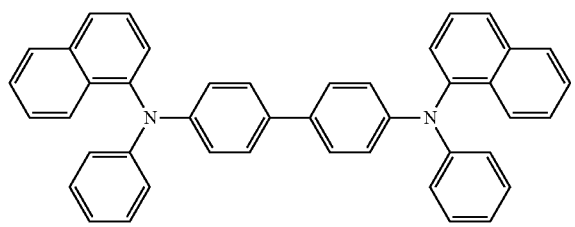

HT2

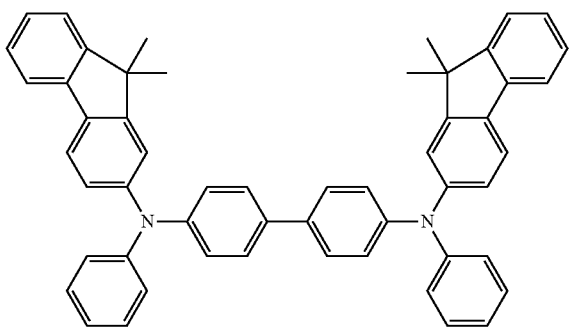

-continued
HT3
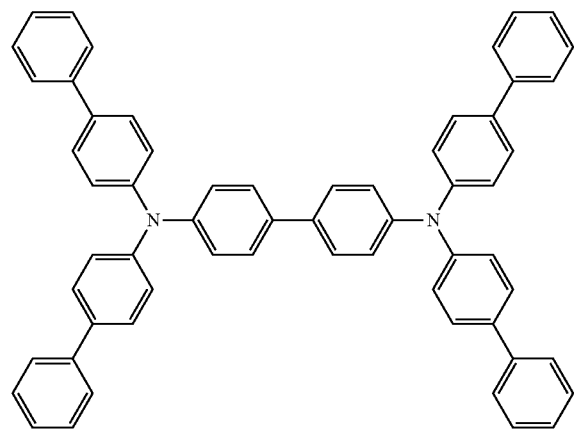
HT4
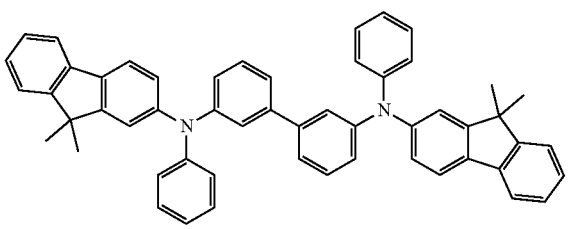
HT5
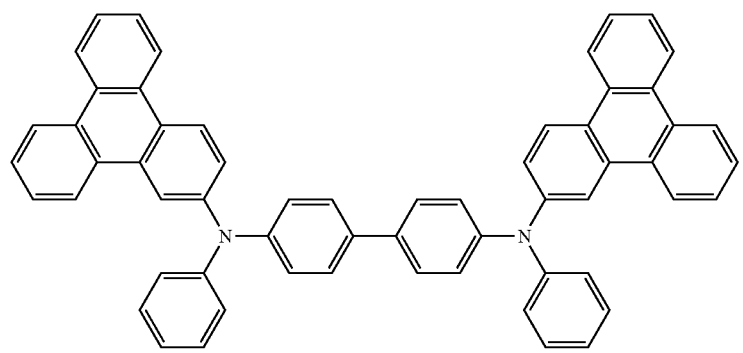
HT6
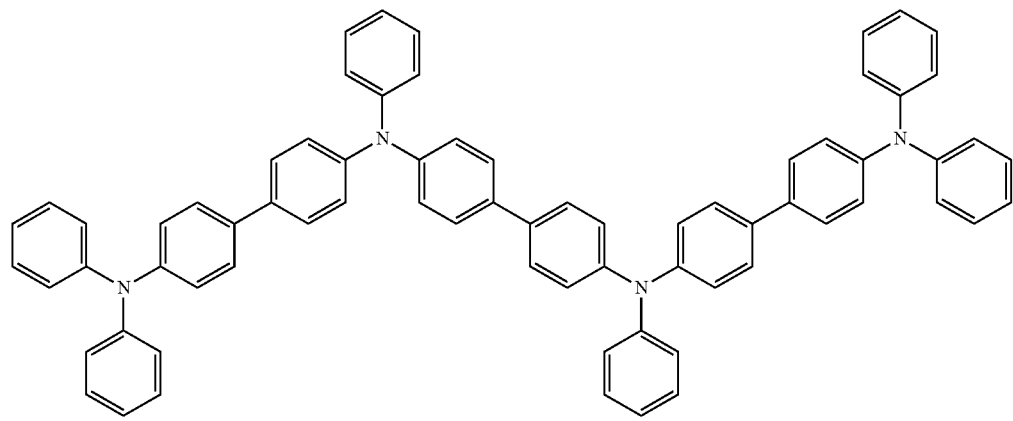

-continued
HT7
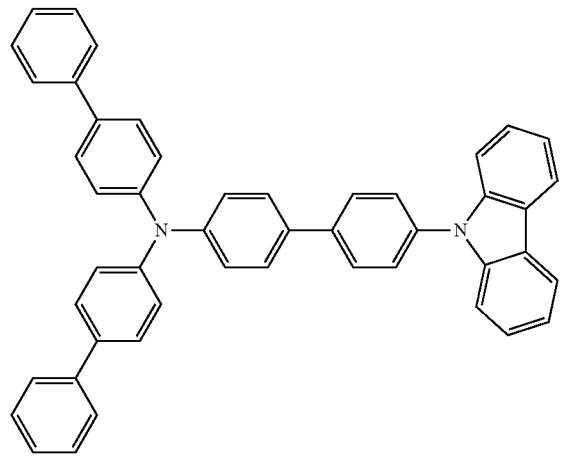
HT8
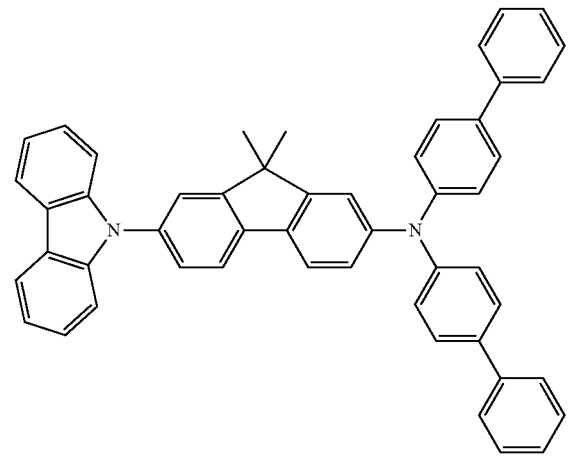
HT9
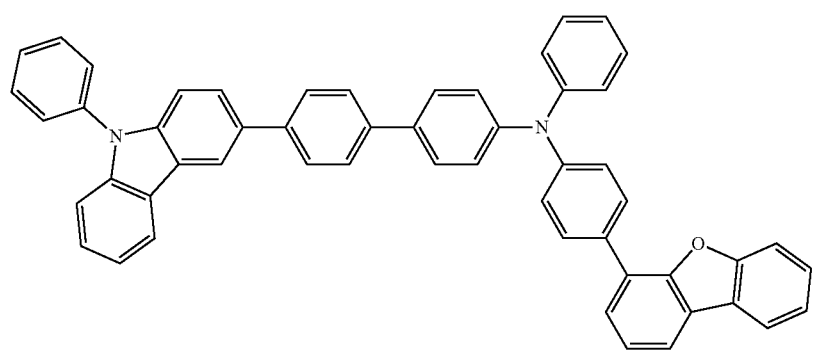
HT10
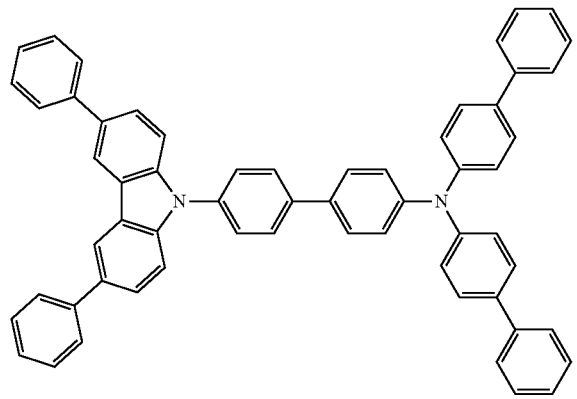
HT11
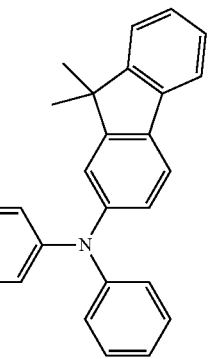
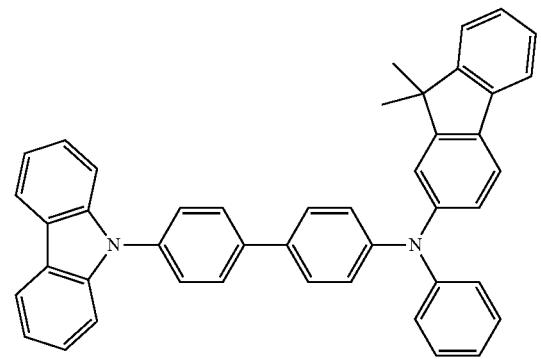
HT12
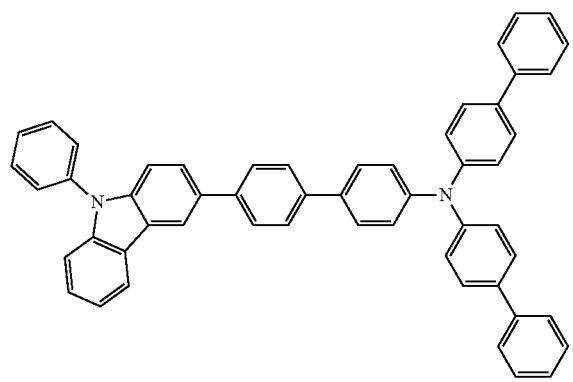
HT13
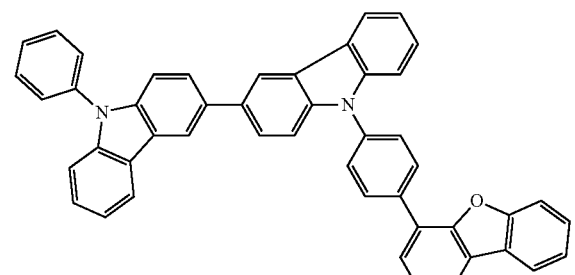

-continued

HT14

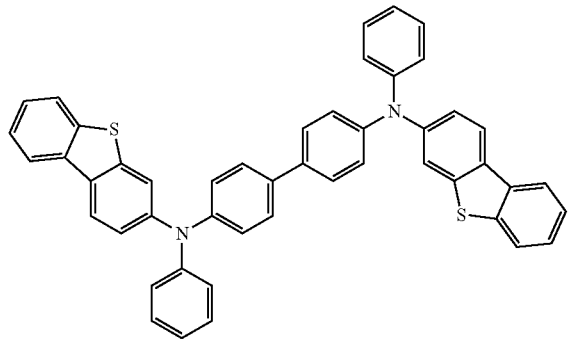

HT15

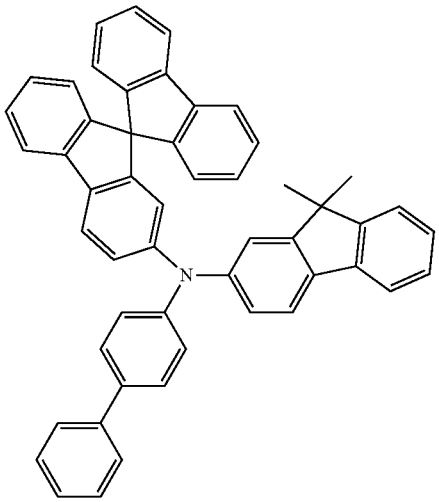

HT16

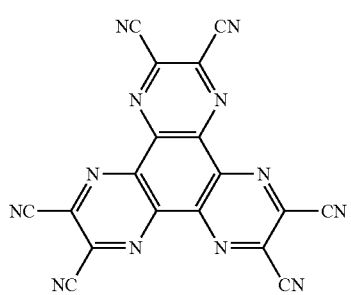

HT17

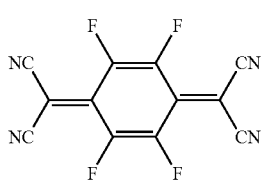

HT18

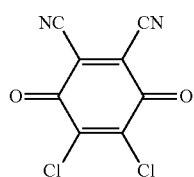

HT19

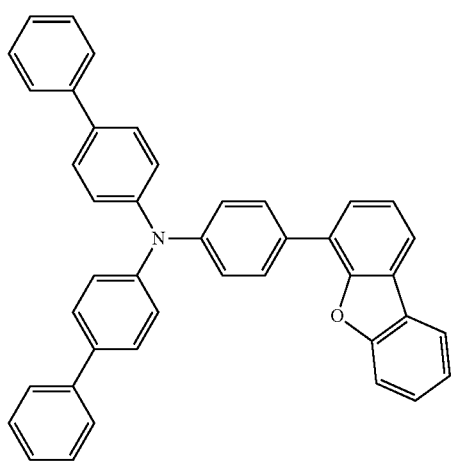

Among the hole injection/transport materials given above, HT16 to HT18 can be used for a layer in contact with the anode to achieve a lower driving voltage. HT16 is widely used in organic light-emitting elements. HT2, HT3, HT4, HT5, HT6, HT10, and HT12 may be used for an organic compound layer adjacent to HT16. A plurality of materials may be used for one organic compound layer.

Examples of light-emitting materials mainly contributing to the light-emitting function include, in addition to the organic compound represented by general formula [1-1], fused-ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organic aluminum complexes such as tris(8-quinolinolato)aluminum, iridium complexes, platinum complexes, rhenium complexes, copper complexes, europium complexes, ruthenium complexes, and polymer derivatives such as poly(phenylenevinylene) derivatives, poly(fluorene) derivatives, and poly(phenylene) derivatives.

Non-limiting specific examples of compounds usable as light-emitting materials are shown below.

BD1
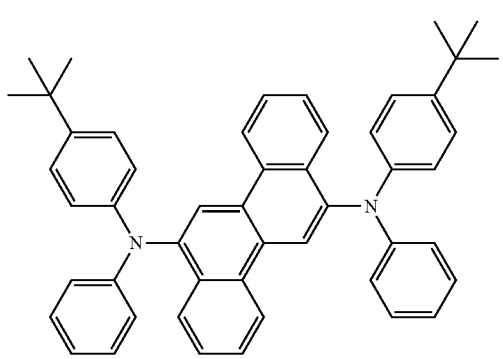
BD5
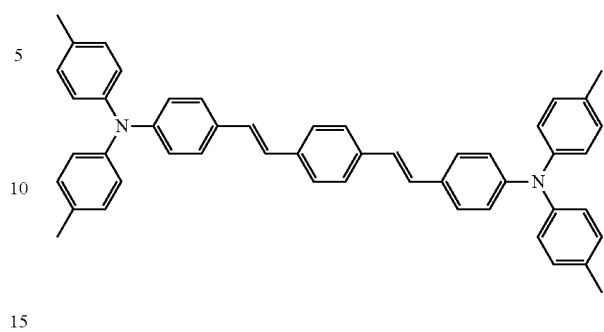
BD2
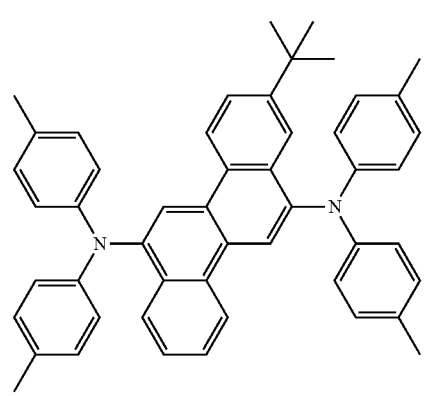
BD6
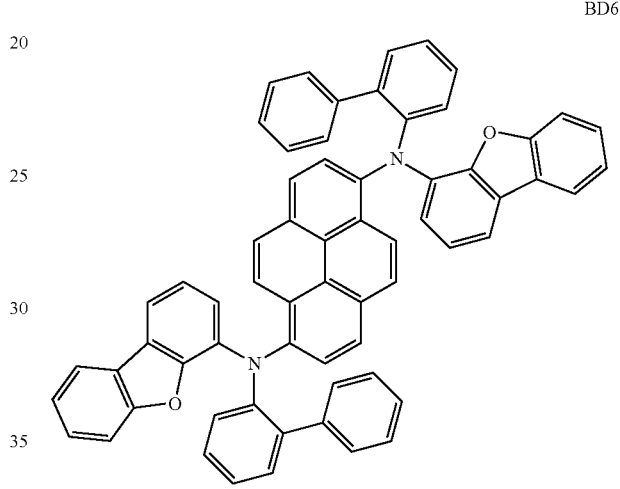
BD3
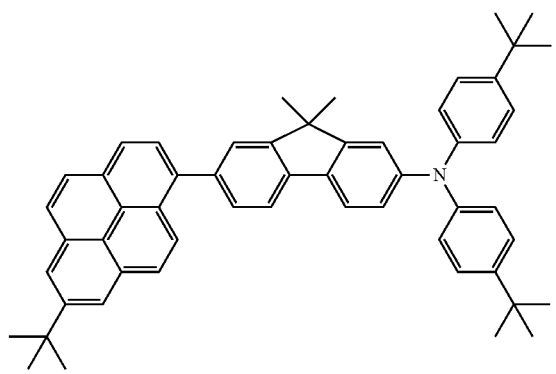
BD7
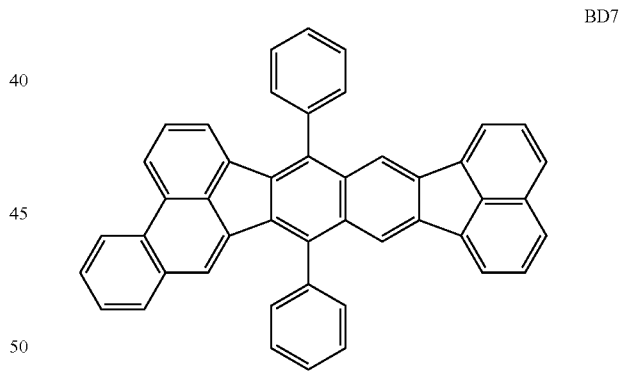
BD4
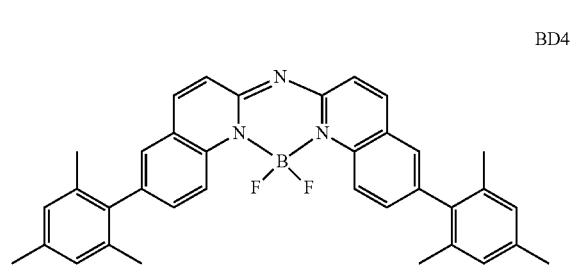
BD8
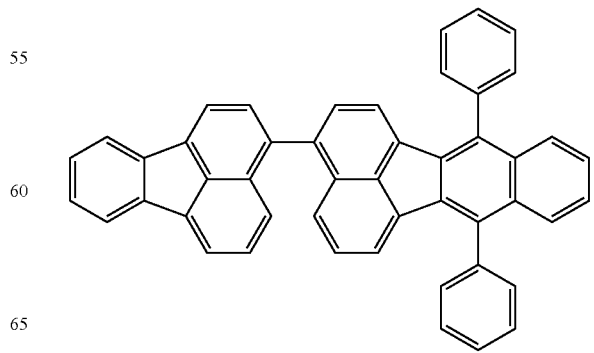

BD9
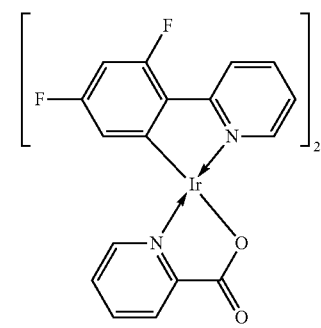
BD10
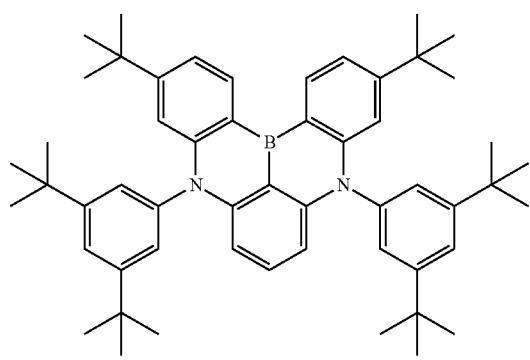
GD1
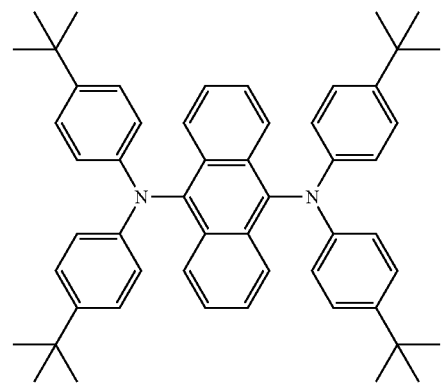
GD2
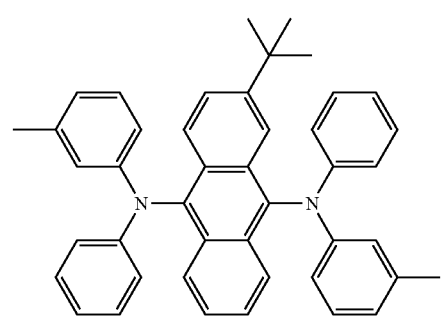
GD3
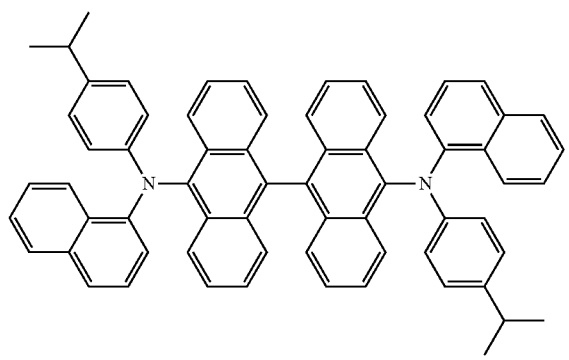
GD4
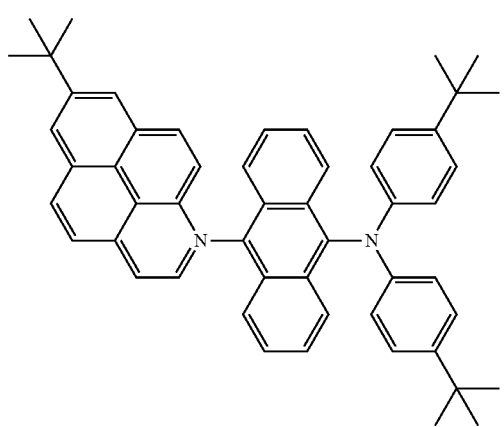
GD5
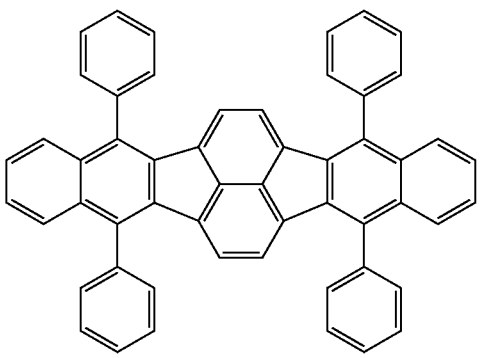
GD6
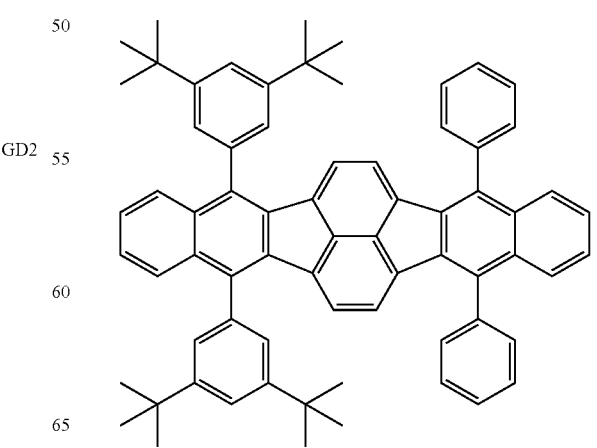

GD7
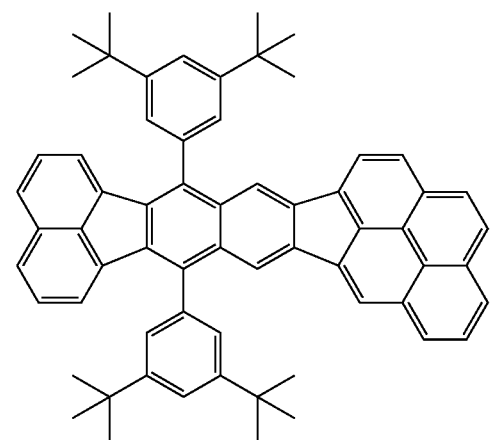
GD8
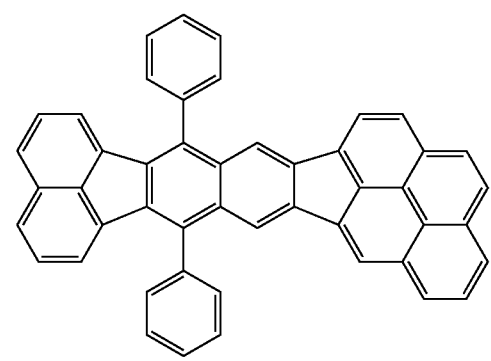
GD9
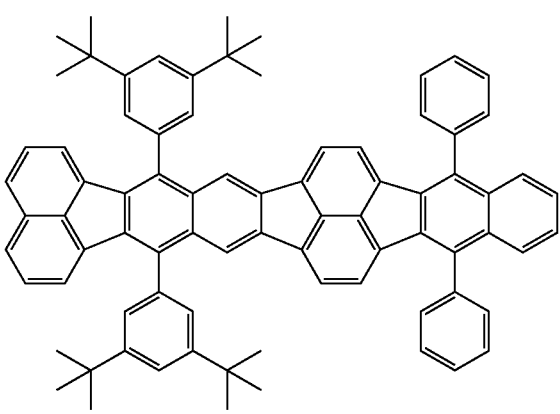
GD10
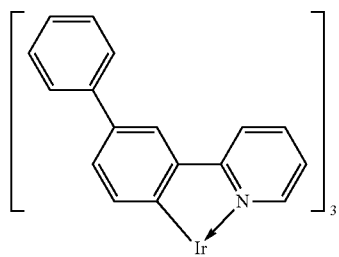
GD11
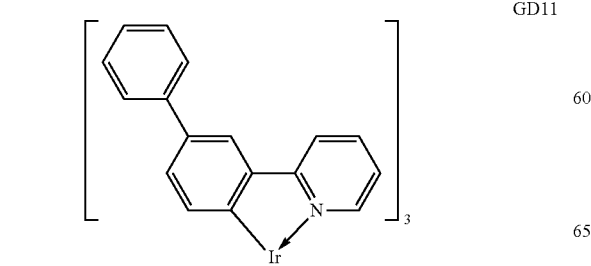
GD12
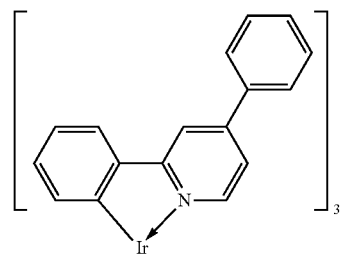
GD13
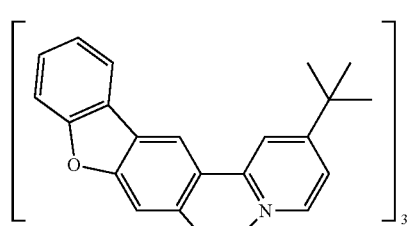
GD14
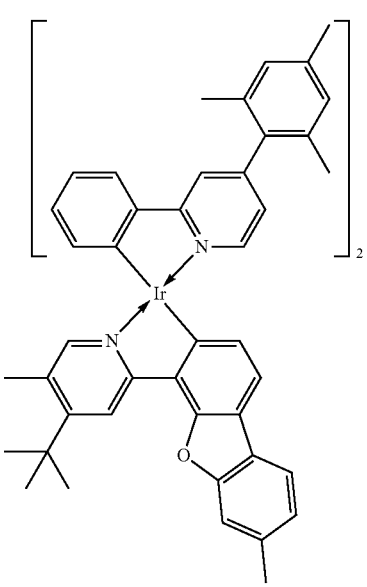
GD15
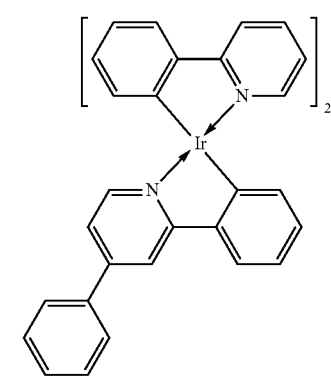

RD1
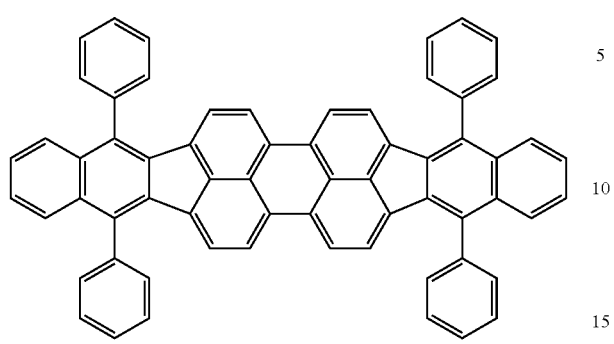
RD2
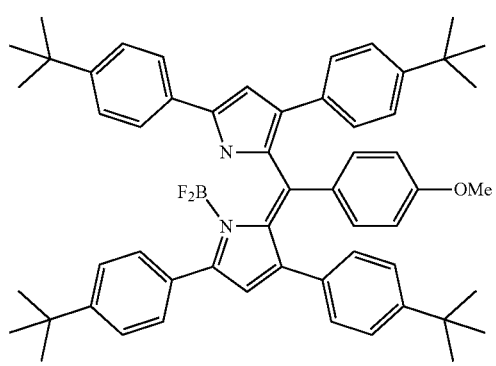
RD3
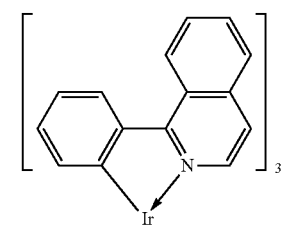
RD4
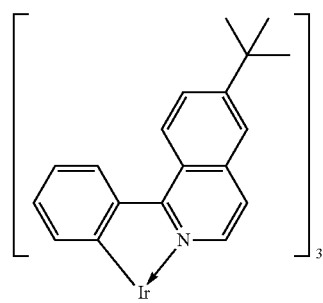
RD5
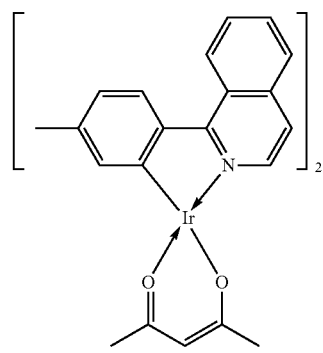
RD6
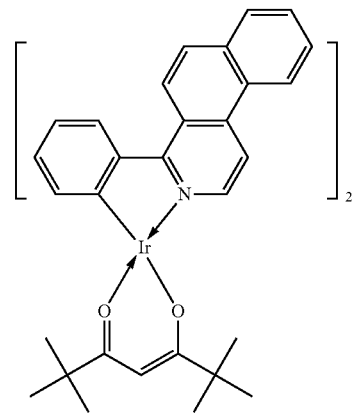
RD7
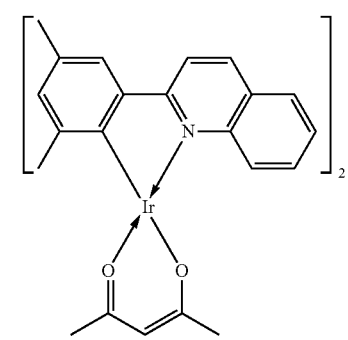
RD8
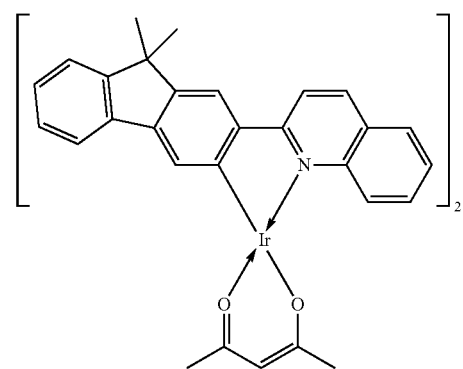
RD9
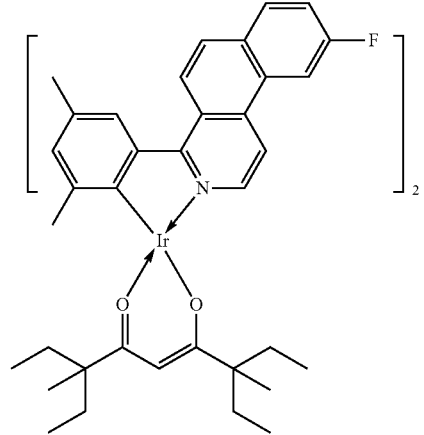

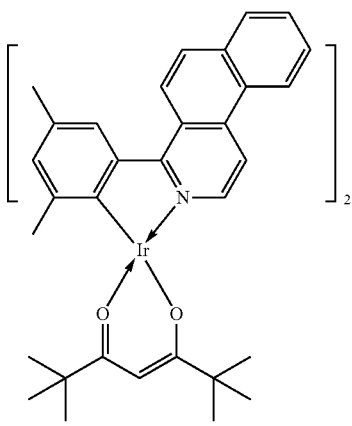

RD10

When the light-emitting material is a hydrocarbon compound, a decrease in light emission efficiency due to exciplex formation and a decrease in color purity due to a change in emission spectrum of the light-emitting material can be prevented. Here, the hydrocarbon compound is a compound consisting of carbon and hydrogen. Among the above specific examples of compounds usable as light-emitting materials, BD7, BD8, GD5 to GD9, and RD1 are hydrocarbon compounds.

When the light-emitting material is a fused polycyclic compound having a five-membered ring, the light-emitting material is less likely to undergo oxidization due to its high ionization potential, thus providing a highly durable long-life element. Among the above specific examples of compounds usable as light-emitting materials, BD7, BD8, GD5 to GD9, and RD1 are fused polycyclic compounds having a five-membered ring.

For example, when the above light-emitting material is used as a guest material of the light-emitting layer and the organic compound according to this embodiment is used as an assist material of the light-emitting layer, an element that outputs light with high efficiency and high luminance and has very high durability can be provided. In this case, the color of light emitted from the organic light-emitting element depends on the type of guest material mainly contributing to light emission. When any of compounds BD1 to BD10 is used as a guest material, an organic light-emitting element that emits blue light is provided. When any of compounds GD1 to GD15 is used as a guest material, an organic light-emitting element that emits green light is provided. When any of compounds RD1 to RD10 is used as a guest material, an organic light-emitting element that emits red light is provided.

Examples of light-emitting-layer hosts and light emission assist materials contained in the light-emitting layer include aromatic hydrocarbon compounds and derivatives thereof, carbazole derivatives, dibenzofuran derivatives, dibenzothiophene derivatives, organic aluminum complexes such as tris(8-quinolinolato)aluminum, and organic beryllium complexes.

Non-limiting specific examples of compounds usable as light-emitting-layer hosts or light emission assist materials contained in the light-emitting layer are shown below.

EM1

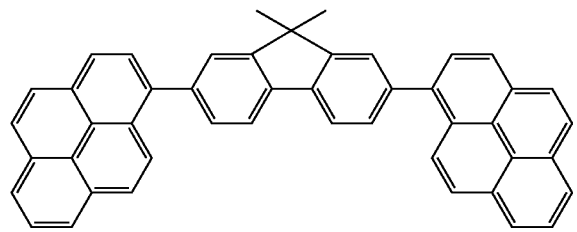

EM2

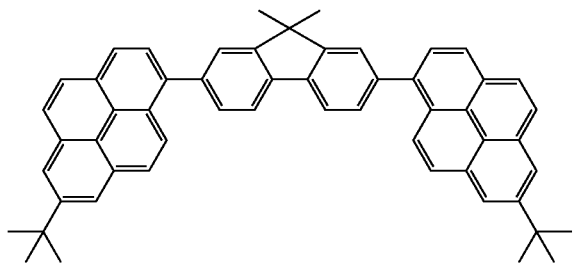

EM3

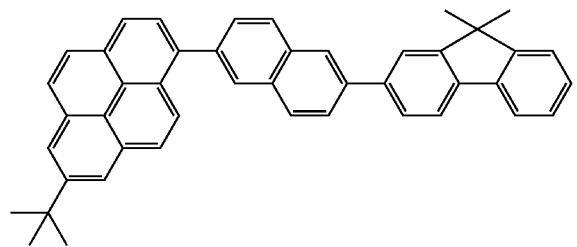

EM4

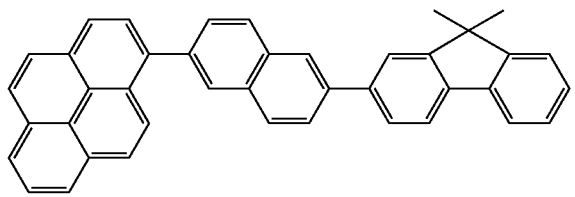

EM5

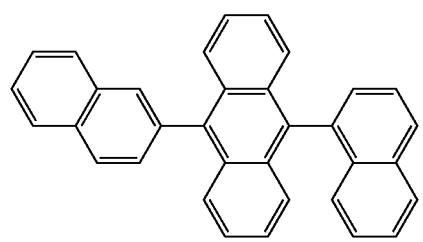

EM6

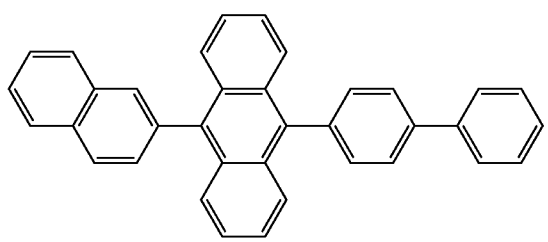

-continued
EM7
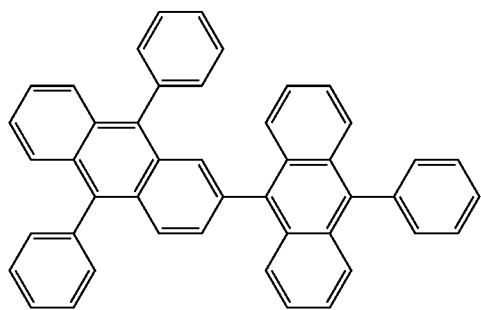
EM8
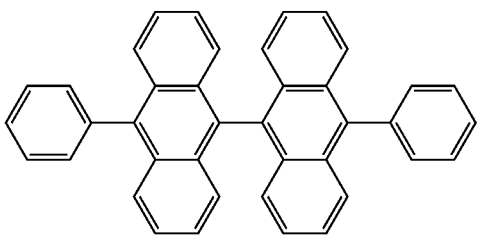
EM9
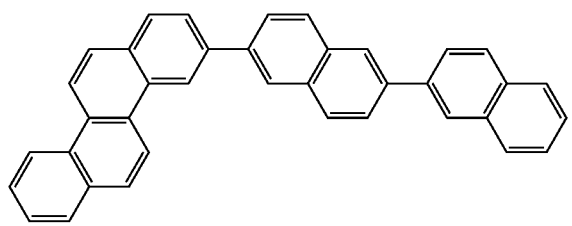
EM10
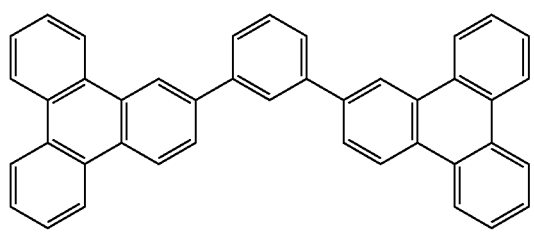
EM11
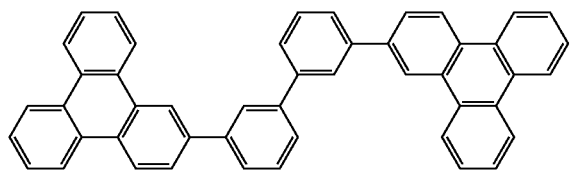
EM12
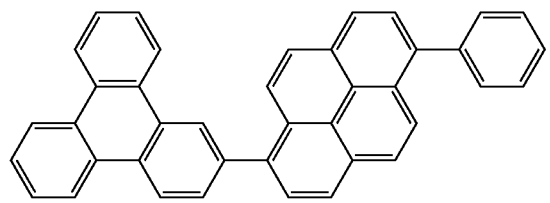
EM13
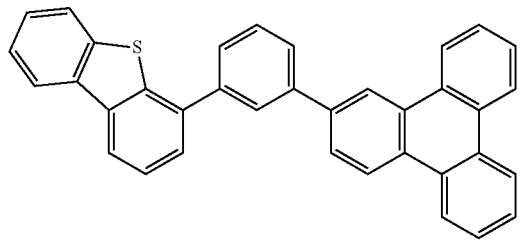
EM14
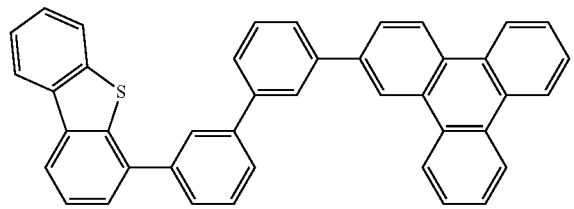
EM15
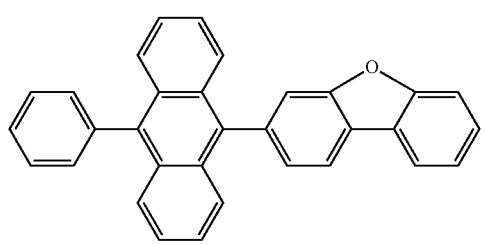
EM16
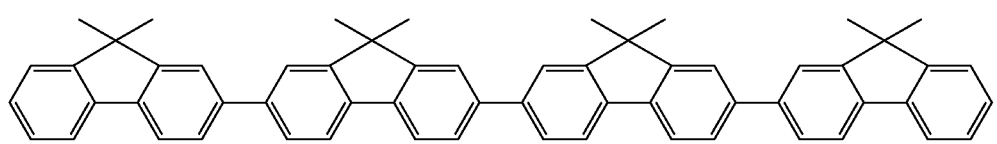

-continued
EM17
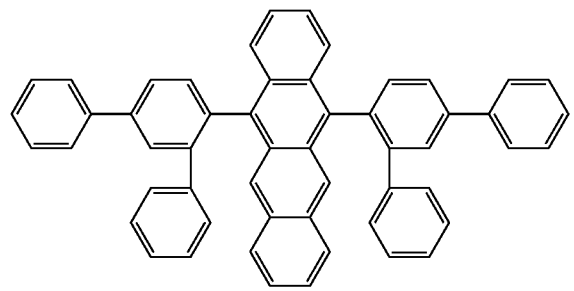
EM18
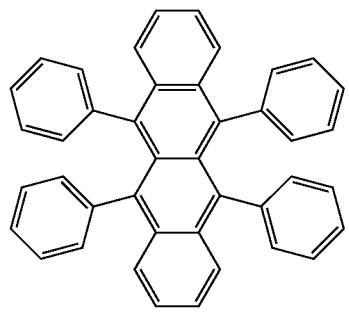
EM19
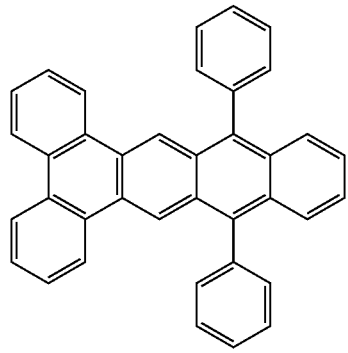
EM20
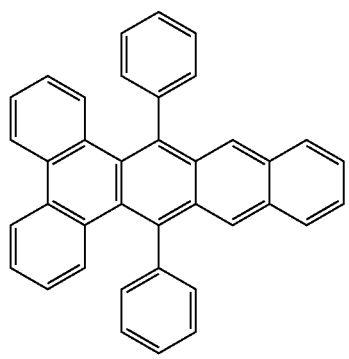
EM21
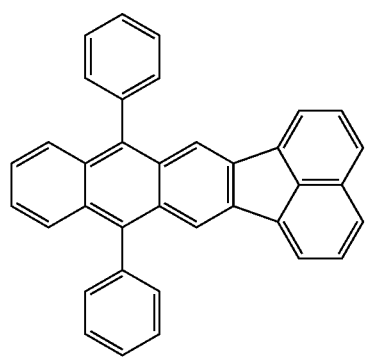
EM22
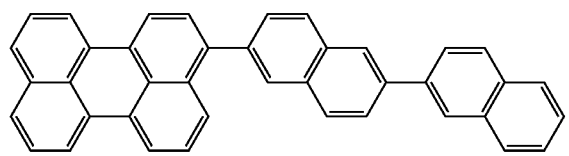
EM23
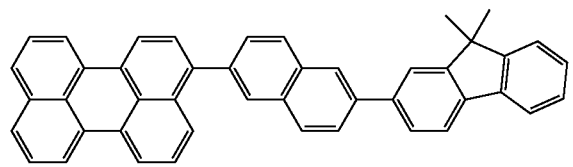
EM24
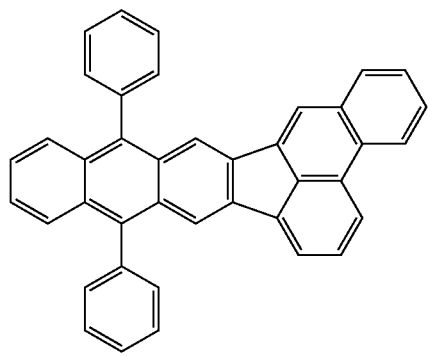
EM25
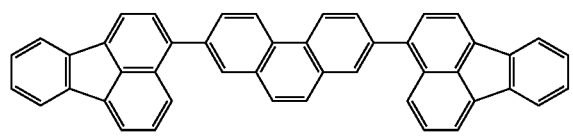

-continued
EM26
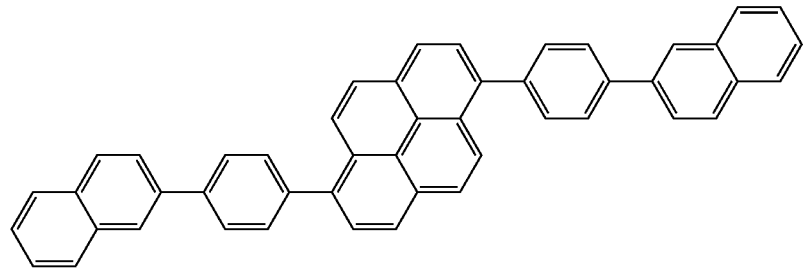
EM27
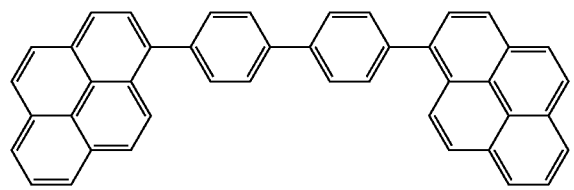
EM28
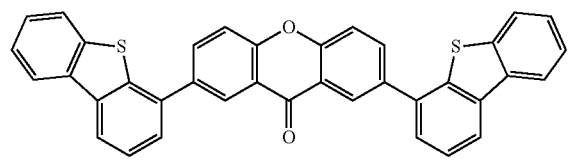
EM29
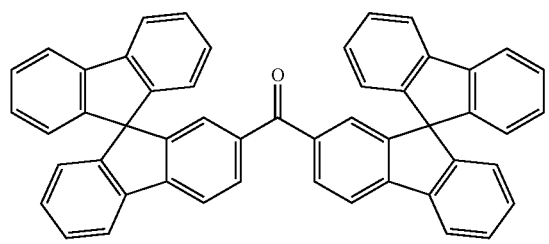
EM30
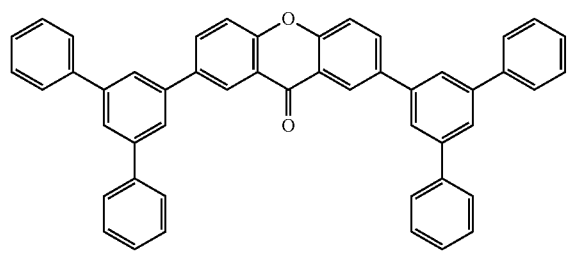
EM31
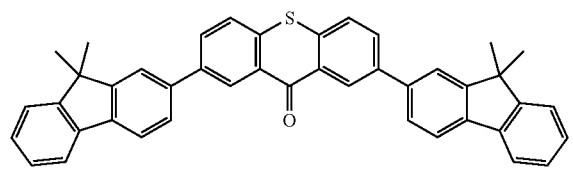
EM32
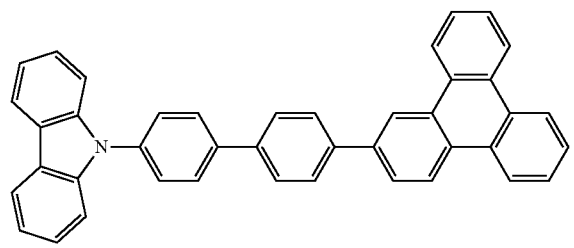
EM33
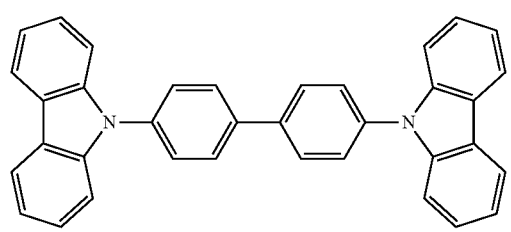
EM34
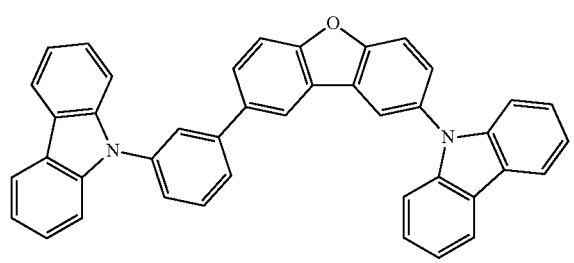

-continued

EM35
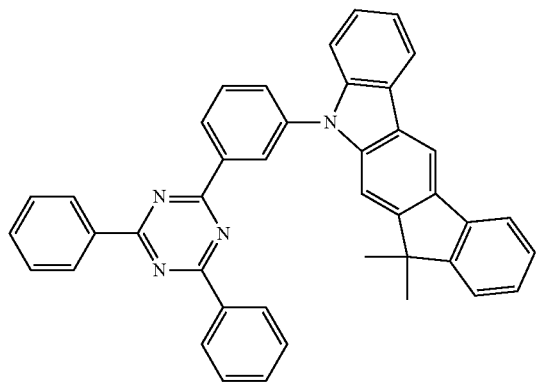

EM36
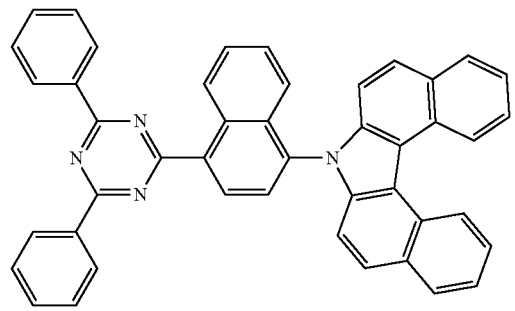

EM37
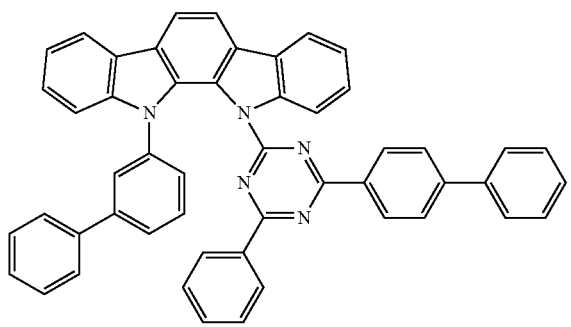

EM38
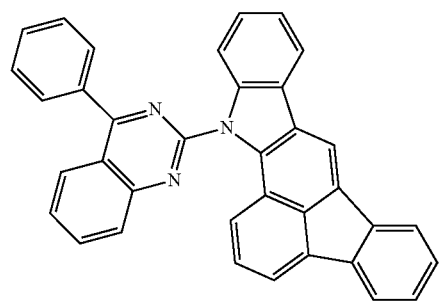

EM39
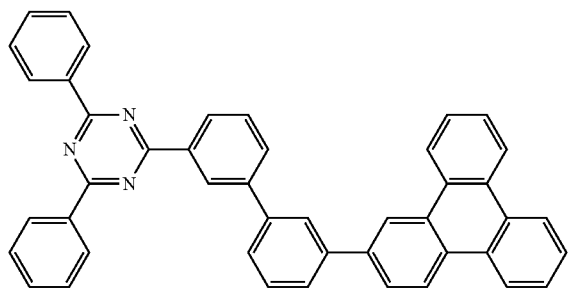

EM40
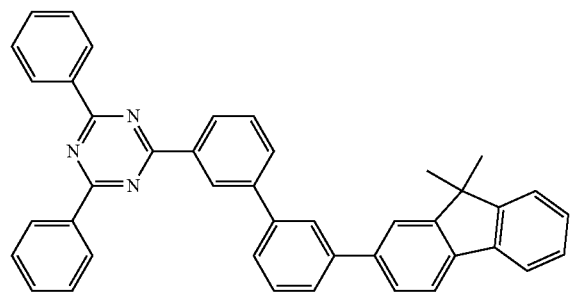

When the host material is a hydrocarbon compound, the compound of the present disclosure can easily trap electrons and holes, thus providing higher efficiency. Here, the hydrocarbon compound is a compound consisting of carbon and hydrogen. Among the above specific examples of compounds usable as host materials, EM1 to EM12 and EM16 to EM27 are hydrocarbon compounds.

Any electron transport material capable of transporting electrons injected from the cathode to the light-emitting layer can be freely selected in consideration of, for example, the balance with the hole mobility of a hole transport material. Examples of materials capable of transporting electrons include oxadiazole derivatives, oxazole derivatives, pyrazine derivatives, triazole derivatives, quinoline derivatives, quinoxaline derivatives, phenanthroline derivatives, organic aluminum complexes, and fused-ring compounds (e.g., fluorene derivatives, naphthalene derivatives, chrysene derivatives, and anthracene derivatives). These electron transport materials are also suitable for use for the hole blocking layer.

Non-limiting specific examples of compounds usable as electron transport materials are shown below.

ET1
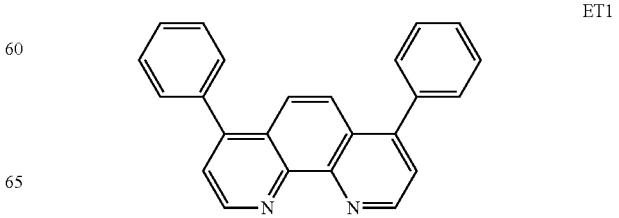

ET2
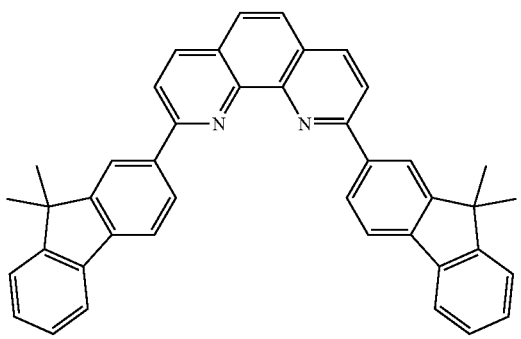
ET8
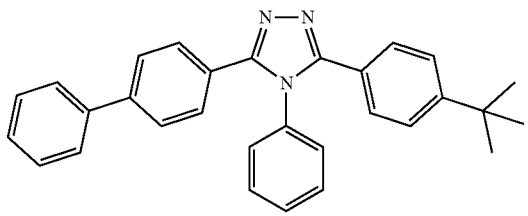
ET9
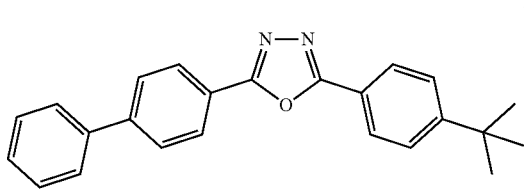
ET3
ET4
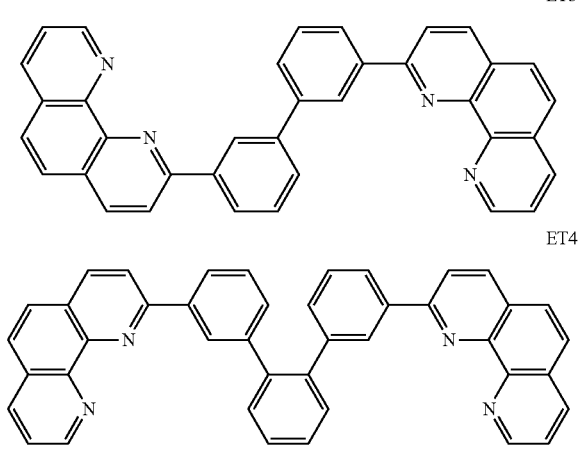
ET10
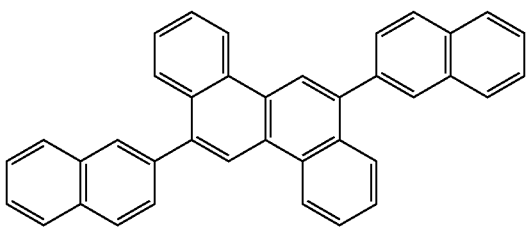
ET5
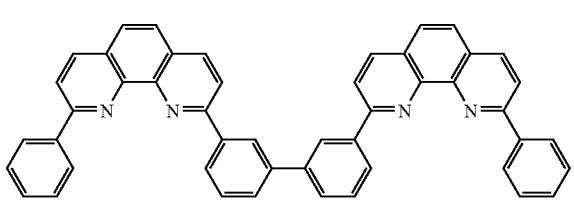
ET6
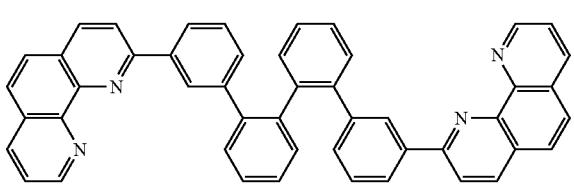
ET11
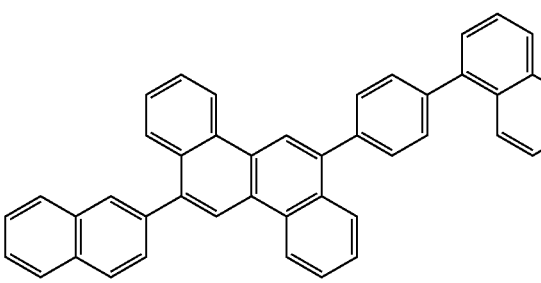
ET7
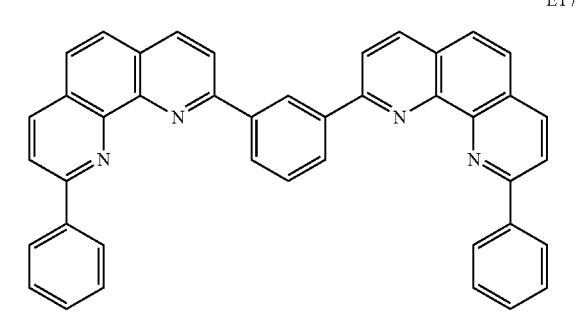
ET12
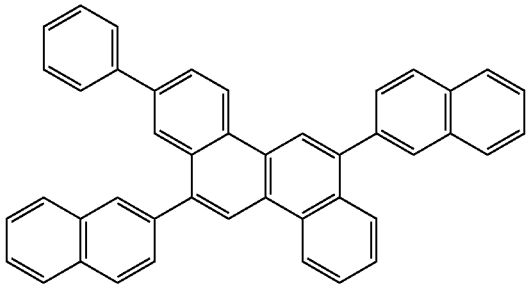

ET13
ET14
ET15
ET16
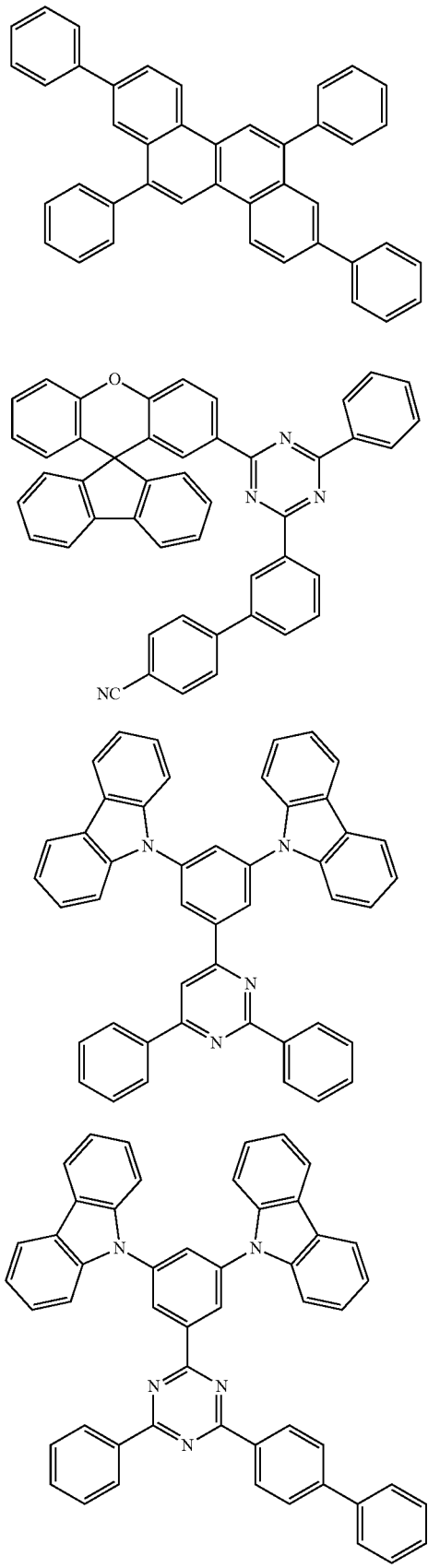
ET17
ET18
ET19
ET20
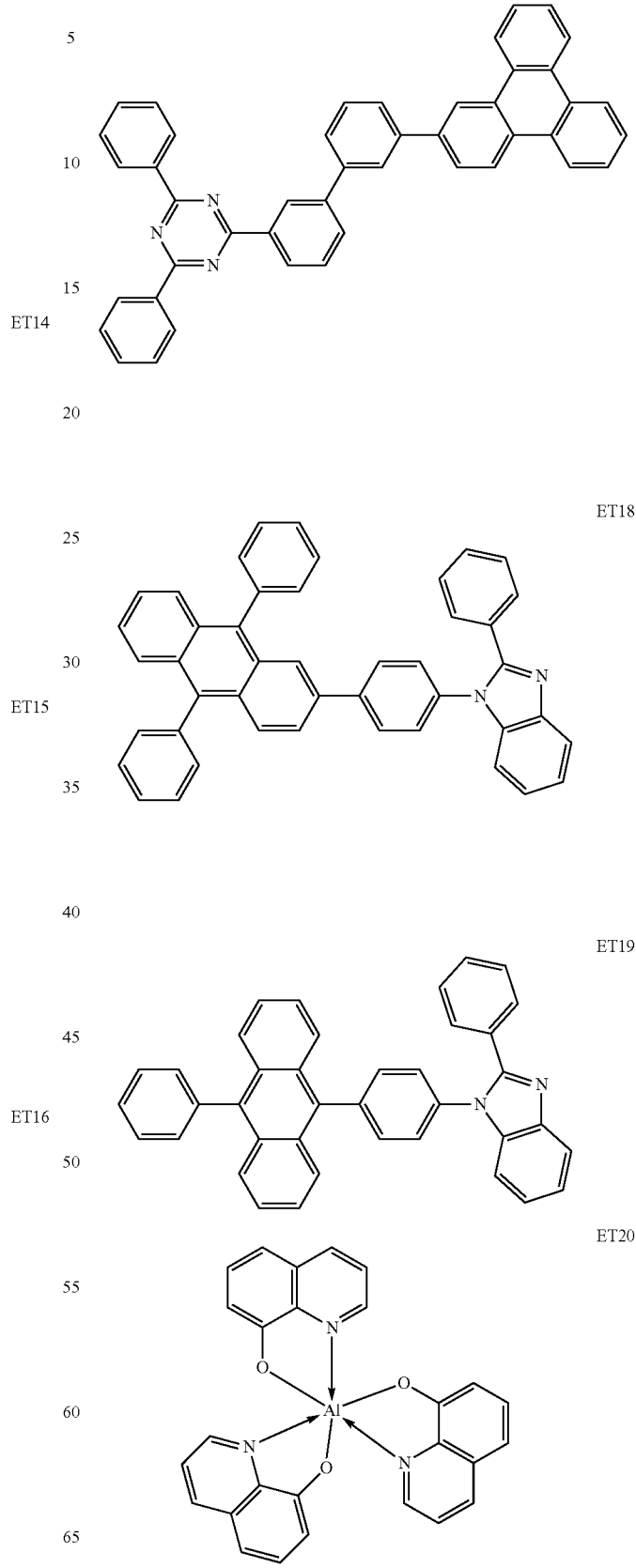

ET21
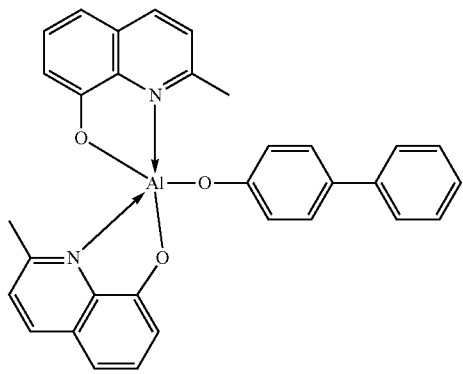

ET22
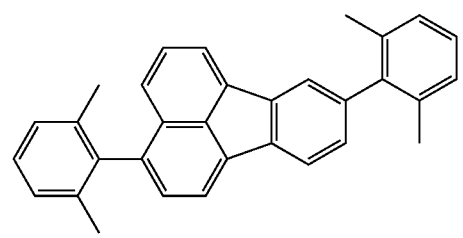

ET23
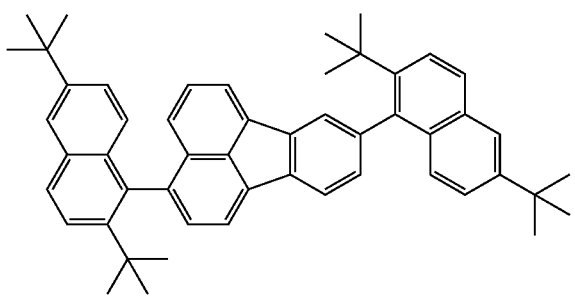

ET24
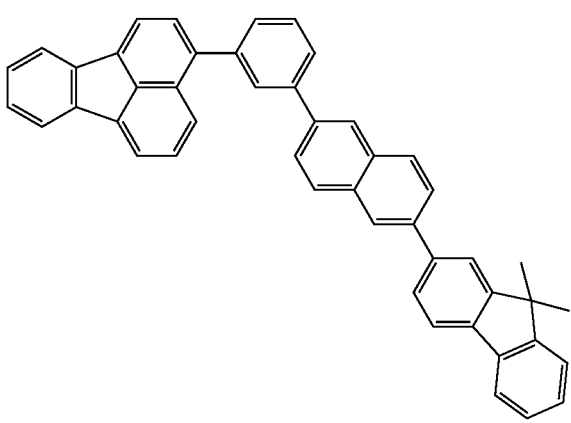

ET25
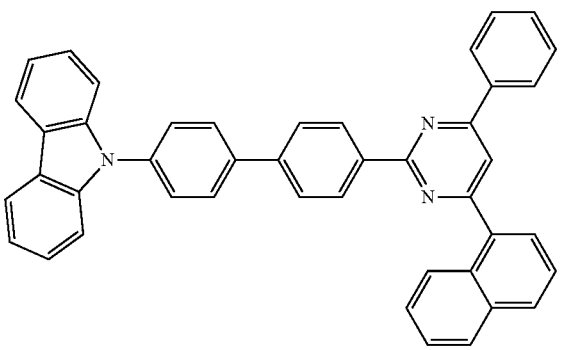

ET26
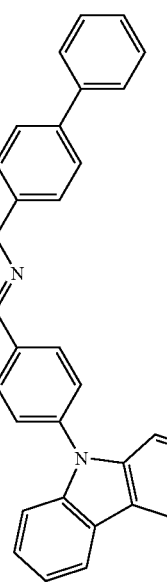

ET27
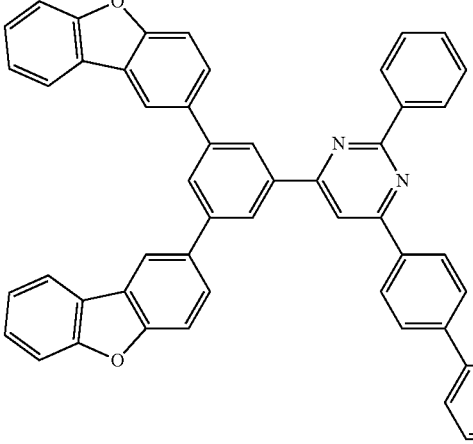

Any electron injection material capable of readily injecting electrons from the cathode can be freely selected in consideration of, for example, the balance with hole injection properties. As an organic compound, an n-type dopant and a reducing dopant are also contained. Examples of electron injection materials include alkali metal-containing compounds such as lithium fluoride, lithium complexes such as lithium quinolinol, benzimidazolidene derivatives, imidazolidene derivatives, fulvalene derivatives, and acridine derivatives.

Configuration of Organic Light-Emitting Element

The organic light-emitting element is provided by forming an anode, an organic compound layer, and a cathode on a substrate. A protective layer, a color filter, and the like may be disposed on the cathode. When the color filter is disposed, a planarization layer may be disposed between the protective layer and the color filter. The planarization layer may be composed of an acrylic resin or the like.

Substrate

As the substrate, for example, quartz, glass, a semiconductor substrate such as a silicon wafer, resin, or metal may be used. The substrate may have lines and switching elements such as transistors disposed thereon, and an insulating layer may be disposed thereon. The insulating layer may be made of any material as long as a contact hole can be formed in order to provide an electrical connection between the anode and a line and insulation for an unconnected line can be provided. For example, resins such as polyimide, silicon oxide, and silicon nitride can be used.

Electrode

A pair of electrodes may be used. The pair of electrodes may be an anode and a cathode.

When an electric field is applied in a direction in which the organic light-emitting element emits light, one of the electrodes at a higher potential is the anode, and the other is the cathode. Stated another way, one of the electrodes that supplies holes to the light-emitting layer is the anode, and the other electrode that supplies electrons to the light-emitting layer is the cathode.

The anode may be made of a material having a work function as high as possible. For example, elemental metals such as gold, platinum, silver, copper, nickel, palladium, cobalt, selenium, vanadium, and tungsten, mixtures containing these metals, alloys of these metals, and metal oxides such as tin oxide, zinc oxide, indium oxide, indium tin oxide (ITO), and indium zinc oxide can be used. Conductive polymers such as polyaniline, polypyrrole, and polythiophene can also be used.

These electrode materials may be used alone or in combination of two or more. The anode may be composed of a single layer or a plurality of layers.

When the anode is used as a reflection electrode, chromium, aluminum, silver, titanium, tungsten, molybdenum, an alloy thereof, or a laminate thereof can be used, for example. When the anode is used as a transparent electrode, a transparent conductive layer made of an oxide such as indium tin oxide (ITO) or indium zinc oxide can be used, but these materials are not limiting examples.

Photolithography can be used for electrode formation.

The cathode may be made of a material having a low work function. Examples of such materials include alkali metals such as lithium; alkaline earth metals such as calcium; elemental metals such as aluminum, titanium, manganese, silver, lead, and chromium; and mixtures containing these elemental metals. Alloys of these elemental metals can also be used. For example, magnesium-silver, aluminum-lithium, aluminum-magnesium, silver-copper, and zinc-silver can be used. Metal oxides such as indium tin oxide (ITO) can also be used. These electrode materials may be used alone or in combination of two or more. The cathode may be composed of a single layer or a plurality of layers. In particular, silver is preferably used, and a silver alloy is more preferred to suppress aggregation of silver. As long as aggregation of silver can be suppressed, the content ratio in the alloy is not limited, and may be 1:1, for example.

The cathode is not particularly limited, and may be formed as a conductive layer of an oxide such as ITO to provide a top-emission organic light-emitting element or may be formed as a reflection electrode of aluminum (Al) or the like to provide a bottom-emission organic light-emitting element. The cathode may be formed by any method, but, for example, DC and AC sputtering processes may be used because these methods provide good film coverage and readily reduce resistance.

Protective Layer

After the cathode is formed, a protective layer may be disposed. For example, by bonding a glass plate provided with a moisture absorbent to the cathode, permeation of water and the like into the organic compound layer can be suppressed, and the occurrence of a display failure can be suppressed. In another embodiment, a passivation film made of silicon nitride or the like may be disposed on the cathode to reduce permeation of water and the like into the organic EL layer. For example, the protective layer may be formed in such a manner that after the formation of the cathode, the resultant is conveyed to another chamber without breaking the vacuum, and a silicon nitride film having a thickness of 2 μm is formed by chemical-vapor deposition (CVD). After the film formation by CVD, atomic layer deposition (ALD) may be performed to form a protective layer.

Color Filter

A color filter may be disposed on the protective layer. For example, a color filter sized to fit the organic light-emitting element may be formed on another substrate, and this substrate may be bonded to the substrate on which the organic light-emitting element has been disposed. Alternatively, a color filter may be patterned on a protective layer made of silicon oxide or the like by photolithography. The color filter may be formed of a polymer.

Planarization Layer

A planarization layer may be disposed between the color filter and the protective layer. The planarization layer may be formed of an organic compound. The organic compound may have a low molecular weight or a high molecular weight, and preferably has a high molecular weight.

Two planarization layers may be disposed on opposite surfaces of the color filter, and the materials thereof may be the same or different. Specific examples of the materials include polyvinylcarbazole resins, polycarbonate resins, polyester resins, ABS resins, acrylic resins, polyimide resins, phenol resins, epoxy resins, silicone resins, and urea resins.

Counter Substrate

A counter substrate may be disposed on the planarization layer. The counter substrate is disposed at a position counter to the above-described substrate and thus is referred to as the counter substrate. The material forming the counter substrate may be the same as that of the above-described substrate.

Organic Layer

The organic compound layers (e.g., a hole injection layer, a hole transport layer, an electron blocking layer, a light-emitting layer, a hole blocking layer, an electron transport layer, and an electron injection layer) constituting an organic light-emitting element according to an embodiment of the present disclosure are formed by the following method.

The organic compound layers constituting an organic light-emitting element according to an embodiment of the present disclosure can be formed using a dry process such as vacuum deposition, ion plating, sputtering, or plasma deposition. Instead of the dry process, a wet process in which an organic compound is dissolved in an appropriate solvent and a layer is formed by a known coating method (e.g., spin coating, dipping, a casting method, a Langmuir-Blodgett (LB) method, or an ink jet method) can also be used.

When the layers are formed, for example, by vacuum deposition or solution coating, the layers are unlikely to undergo crystallization or the like and are highly stable over time. When a coating method is used for film formation, an appropriate binder resin can be used in combination to form a film.

Examples of the binder resin include, but are not limited to, polyvinylcarbazole resins, polycarbonate resins, polyester resins, ABS resins, acrylic resins, polyimide resins, phenol resins, epoxy resins, silicone resins, and urea resins.

These binder resins may be used alone as a homopolymer or copolymer or may be used as a mixture of two or more. In addition, known additives such as plasticizers, oxidation inhibitors, and ultraviolet absorbents may be used in combination as needed.

Applications of Organic Light-Emitting Element According to this Embodiment

The organic light-emitting element according to this embodiment can be used as a constituent member of a display apparatus or an illumination apparatus. Other applications include an exposure light source in an electrophotographic image-forming apparatus, a backlight in a liquid crystal display apparatus, and a light-emitting apparatus including a white light source with a color filter.

The display apparatus may be an image information processing apparatus including an image input unit that receives image information from an area CCD, a linear CCD, a memory card, or the like, an information-processing unit that processes the input information, and a display unit that displays the input image. The display apparatus includes a plurality of pixels, and at least one of the plurality of pixels may include the organic light-emitting element according to this embodiment and a transistor connected to the organic light-emitting element. In this case, the substrate may be a semiconductor substrate made of silicon or the like, and the transistor may be a MOSFET formed on the substrate.

The display unit of an image pickup apparatus or an ink-jet printer may have a touch panel function. The touch panel function may be activated by any system, such as an infrared system, an electrostatic capacitive system, a resistive film system, or an electromagnetic induction system. The display apparatus may also be used in a display unit of a multifunctional printer.

Next, a display apparatus according to an embodiment will be described with reference to the drawings.

Figure 1B:
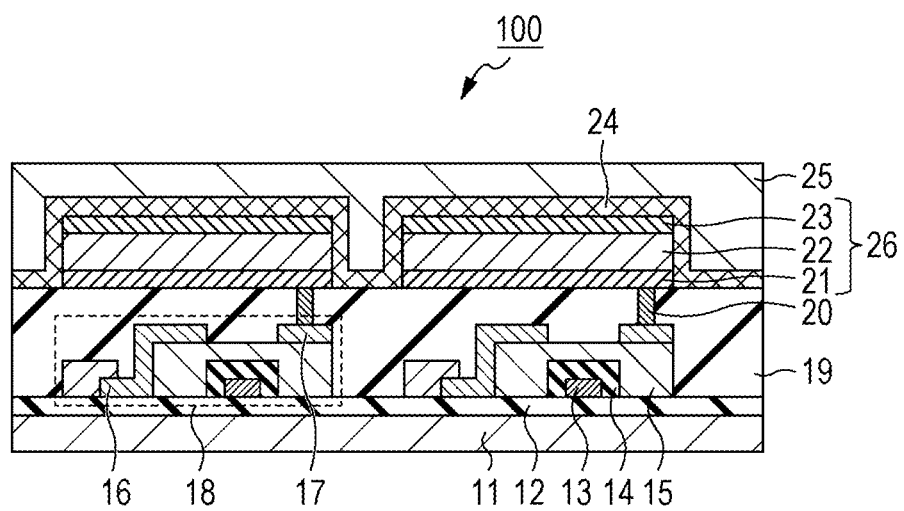
FIG. 1B is a schematic sectional view of an example of a display apparatus including an organic light-emitting element according to an embodiment of the present disclosure.

FIGS. 1A and 1B are schematic sectional views each illustrating an example of a display apparatus including an organic light-emitting element and a transistor connected to the organic light-emitting element. The transistor is an example of an active element. The transistor may be a thin film transistor (TFT).

FIG. 1A is an example of a pixel that is a component of the display apparatus according to this embodiment. The pixel has subpixels 10. The subpixels are divided into subpixels 10R, 10G, and 10B according to their light emission. The emission color may be differentiated by the wavelength of light emitted from a light-emitting layer. Alternatively, light emitted from the subpixels may be selectively transmitted through a color filter or the like or subjected to color conversion by a color filter or the like. Each of the subpixels includes, on an interlayer insulating layer 1, a reflective electrode 2 serving as a first electrode, an insulating layer 3 that covers the edge of the reflective electrode 2, an organic compound layer 4 that covers the first electrode and the insulating layer, a transparent electrode 5, a protective layer 6, and a color filter 7.

The interlayer insulating layer 1 may include a transistor and a capacitor element below or inside the interlayer insulating layer 1.

The transistor and the first electrode may be electrically connected to each other through a contact hole (not illustrated) or the like.

The insulating layer 3 is also referred to as a bank or a pixel-separating film. The insulating layer 3 is disposed so as to cover the edge of the first electrode and surround the first electrode. A portion in which the insulating layer is not disposed is in contact with the organic compound layer 4 and serves as a light-emitting region.

The organic compound layer 4 includes a hole injection layer 41, a hole transport layer 42, a first light-emitting layer 43, a second light-emitting layer 44, and an electron transport layer 45.

The second electrode 5 may be a transparent electrode, a reflective electrode, or a semitransparent electrode.

The protective layer 6 suppresses permeation of water into the organic compound layer. Although the protective layer is illustrated as a single layer, it may be constituted by a plurality of layers. The layers may be constituted by an inorganic compound layer and an organic compound layer.

The color filter 7 is divided into color filters 7R, 7G, and 7B according to their color. The color filter may be formed on a planarizing film (not illustrated). A resin protective layer (not illustrated) may be disposed on the color filter. The color filter may be formed on the protective layer 6. The color filter may be bonded after being formed on a counter substrate such as a glass substrate.

A display apparatus 100 in FIG. 1B includes an organic light-emitting element 26 and a TFT 18, which is an example of the transistor. An insulating layer 12 is disposed on a substrate 11 made of glass, silicon, or the like. An active element such as the TFT 18 is disposed on the insulating layer 12, and the active element is constituted by a gate electrode 13, a gate insulating film 14, and a semiconductor layer 15.

The TFT 18 includes the semiconductor layer 15, a drain electrode 16, and a source electrode 17. An insulating film 19 is disposed over the TFT 18. An anode 21 constituting the organic light-emitting element 26 and the source electrode 17 are connected to each other through a contact hole 20.

The electrodes (the anode 21 and a cathode 23) included in the organic light-emitting element 26 and the electrodes (the source electrode 17 and the drain electrode 16) included in the TFT need not necessarily be electrically connected to each other in the manner illustrated in FIG. 1B. It is only required that either the anode 21 or the cathode 23 be electrically connected to either the source electrode 17 or the drain electrode 16 of the TFT 18.

Although an organic compound layer 22 is illustrated as a single layer in the display apparatus 100 in FIG. 1B, the organic compound layer 22 may be constituted by a plurality of layers. A first protective layer 25 and a second protective layer 24 for suppressing deterioration of the organic light-emitting element are disposed over the cathode 23.

Although a transistor is used as a switching element in the display apparatus 100 in FIG. 1B, another switching element such as a metal-insulator-metal (MIM) element may be used instead.

The transistor used in the display apparatus 100 in FIG. 1B may not only be a thin-film transistor including a substrate and an active layer on an insulating surface of the substrate but also a transistor obtained using a single-crystal silicon wafer. The active layer may be formed of, for example, single-crystal silicon, non-single-crystal silicon such as amorphous silicon or microcrystalline silicon, or a non-single-crystal oxide semiconductor such as indium zinc oxide or indium gallium zinc oxide. The thin-film transistor is also referred to as a TFT element.

The transistor included in the display apparatus 100 in FIG. 1B may be formed in a substrate such as a Si substrate. The phrase "formed in a substrate" means producing a transistor by processing a substrate itself, such as a Si substrate. That is, having a transistor in a substrate can also mean that the substrate and the transistor are integrally formed.

The organic light-emitting element according to this embodiment has an emission luminance that is controlled by a TFT, which is an example of a switching element. When a plurality of the organic light-emitting elements are disposed in a plane, an image can be displayed with different emission luminances. The switching element according to this embodiment need not necessarily be a TFT and may be a transistor formed of low-temperature polysilicon or an active matrix driver formed on a substrate such as a Si substrate. The active matrix driver may also be formed in the substrate. Whether a transistor is provided in the substrate or a TFT is used is chosen depending on the size of the display unit. For example, when the display unit has a size of about 0.5 inches, the organic light-emitting element may be disposed on a Si substrate.

Figure 2:
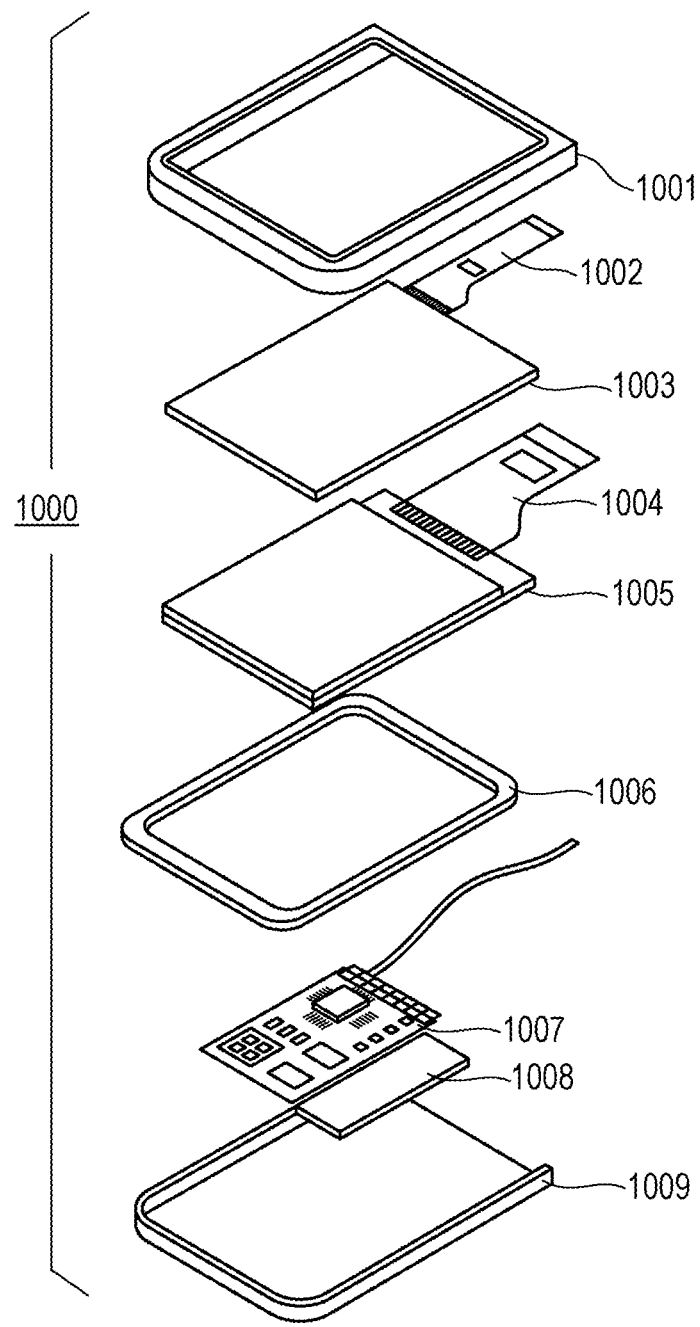
FIG. 2 schematically illustrates an example of a display apparatus according to an embodiment of the present disclosure.

FIG. 2 schematically illustrates an example of the display apparatus according to this embodiment. A display apparatus 1000 may include an upper cover 1001, a lower cover 1009, and a touch panel 1003, a display panel 1005, a frame 1006, a circuit substrate 1007, and a battery 1008 disposed between the upper cover 1001 and the lower cover 1009. Flexible print circuits (FPCs) 1002 and 1004 are connected to the touch panel 1003 and the display panel 1005, respectively. A transistor is printed on the circuit substrate 1007. The battery 1008 may be omitted if the display apparatus is not a mobile device. When the display apparatus is a mobile device, the battery 1008 may be disposed in another position.

The display apparatus according to this embodiment may be used as a display unit of an image pickup apparatus that includes an optical unit including a plurality of lenses and an image pickup element that receives light that has passed through the optical unit. The image pickup apparatus may include a display unit that displays information acquired by the image pickup element. The display unit may be exposed to the outside of the image pickup apparatus or disposed in a viewfinder. The image pickup apparatus may be a digital camera or a digital camcorder. The image pickup apparatus may be referred to as a photoelectric conversion apparatus.

Figure 3A:
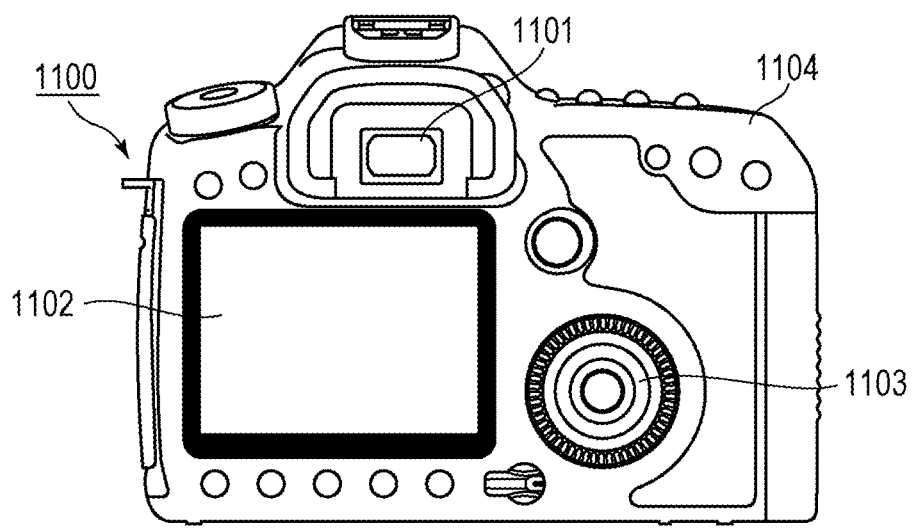
FIG. 3A schematically illustrates an example of an image pickup apparatus according to an embodiment of the present disclosure.

FIG. 3A schematically illustrates an example of an image pickup apparatus according to this embodiment. An image pickup apparatus 1100 may include a viewfinder 1101, a rear display 1102, an operation unit 1103, and a housing 1104. The viewfinder 1101 may include the display apparatus according to this embodiment. In this case, the display apparatus may display not only an image to be captured but also environmental information, image capturing instructions, and the like. The environmental information may be, for example, the intensity of external light, the direction of external light, the moving speed of a photographic subject, and the possibility that the photographic subject is hidden by an object.

Since the timing appropriate for capturing an image is only a moment, the information is desirably displayed as quickly as possible. Thus, the display apparatus including the organic light-emitting element according to this embodiment may be used. This is because the organic light-emitting element has a high response speed. The display apparatus including the organic light-emitting element is more suitable for use than such apparatuses and liquid crystal display apparatuses that are required to have a high display speed.

The image pickup apparatus 1100 includes an optical unit (not illustrated). The optical unit includes a plurality of lenses and focuses an image on the image pickup element accommodated in the housing 1104. By adjusting the relative positions of the plurality of lenses, the focal point can be adjusted. This operation can also be performed automatically.

The display apparatus according to this embodiment may include red, green, and blue color filters. The red, green, and blue color filters may be disposed in a delta arrangement.

The display apparatus according to this embodiment may be used in a display unit of an electronic apparatus such as a mobile terminal. In this case, the display apparatus may have both a display function and an operating function. Examples of mobile terminals include cellular phones such as smart phones, tablets, and head mount displays.

Figure 3B:
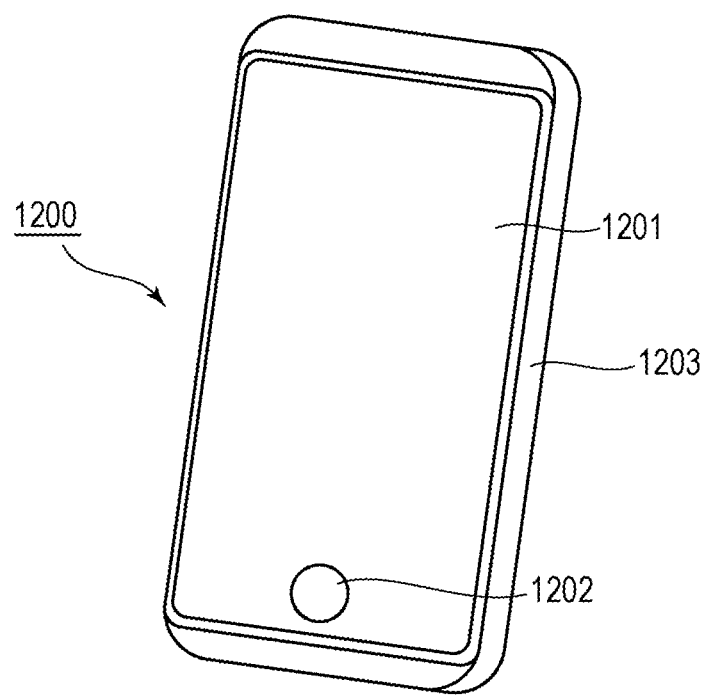
FIG. 3B schematically illustrates an example of a mobile device according to an embodiment of the present disclosure.

FIG. 3B schematically illustrates an example of an electronic apparatus according to this embodiment. An electronic apparatus 1200 includes a display unit 1201, an operation unit 1202, and a housing 1203. The housing 1203 may include a circuit, a printed board including the circuit, a battery, and a communication unit. The operation unit 1202 may be a button or a touch-sensitive response unit. The operation unit may be a biometric recognition unit that, for example, releases a lock through recognition of fingerprints. An electronic apparatus including a communication unit can also be referred to as a communication apparatus.

Figure 4A:
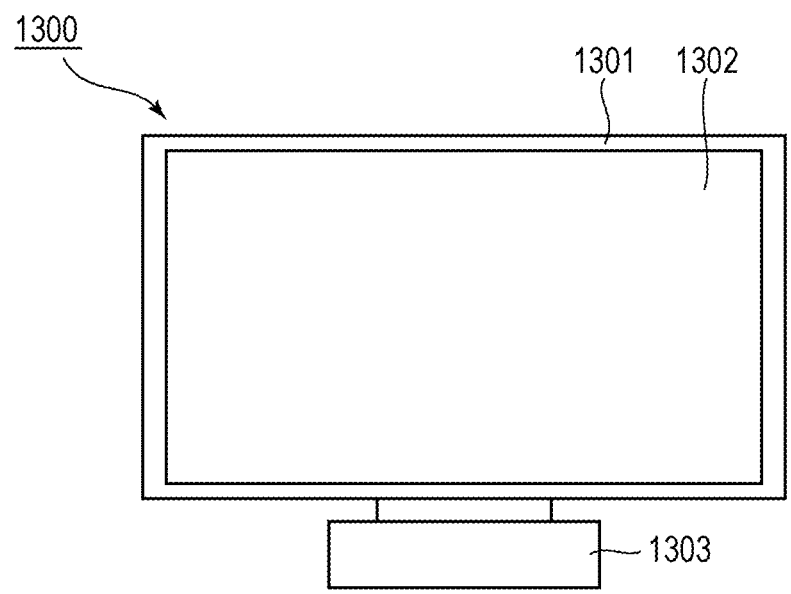
FIG. 4A schematically illustrates an example of a display apparatus according to an embodiment of the present disclosure.
Figure 4B:
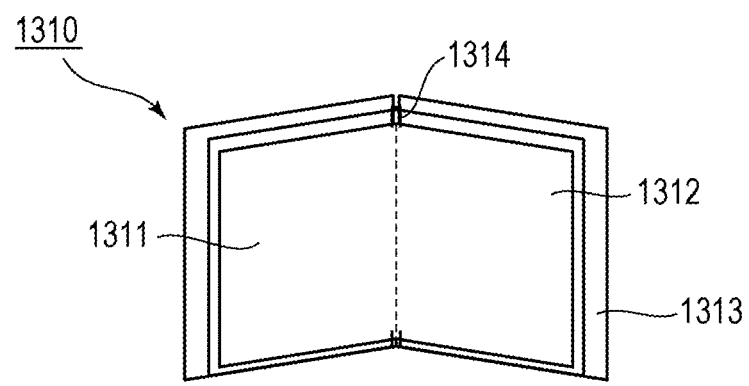
FIG. 4B schematically illustrates an example of a foldable display apparatus.

FIGS. 4A and 4B schematically illustrate examples of the display apparatus according to this embodiment. FIG. 4A illustrates a display apparatus such as a television monitor or a PC monitor. A display apparatus 1300 includes a frame 1301 and a display unit 1302. A light-emitting device according to this embodiment may be used for the display unit 1302. The display apparatus 1300 includes a base 1303 that supports the frame 1301 and the display unit 1302. The base 1303 need not necessarily be in the form illustrated in FIG. 4A. The lower side of the frame 1301 may serve as a base. The frame 1301 and the display unit 1302 may be bent such that the display surface of the display unit 1302 is curved. The radius of the curvature may be 5,000 mm or more and 6,000 mm or less.

FIG. 4B schematically illustrates another example of the display apparatus according to this embodiment. A display apparatus 1310 in FIG. 4B is configured to be foldable and is what is called a foldable display apparatus. The display apparatus 1310 includes a first display unit 1311, a second display unit 1312, a housing 1313, and a bending point 1314. The first display unit 1311 and the second display unit 1312 may include the light-emitting device according to this embodiment. The first display unit 1311 and the second display unit 1312 may be a seamless, monolithic display apparatus. The first display unit 1311 and the second display unit 1312 can be divided by the bending point. The first display unit 1311 and the second display unit 1312 may display different images, or the first and second display units may together display a single image.

Figure 5A:
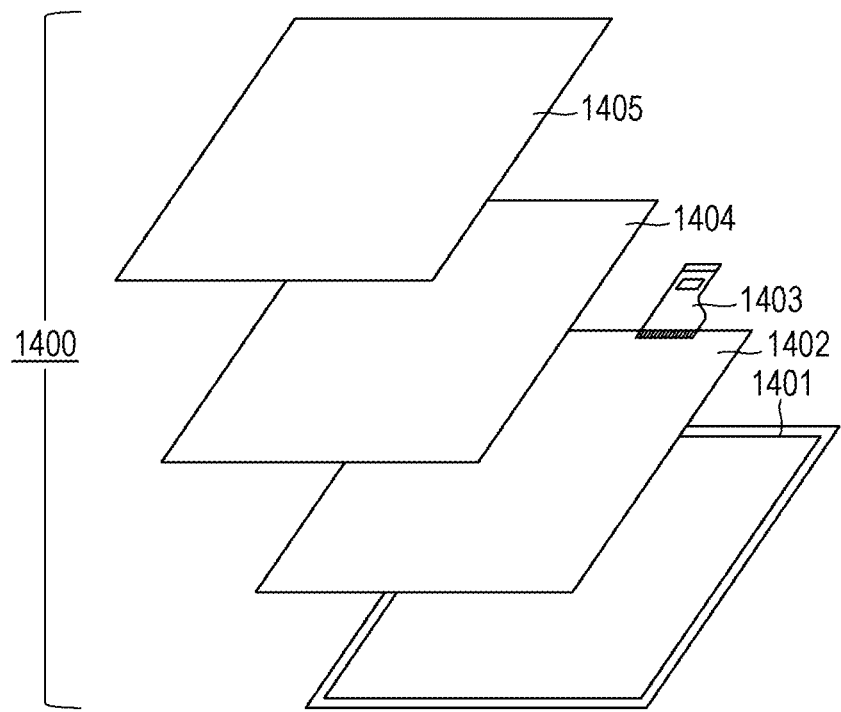
FIG. 5A schematically illustrates an example of an illumination apparatus according to an embodiment of the present disclosure.

FIG. 5A schematically illustrates an example of an illumination apparatus according to this embodiment. An illumination apparatus 1400 may include a housing 1401, a light source 1402, a circuit board 1403, an optical filter 1404 that transmits light emitted from the light source 1402, and a light diffusion unit 1405. The light source 1402 may include the organic light-emitting element according to this embodiment. The optical filter may be a filter for improving the color rendering properties of the light source. The light diffusion unit effectively diffuses light from the light source and helps the light reach a wide region for, for example, lighting up. The optical filter and the light diffusion unit may be disposed on the light-emitting side of the illumination apparatus. Optionally, a cover may be disposed at an outermost portion.

The illumination apparatus is, for example, an indoor illumination apparatus. The illumination apparatus may emit light of cool white, day white, or any other color from blue to red. The illumination apparatus may include a light modulation circuit that modulates the light or a color modulation circuit that modulates the color of the emitted light. The illumination apparatus may include the organic light-emitting element according to this embodiment and a power supply circuit connected thereto. The power supply circuit is a circuit that converts AC voltage to DC voltage. Cool white has a color temperature of 4200 K, and day white has a color temperature of 5000 K. The illumination apparatus may include a color filter.

The illumination apparatus according to this embodiment may also include a heat dissipation unit. The heat dissipation unit is configured to dissipate heat inside the apparatus out of the apparatus and may be formed of, for example, a metal of high specific heat or liquid silicone.

Figure 5B:
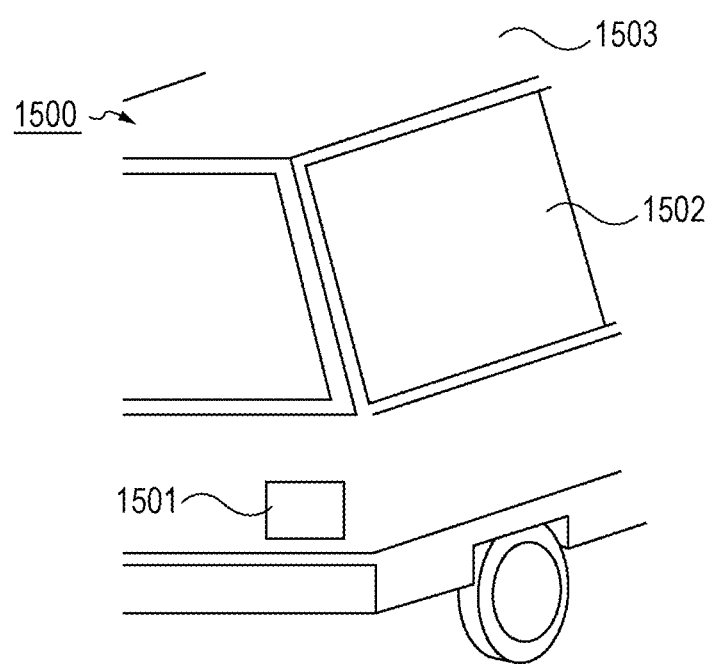
FIG. 5B schematically illustrates an automobile that is an example of a moving object according to an embodiment of the present disclosure.

FIG. 5B schematically illustrates an automobile that is an example of a moving object according to this embodiment. The automobile includes a tail lamp that is an example of a lighting fixture. An automobile 1500 includes a tail lamp 1501, and the tail lamp may be configured to be turned on in response to, for example, brake operation.

The tail lamp 1501 may include the organic light-emitting element according to this embodiment. The tail lamp 1501 may include a protective member that protects the organic EL element. The protective member may be made of any material that is strong to some extent and transparent, and may be made of, for example, polycarbonate. The polycarbonate may be mixed with, for example, a furandicarboxylic acid derivative or an acrylonitrile derivative.

The automobile 1500 may include a car body 1503 and a window 1502 attached thereto. The window 1502 may be a transparent display unless it is a window for checking the front and rear of the automobile. The transparent display may include the organic light-emitting element according to this embodiment.

In this case, components, such as electrodes, of the organic light-emitting element are formed of transparent materials.

The moving object according to this embodiment may be, for example, a ship, an aircraft, or a drone. The moving object may include a body and a lighting fixture provided on the body. The lighting fixture may emit light for allowing the position of the body to be recognized. The lighting fixture includes the organic light-emitting element according to this embodiment.

Application examples of the display apparatuses according to the above embodiments will be described with reference to FIG. 6. The display apparatuses can be applied to systems that can be worn as wearable devices such as smart glasses, head-mounted displays (HMDs), and smart contact lenses. An image pickup and display apparatus used in such an application example includes an image pickup apparatus that can photoelectrically convert visible light and a display apparatus that can emit visible light.

Figure 6A:
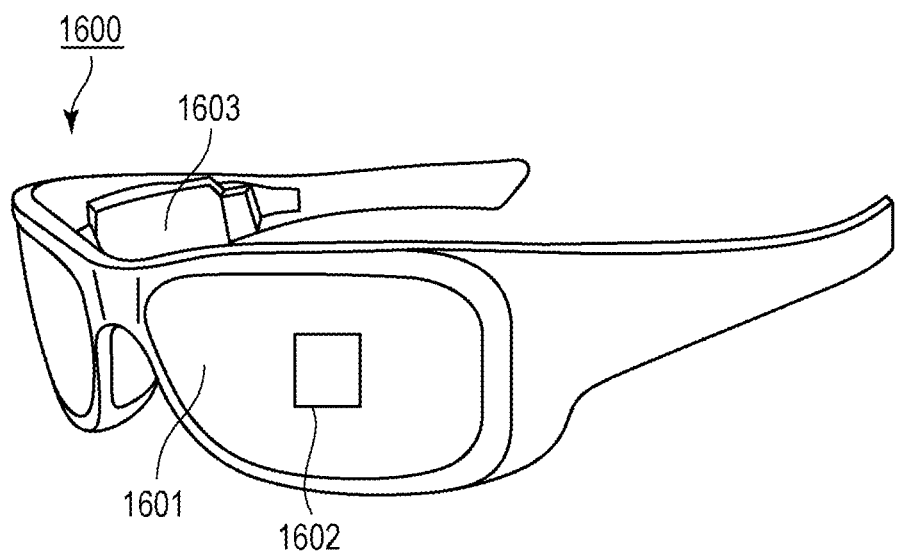
FIG. 6A schematically illustrates an example of a wearable device according to an embodiment of the present disclosure.

FIG. 6A illustrates eyeglasses 1600 (smart glasses) according to one application example. An image pickup apparatus 1602, such as a complementary metal-oxide semiconductor (CMOS) sensor or a single-photon avalanche diode (SPAD), is provided on the front side of a lens 1601 of the eyeglasses 1600. The display apparatus according to any one of the above embodiments is provided on the rear side of the lens 1601.

The eyeglasses 1600 further include a controller 1603. The controller 1603 functions as a power source for supplying electricity to the image pickup apparatus 1602 and the display apparatus according to the embodiment. The controller 1603 controls the operation of the image pickup apparatus 1602 and the display apparatus. The lens 1601 is provided with an optical system for focusing light on the image pickup apparatus 1602.

Figure 6B:
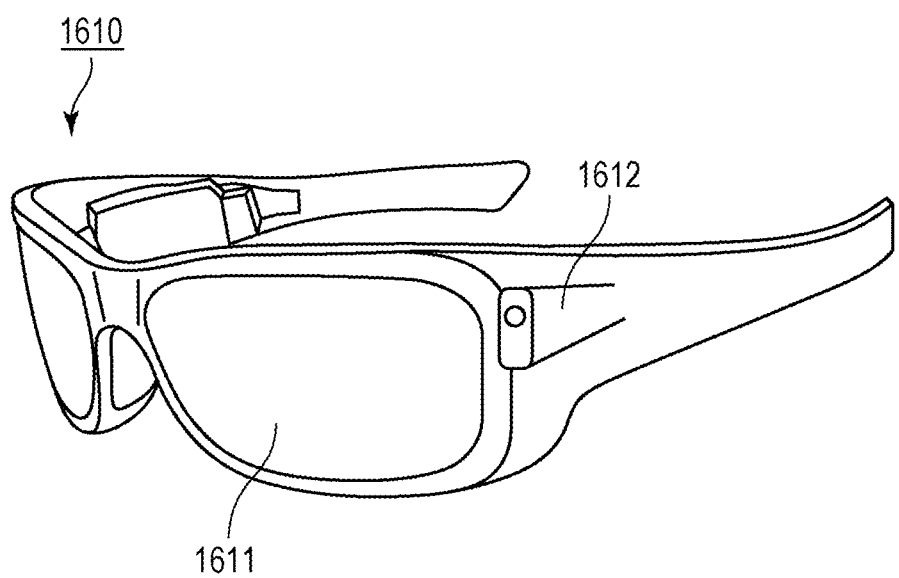
FIG. 6B schematically illustrates an example of a wearable device according to an embodiment of the present disclosure, the wearable device including an image pickup apparatus.

FIG. 6B illustrates eyeglasses 1610 (smart glasses) according to one application example. The eyeglasses 1610 include a controller 1612, and the controller 1612 includes an image pickup apparatus corresponding to the image pickup apparatus 1602 and a display apparatus. A lens 1611 is provided with an optical system for focusing light on the image pickup apparatus in the controller 1612 and projecting light emitted from the display apparatus, and an image is projected onto the lens 1611. The controller 1612 functions as a power source for supplying electricity to the image pickup apparatus and the display apparatus and also controls the operation of the image pickup apparatus and the display apparatus. The controller may include a gaze detection unit that detects the gaze of a wearer. The gaze may be detected using infrared radiation. An infrared light emission unit emits infrared light to an eyeball of a user gazing at a displayed image. The reflection of the emitted infrared light from the eyeball is detected by an image pickup unit including a light-receiving element, whereby a captured image of the eyeball is obtained. Due to the presence of a reduction unit that reduces light from the infrared light emission unit to the display unit in plan view, degradation of image quality is reduced.

The gaze of the user toward the displayed image is detected from the captured image of the eyeball obtained by infrared imaging. Any known method may be used for the gaze detection using the captured image of the eyeball. For example, a gaze detection method based on a Purkinje image formed by the reflection of irradiation light on a cornea may be used.

More specifically, a gaze detection process based on a pupil-corneal reflection method is performed. Using the pupil-corneal reflection method, a gaze vector representing the direction (rotation angle) of the eyeball is calculated on the basis of a pupil image and a Purkinje image included in the captured image of the eyeball, whereby the gaze of the user is detected.

A display apparatus according to an embodiment of the present disclosure may include an image pickup apparatus including a light-receiving element and may control a displayed image on the display apparatus on the basis of the gaze information of the user from the image pickup apparatus.

Specifically, the display apparatus determines, on the basis of the gaze information, a first visual field at which the user gazes and a second visual field other than the first visual field. The first visual field and the second visual field may be determined by the controller of the display apparatus, or may be determined by an external controller and sent therefrom. In a display area of the display apparatus, the display resolution of the first visual field may be controlled to be higher than the display resolution in the second visual field. That is, the resolution in the second visual field may be set to be lower than that in the first visual field.

The display area includes a first display area and a second display area different from the first display area, and an area of high priority is determined from the first display area and the second display area on the basis of the gaze information. The first display area and the second display area may be determined by the controller of the display apparatus, or may be determined by an external controller and sent therefrom. The resolution in the area of high priority may be controlled to be higher than the resolution in the area other than the area of high priority. That is, the resolution in an area of relatively low priority may be set to be lower.

Artificial intelligence (AI) may be used to determine the first visual field or the area of high priority. AI may be a model configured to estimate, from an image of an eyeball, the angle of gaze and the distance to an object gazed, by using the image of the eyeball and the actual direction of gaze of the eyeball in the image as teaching data. The AI program may be included in the display apparatus, the image pickup apparatus, or an external apparatus. When the AI program is included in the external apparatus, the obtained data is transmitted to the display apparatus via communications.

When display control is performed on the basis of visual recognition, smart glasses further including an image pickup apparatus that captures an external image are suitable for use. Smart glasses can display captured external information in real time.

Figure 7:
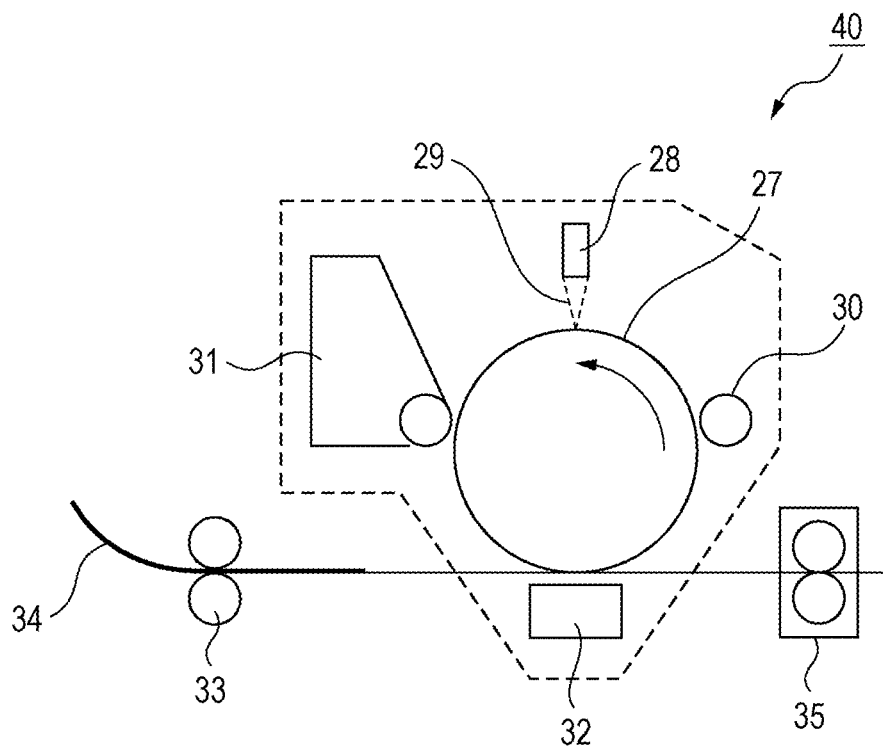
FIG. 7 schematically illustrates an example of an image-forming apparatus according to an embodiment of the present disclosure.

FIG. 7 schematically illustrates an example of an image-forming apparatus according to an embodiment. An image-forming apparatus 40 is an electrophotographic image-forming apparatus and includes a photoreceptor 27, an exposure light source 28, a charging unit 30, a developing unit 31, a transfer unit 32, a conveyer roller 33, and a fixing unit 35. The exposure light source 28 emits light 29, and an electrostatic latent image is formed on the surface of the photoreceptor 27. The exposure light source 28 includes the organic light-emitting element according to this embodiment. The developing unit 31 contains toner and the like. The charging unit 30 charges the photoreceptor 27. The transfer unit 32 transfers a developed image onto a recording medium 34. The conveyer roller 33 conveys the recording medium 34. The recording medium 34 is paper, for example. The fixing unit 35 fixes an image formed on the recording medium 34.

Figure 8A:
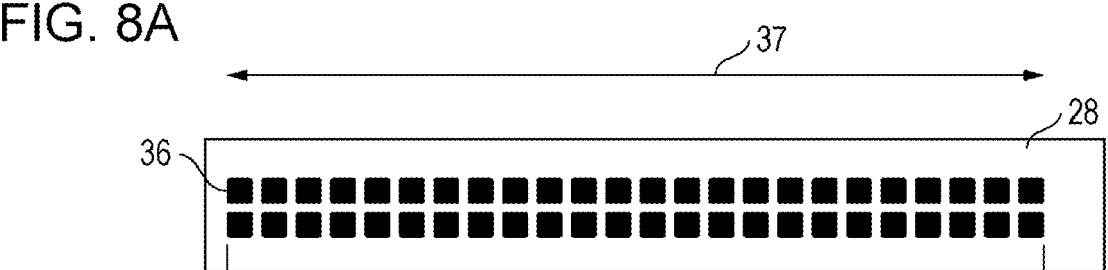
FIGS. 8A and 8B each schematically illustrate an example of an exposure light source of an image-forming apparatus according to an embodiment of the present disclosure.
Figure 8B:
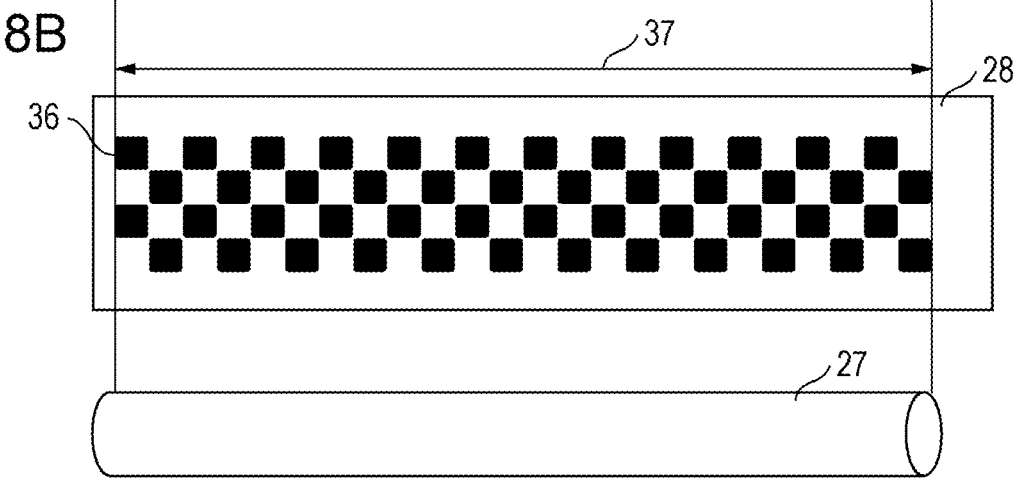

FIGS. 8A and 8B each illustrate the exposure light source 28 and each schematically illustrate how a plurality of light-emitting portions 36 are arranged on a long substrate. An arrow 37 indicates the row direction in which the organic light-emitting elements are arranged. The row direction is the same as the direction of the rotation axis of the photoreceptor 27. This direction can also be referred to as the major-axis direction of the photoreceptor 27. In FIG. 8A, the light-emitting portions 36 are arranged in the major-axis direction of the photoreceptor 27. In FIG. 8B, unlike FIG. 8A, the light-emitting portions 36 are alternately arranged in the row direction in a first row and a second row. The first row and the second row are located at different positions in the column direction. In the first row, the plurality of light-emitting portions 36 are arranged at intervals. In the second row, the light-emitting portions 36 are arranged at positions corresponding to the spaces between the light-emitting portions 36 in the first row. That is, the plurality of light-emitting portions 36 are arranged at intervals also in the column direction. The arrangement in FIG. 8B can be referred to as, for example, a lattice arrangement, a staggered arrangement, or a checkered pattern.

As described above, the use of an apparatus including the organic light-emitting element according to this embodiment enables a stable display with good image quality over a long period of time.

EXAMPLES

Hereinafter, the present disclosure will be described with reference to Examples. However, the present disclosure is not limited to these Examples.

Example 1 (Synthesis of Exemplary Compound A1)

Exemplary compound A1 was synthesized according to the following scheme. The following scheme is the reaction scheme described above where compound E1, in which X is an oxygen atom, is used as compound (a).

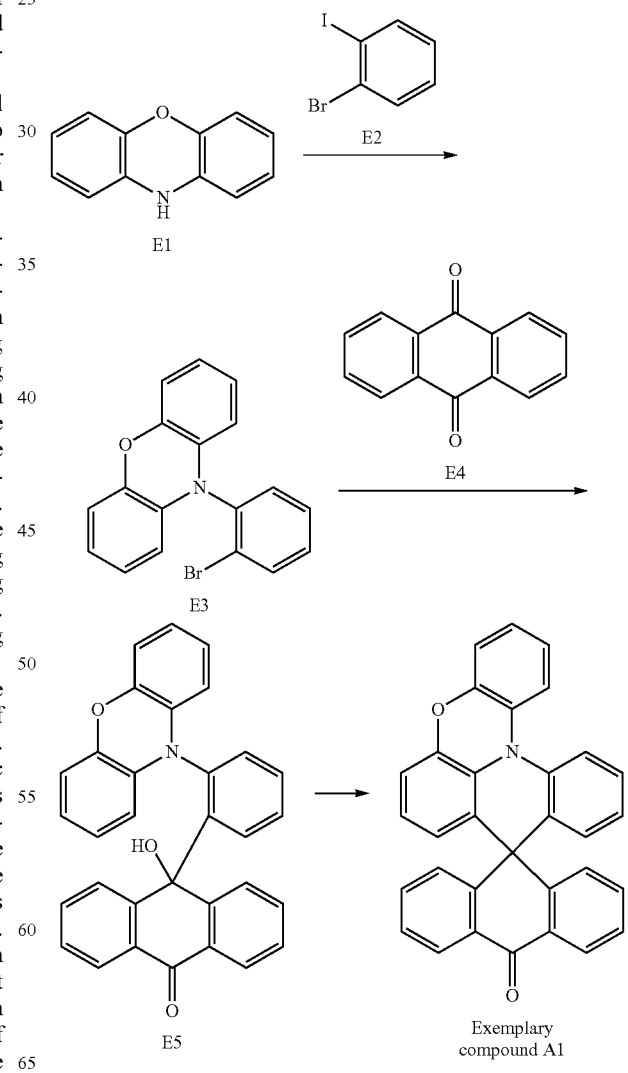

(1) Synthesis of Compound E3

The following reagents and solvent were placed in a 300 ml recovery flask.
Compound E1: 5.0 g (27.3 mmol)
Compound E2: 7.7 g (27.3 mmol)
$Pd_2(dba)_3$: 0.7 g (0.8 mmol)
$P(t-Bu)_3$: 0.6 g (2.7 mmol)
NaO-t-Bu: 5.2 g (54.6 mmol)
Toluene: 100 ml Next, the reaction solution was stirred with heating at 100° C. for 12 hours under a stream of nitrogen. After the stirring with heating, the resultant was extracted with toluene, and the organic layer was concentrated to dryness to obtain a solid. The solid obtained was purified by silica gel column chromatography (mixture of toluene and heptane) to obtain 6.5 g of compound E3 (yield: 70%).

(2) Synthesis of Compound E5

The following reagent and solvent were placed in a 300 ml recovery flask.
Compound E3: 6.0 g (17.7 mmol)
THF: 200 ml Next, 11 ml of n-butyl lithium (1.6 mol/L, hexane solution) was gradually added dropwise to the above reaction solution at −78° C. under a stream of nitrogen. After the dropwise addition, the reaction solution was stirred for 1 hour while maintaining the temperature at −78° C. Thereafter, 3.3 g (15.9 mmol) of compound E4 dissolved in 30 ml of THF was gradually added dropwise to the reaction solution at −78° C. After the dropwise addition, the reaction solution was gradually allowed to warm to room temperature and stirred for 2 hours at room temperature. The reaction solution was quenched with an aqueous ammonium chloride solution and extracted with ethyl acetate. The organic layer was concentrated to dryness to obtain 2.3 g of compound E5 (yield: 28%).

(3) Synthesis of Exemplary Compound A1

The following reagent and solvents were placed in a 200 ml recovery flask.
Compound E5: 2.0 g (4.3 mmol)
Acetic acid: 100 ml
Hydrochloric acid: 10 ml Next, the above reaction solution was stirred with heating for 10 hours under reflux under a stream of nitrogen. After completion of the reaction, water was added, and the precipitated solid was collected by filtration. The solid obtained was purified by silica gel column chromatography (mixture of chloroform and ethyl acetate) to obtain 0.7 g of a yellow solid (compound A1) (yield: 38%).

The yellow solid (compound A1) obtained was subjected to mass spectrometry using MALDI-TOF-MS (Autoflex LRF manufactured by Bruker Corporation). The mass spectrometry confirmed that compound C-1 of interest was synthesized.

MALDI-TOF-MS
Measured value: m/z=450, calculated value: $C_{32}H_{19}NO_2$=450

Examples 2 to 17 and Reference Examples 18 to 22 (Synthesis of Exemplary Compounds and Reference Compounds)

Exemplary compounds of Examples 2 to 17 and reference compounds of Reference Examples 18 to 22 shown in Tables 2 to 4 were each synthesized in the same manner as in Example 1 except that raw material E1 in Example 1 was replaced with raw material 1, raw material E2 with raw material 2, and raw material E4 with raw material 3. Measured values (m/z) of mass spectrometry determined in the same manner as in Example 1 are also shown in Tables 2 to 4.

TABLE 2

| | Exemplary compound | Raw material 1 | Raw material 2 | Raw material 3 | m/z |
|---|---|---|---|---|---|
| Example 2 | A2 | dimethyl phenoxazine | 2-bromoiodobenzene | anthraquinone | 478 |
| Example 3 | A4 | phenoxazine | 4-tert-butyl-2-bromo-1-iodobenzene | anthraquinone | 506 |
| Example 4 | A5 | 4,6-diphenylphenoxazine | 2-bromoiodobenzene | anthraquinone | 602 |

TABLE 2-continued

| Exemplary compound | Raw material 1 | Raw material 2 | Raw material 3 | m/z |
|---|---|---|---|---|
| Example 5 | A8 | phenoxazine | 3-bromo-4-iodobiphenyl | anthraquinone | 526 |
| Example 6 | A12 | phenoxazine | 2-(3-bromo-4-iodophenyl)naphthalene | anthraquinone | 576 |
| Example 7 | A14 | phenoxazine | 1-bromo-2-iodobenzene | 2,6-dimethylanthraquinone | 478 |
| Example 8 | A17 | phenoxazine | 1-bromo-2-iodobenzene | 2,6-diphenylanthraquinone | 602 |
| Example 9 | A23 | 3,7-dimethoxyphenoxazine | 1-bromo-2-iodobenzene | anthraquinone | 510 |

TABLE 3

| Exemplary compound | Raw material 1 | Raw material 2 | Raw material 3 | m/z |
|---|---|---|---|---|
| Example 10 | B1 | phenothiazine | 1-bromo-2-iodobenzene | anthraquinone | 466 |

TABLE 3-continued

| Exemplary compound | | Raw material 1 | Raw material 2 | Raw material 3 | m/z |
|---|---|---|---|---|---|
| Example 11 | B4 | | | | 522 |
| Example 12 | B5 | | | | 522 |
| Example 13 | B7 | | | | 570 |
| Example 14 | B13 | | | | 770 |
| Example 15 | B16 | | | | 578 |
| Example 16 | B24 | | | | 631 |

TABLE 4

| Exemplary compound | Raw material 1 | Raw material 2 | Raw material 3 | m/z |
|---|---|---|---|---|
| Example 17 — C1 | phenoselenazine | 1-bromo-2-iodobenzene | anthraquinone | 512 |
| Reference Example 18 — D1 | 9,9-dimethylacridine | 1-bromo-2-iodobenzene | anthraquinone | 476 |
| Reference Example 19 — D3 | 9,9-dimethylacridine | 4-tert-butyl-1-bromo-2-iodobenzene | anthraquinone | 532 |
| Reference Example 20 — D5 | 9,9-dimethylacridine | mesityl-substituted bromoiodobiphenyl | anthraquinone | 594 |
| Reference Example 21 — D8 | 9,9-dimethylacridine | phenanthrenyl-substituted bromoiodobenzene | anthraquinone | 652 |
| Reference Example 22 — D14 | 2,7-difluoro-9,9-dimethylacridine | 1-bromo-2-iodobenzene | anthraquinone | 512 |

Example 23

In this Example, an organic EL element having a bottom-emission structure was produced in which an anode, a hole injection layer, a hole transport layer, an electron blocking layer, a light-emitting layer, a hole blocking layer, an electron transport layer, an electron injection layer, and a cathode were sequentially formed on a substrate.

First, an ITO film was formed on a glass substrate and subjected to desired patterning to form an ITO electrode (anode). At this time, the ITO electrode was formed so as to have a thickness of 100 nm. The substrate on which the ITO electrode was formed in this manner was used as an ITO substrate in the following process. Next, organic compound layers and an electrode layer shown in Table 5 below were continuously formed on the ITO substrate by performing vacuum deposition by resistance heating in a vacuum chamber. At this time, the electrode area of the electrode (metal electrode layer, cathode) opposed to the ITO electrode was set to 3 $mm^2$.

TABLE 5

|  |  | Material | Proportion (mass %) in light-emitting layer | Thickness (nm) |
|---|---|---|---|---|
| Electrode layer | Cathode | Al | — | 100 |
| Organic compound layer | Electron injection layer (EIL) | LiF | — | 1 |
|  | Electron transport layer (ETL) | ET2 | — | 15 |
|  | Hole blocking layer (HBL) | ET11 | — | 15 |
|  | Light-emitting layer (EML) Host | EM14 | 88 | 20 |
|  | Light-emitting material | A1 | 12 |  |
|  | Electron blocking layer (EBL) | HT12 | — | 15 |
|  | Hole transport layer (HTL) | HT3 | — | 30 |
|  | Hole injection layer (HIL) | HT16 | — | 5 |

The characteristics of the element obtained were measured and evaluated. As an initial characteristic associated with light emission, green light emission with a maximum external quantum efficiency (E.Q.E.) of 11.2% was obtained. Regarding measurement apparatuses, specifically, the current-voltage characteristics were measured with a Hewlett-Packard 4140B microammeter, and the emission luminance was measured with a Topcon BM7. Furthermore, a continuous driving test at a current density of 50 mA/$cm^2$ was performed to measure the time (LT95) taken for the luminance degradation to reach 5%. The time was 110 hours.

Examples 24 to 27, Reference Example 28, and Comparative Examples 1 and 2

Organic light-emitting elements were produced in the same manner as in Example 23 except that the materials used to form the layers were appropriately changed to compounds shown in Table 6. For the layers not listed in Table 6, the same configuration as in Example 23 was used. The characteristics of the elements obtained were measured and evaluated in the same manner as in Example 23. The results of the measurements are shown in Table 6 together with the measurement results of Example 23.

TABLE 6

|  |  |  | EML | | | | E.Q.E. [%] | LT95 [h] | Emission color |
|---|---|---|---|---|---|---|---|---|---|
|  | HTL | EBL | Host | Light-emitting material | HBL | ETL |  |  |  |
| Example 23 | HT3 | HT12 | EMU | A1 | ET11 | ET2 | 11.2 | 110 | Green |
| Example 24 | HT3 | HT12 | EMU | A4 | ET10 | ET2 | 11.7 | 101 | Green |
| Example 25 | HT3 | HT9 | EM11 | B1 | ET12 | ET2 | 11.9 | 120 | Blue-green |
| Example 26 | HT3 | HT12 | EM9 | B13 | ET12 | ET2 | 12.5 | 124 | Blue-green |
| Example 27 | HT2 | HT11 | EM6 | C1 | ET22 | ET2 | 11.8 | 119 | Blue |
| Reference Example 28 | HT2 | HT10 | EM10 | D1 | ET12 | ET5 | 13.1 | 92 | Green |

TABLE 6-continued

| | HTL | EBL | Host | EML Light-emitting material | HBL | ETL | E.Q.E. [%] | LT95 [h] | Emission color |
|---|---|---|---|---|---|---|---|---|---|
| Comparative Example 1 | HT3 | HT12 | EMU | Comparative compound 1-a | ET11 | ET2 | 9.2 | 74 | Blue-green |
| Comparative Example 2 | HT3 | HT12 | EMU | Comparative compound 2-a | ET11 | ET2 | 9.5 | 90 | Blue-green |

As shown in Table 6, in Examples 23 to 27, organic light-emitting elements each having a high maximum external quantum efficiency (E.Q.E.) and a long 5% degradation lifetime (LT95) were obtained. That is, in Examples 23 to 27, organic light-emitting elements having high light emission efficiency and high driving durability were obtained. In other words, the exemplary compounds shown in Table 6 were found to be compounds that exhibit high light emission efficiency and high driving durability when used for a light-emitting layer in an organic light-emitting element, more specifically, when used as a light-emitting material in the light-emitting layer.

By contrast, as shown in Table 6, the organic light-emitting elements of Comparative Examples 1 and 2 in which comparative compounds 1-a and 2-a were respectively used each had a low maximum external quantum efficiency (E.Q.E.) and a short 5% degradation lifetime (LT95).

The compositions of Comparative Examples 1 and 2 and Example 23 are the same except for the light-emitting material.

In Comparative Examples 1 and 2, comparative compounds 1-a and 2-a were respectively used as light-emitting materials, and in Example 23, compound A1, one of the compounds of the present disclosure, was used as a light-emitting material. As described using FIGS. 9 and 10, comparative compound 1-a has a structure in which one of the aromatic rings bonded to the amino group in the basic skeleton is not fused to any other aromatic ring, and the basic skeleton has a symmetric structure. Thus, for the reasons described above, the organic light-emitting element of Comparative Example 1 had low light emission efficiency and low driving durability. Comparative compound 2-a has a structure having no chalcogen atoms in the basic skeleton. Thus, for the reasons described above, the organic light-emitting element of Comparative Example 2 had low light emission efficiency. By contrast, as described using FIGS. 9 and 10, compound A1 has a structure in which the aromatic ring bonded to the amino group is fused, through a chalcogen atom, to another moiety bonded to the amino group. Furthermore, the basic skeleton of compound A1 has an asymmetric structure. Furthermore, HOMO is distributed on the chalcogen atom in the basic skeleton.

Thus, for the reasons described above, the organic light-emitting element of Example 23 had high light emission efficiency and high driving durability.

Example 29

In this Example, an organic EL element having a bottom-emission structure was produced in which an anode, a hole injection layer, a hole transport layer, an electron blocking layer, a light-emitting layer, a hole blocking layer, an electron transport layer, an electron injection layer, and a cathode were sequentially formed on a substrate.

First, an ITO film was formed on a glass substrate and subjected to desired patterning to form an ITO electrode (anode). At this time, the ITO electrode was formed so as to have a thickness of 100 nm. The substrate on which the ITO electrode was formed in this manner was used as an ITO substrate in the following process. Next, organic compound layers and an electrode layer shown in Table 7 below were continuously formed on the ITO substrate by performing vacuum deposition by resistance heating in a vacuum chamber. At this time, the electrode area of the electrode (metal electrode layer, cathode) opposed to the ITO electrode was set to 3 mm$^2$.

TABLE 7

| | | Material | Proportion (mass %) in light-emitting layer | Thickness (nm) |
|---|---|---|---|---|
| Electrode layer | Cathode | Al | — | 100 |
| Organic compound layer | Electron injection layer (EIL) | LiF | — | 1 |
| | Electron transport layer (ETL) | ET2 | — | 15 |
| | Hole blocking layer (HBL) | ET11 | — | 15 |
| | Light-emitting layer (EML) Host | EM11 | 82 | 20 |
| | Assist | A1 | 15 | |
| | Light-emitting material | GD6 | 3 | |
| | Electron blocking layer (EBL) | HT12 | — | 15 |
| | Hole transport layer (HTL) | HT3 | — | 30 |
| | Hole injection layer (HIL) | HT16 | — | 5 |

The characteristics of the element obtained were measured and evaluated. As an initial characteristic associated with light emission, green light emission with a maximum external quantum efficiency (E.Q.E.) of 10.3% was obtained. Regarding measurement apparatuses, specifically, the current-voltage characteristics were measured with a Hewlett-Packard 4140B microammeter, and the emission luminance was measured with a Topcon BM7. Furthermore, a continuous driving test at a current density of 50 mA/cm$^2$ was performed to measure the time (LT95) taken for the luminance degradation to reach 5%. The time was 170 hours.

Examples 30 to 36, Reference Examples 37 to 39, and Comparative Example 2

Organic light-emitting elements were produced in the same manner as in Example 29 except that the materials were appropriately changed to compounds shown in Table 8. For the layers not listed in Table 8, the same configuration as in Example 29 was used. The characteristics of the elements obtained were measured and evaluated in the same manner as in Example 29. The results of the measurements are shown in Table 8 together with the measurement results of Example 29.

TABLE 8

| | | | EML | | | | | | |
|---|---|---|---|---|---|---|---|---|---|
| | HTL | EBL | Host | Assist | Light-emitting material | HBL | ETL | E.Q.E. [%] | LT95 [h] | Emission color |
| Example 29 | HT3 | HT12 | EM11 | A1 | GD6 | ET11 | ET2 | 10.3 | 170 | Green |
| Example 30 | HT3 | HT11 | EMU | A4 | GD1 | ET12 | ET2 | 10.7 | 162 | Green |
| Example 31 | HT3 | HT12 | EMU | A8 | GD6 | ET11 | ET2 | 10.4 | 174 | Green |
| Example 32 | HT2 | HT11 | EM9 | B1 | GD8 | ET12 | ET2 | 11.0 | 192 | Green |
| Example 33 | HT2 | HT12 | EMU | B4 | GD9 | ET11 | ET5 | 11.5 | 181 | Green |
| Example 34 | HT2 | HT11 | EM11 | B5 | GD9 | ET16 | ET7 | 11.4 | 182 | Green |
| Example 35 | HT3 | HT12 | EMU | B13 | GD8 | ET11 | ET2 | 11.9 | 190 | Green |
| Example 36 | HT2 | HT12 | EMU | B16 | GD7 | ET11 | ET5 | 11.7 | 180 | Green |
| Reference Example 37 | HT2 | HT12 | EM11 | D1 | GD8 | ET12 | ET2 | 12.2 | 169 | Green |
| Reference Example 38 | HT2 | HT12 | EM11 | D5 | GD7 | ET12 | ET5 | 12.3 | 165 | Green |
| Reference Example 39 | HT3 | HT10 | EM9 | D8 | GD8 | ET12 | ET7 | 12.1 | 162 | Green |
| Comparative Example 3 | HT3 | HT12 | EM11 | Comparative compound 1-a | GD6 | ET11 | ET2 | 9.7 | 138 | Green |
| Comparative Example 4 | HT3 | HT12 | EM11 | Comparative compound 2-a | GD6 | ET11 | ET2 | 9.9 | 151 | Green |

As shown in Table 8, in Examples 29 to 36, organic light-emitting elements each having a high maximum external quantum efficiency (E.Q.E.) and a long 5% degradation lifetime (LT95) were obtained. That is, in Examples 29 to 36, organic light-emitting elements having high light emission efficiency and high driving durability were obtained. In other words, the exemplary compounds shown in Table 8 were found to be compounds that exhibit high light emission efficiency and high driving durability when used for a light-emitting layer in an organic light-emitting element, more specifically, when used as an assist material in the light-emitting layer.

By contrast, as shown in Table 8, the organic light-emitting elements of Comparative Examples 3 and 4 in which comparative compounds 1-a and 2-a were respectively used each had a low maximum external quantum efficiency (E.Q.E.) and a short 5% degradation lifetime (LT95).

The compositions of Comparative Examples 3 and 4 and Example 29 are the same except for the assist material. In Comparative Examples 3 and 4, comparative compounds 1-a and 2-a were respectively used as assist materials, and in Example 29, compound A1, one of the compounds of the present disclosure, was used as an assist material.

As described using FIGS. 9 and 10, comparative compound 1-a has a structure in which one of the aromatic rings bonded to the amino group in the basic skeleton is not fused to any other aromatic ring, and the basic skeleton has a symmetric structure. Thus, for the reasons described above, the organic light-emitting element of Comparative Example 3 had low light emission efficiency and low driving durability. Comparative compound 2-a has a structure having no chalcogen atoms in the basic skeleton. Thus, for the reasons described above, the organic light-emitting element of Comparative Example 4 had low light emission efficiency. By contrast, as described using FIGS. 9 and 10, compound A1 has a structure in which the aromatic ring bonded to the amino group is fused, through a chalcogen atom, to another moiety bonded to the amino group. Furthermore, the basic skeleton of compound A1 has an asymmetric structure. Furthermore, HOMO is distributed on the chalcogen atom in the basic skeleton. Thus, for the reasons described above, the organic light-emitting element of Example 29 had high light emission efficiency and high driving durability.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-216220, filed Dec. 25, 2020, which is hereby incorporated by reference herein in its entirety.

What is claimed is:

1. An organic compound represented by general formula [1-1];

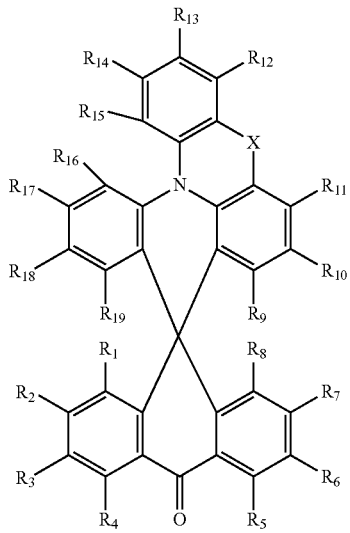

[1-1]

wherein, in general formula [1-1], X is an oxygen atom, a sulfur atom, a selenium atom, or a tellurium atom, and $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aromatic hydrocarbon group, a substituted or unsubstituted heterocyclic group, a substituted or unsubstituted aryloxy group, a substituted or unsubstituted silyl group, and a cyano group; and wherein $R_{19}$ represents a hydrogen atom.

2. The organic compound according to claim 1, wherein in general formula [1-1], X is an oxygen atom.

3. The organic compound according to claim 1, wherein in general formula [1-1], X is a sulfur atom.

4. The organic compound according to claim 1, wherein in general formula [1-1], X is a selenium atom.

5. The organic compound according to claim 1, wherein $R_1$ to $R_{18}$ are each independently selected from the group consisting of a hydrogen atom, a halogen atom, a substituted or unsubstituted alkyl group having 1 to 10 carbon atoms, a substituted or unsubstituted alkoxy group having 1 to 10 carbon atoms, a substituted or unsubstituted amino group, a substituted or unsubstituted aromatic hydrocarbon group having 6 to 60 carbon atoms, a substituted or unsubstituted heterocyclic group having 3 to 60 carbon atoms, a substituted or unsubstituted aryloxy group, a substituted or unsubstituted silyl group, and a cyano group.

6. An organic light-emitting element comprising:
an anode;
a cathode; and
at least one organic compound layer disposed between the anode and the cathode,
wherein the at least one organic compound layer contains the organic compound according to claim 1.

7. The organic light-emitting element according to claim 6, wherein the at least one layer containing the organic compound is a light-emitting layer.

8. The organic light-emitting element according to claim 7, wherein the light-emitting layer further contains a host material.

9. The organic light-emitting element according to claim 8, wherein the host material is a hydrocarbon compound.

10. The organic light-emitting element according to claim 8, wherein the light-emitting layer further contains a light-emitting material.

11. The organic light-emitting element according to claim 10, wherein the light-emitting material is a hydrocarbon compound.

12. The organic light-emitting element according to claim 7, wherein the light-emitting layer emits green light.

13. The organic light-emitting element according to claim 7, wherein the light-emitting layer emits red light.

14. A display apparatus comprising a plurality of pixels, wherein at least one of the plurality of pixels includes the organic light-emitting element according to claim 6 and a transistor connected to the organic light-emitting element.

15. A display apparatus comprising a plurality of pixels, wherein at least one of the plurality of pixels includes the organic light-emitting element according to claim 6, a transistor connected to the organic light-emitting element, and a color filter.

16. A photoelectric conversion apparatus comprising:
an optical unit including a plurality of lenses;
an image pickup element that receives light that has passed through the optical unit; and
a display unit that displays an image captured by the image pickup element,
wherein the display unit includes the organic light-emitting element according to claim 6.

17. An electronic apparatus comprising:
a display unit including the organic light-emitting element according to claim 6;
a housing provided with the display unit; and
a communication unit that is provided in the housing and communicates with an external unit.

18. An illumination apparatus comprising:
a light source including the organic light-emitting element according to claim 6; and
a light diffusion unit or an optical filter that transmits light emitted from the light source.

19. A moving object comprising:
a lighting fixture including the organic light-emitting element according to claim 6; and
a body provided with the lighting fixture.

20. An exposure light source for an electrophotographic image-forming apparatus, comprising the organic light-emitting element according to claim 6.

* * * * *